United States Patent
Lee et al.

(10) Patent No.: US 12,213,764 B2
(45) Date of Patent: Feb. 4, 2025

(54) BIO IMAGING SYSTEM AND BIO IMAGING METHOD

(71) Applicant: Samsung Electronics Co., Ltd., Suwon-si (KR)

(72) Inventors: Gae Hwang Lee, Seongnam-si (KR); Youngjun Yun, Seongnam-si (KR); Hyun Bum Kang, Yongin-si (KR); Jong Won Chung, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 497 days.

(21) Appl. No.: 17/519,974

(22) Filed: Nov. 5, 2021

(65) Prior Publication Data
US 2022/0280044 A1 Sep. 8, 2022

(30) Foreign Application Priority Data

Mar. 5, 2021 (KR) ........................ 10-2021-0029508

(51) Int. Cl.
| | |
|---|---|
| *A61B 5/00* | (2006.01) |
| *G02B 5/20* | (2006.01) |
| *G02F 1/17* | (2019.01) |
| *G16H 30/40* | (2018.01) |
| *G02B 5/02* | (2006.01) |

(52) U.S. Cl.
CPC ............ *A61B 5/0075* (2013.01); *G02B 5/201* (2013.01); *G02F 1/17* (2013.01); *G16H 30/40* (2018.01); *A61B 2562/0238* (2013.01); *A61B 2562/0242* (2013.01); *A61B 2576/00* (2013.01); *G02B 5/0278* (2013.01)

(58) Field of Classification Search
CPC .................................................. A61B 5/0075
See application file for complete search history.

(56) References Cited

U.S. PATENT DOCUMENTS

| | | |
|---|---|---|
| 8,405,832 B2 | 3/2013 | Schmaelzle et al. |
| 10,644,186 B2 | 5/2020 | Yoo et al. |
| 2009/0269244 A1 | 10/2009 | Cunningham et al. |
| 2012/0165759 A1 | 6/2012 | Rogers et al. |
| 2014/0364745 A1 | 12/2014 | Patwardhan |
| 2017/0337412 A1 | 11/2017 | Bhat et al. |
| 2017/0337413 A1 | 11/2017 | Bhat et al. |
| 2018/0000387 A1 | 1/2018 | Heo et al. |
| 2018/0123050 A1 | 5/2018 | Rosselli et al. |
| 2019/0005301 A1 | 1/2019 | Chen et al. |

(Continued)

FOREIGN PATENT DOCUMENTS

| | | |
|---|---|---|
| KR | 10-1667917 B1 | 10/2016 |
| KR | 10-2019-0114386 A | 10/2019 |
| KR | 10-2019-0119382 A | 10/2019 |

OTHER PUBLICATIONS

Extended European Search Report dated May 20, 2022 for corresponding European Application No. 21207213.6.

*Primary Examiner* — Joseph M Santos Rodriguez
(74) *Attorney, Agent, or Firm* — HARNESS, DICKEY & PIERCE, P.L.C.

(57) ABSTRACT

A bio imaging system includes a substrate, a light source on the substrate, and a sensor on the substrate, wherein at least one of the light source or the sensor is configured to emit or absorb light of different wavelength spectrum. The bio imaging system is configured to combine a plurality of images obtained based on the light of different wavelength spectra to obtain a three-dimensional image of an internal tissue of a living body.

33 Claims, 34 Drawing Sheets

(56) References Cited

U.S. PATENT DOCUMENTS

2019/0038111 A1    2/2019   Endo
2019/0216340 A1    7/2019   Holz et al.
2020/0158566 A1    5/2020   Ota et al.
2020/0178810 A1    6/2020   Zott et al.
2021/0007617 A1    1/2021   Kim et al.

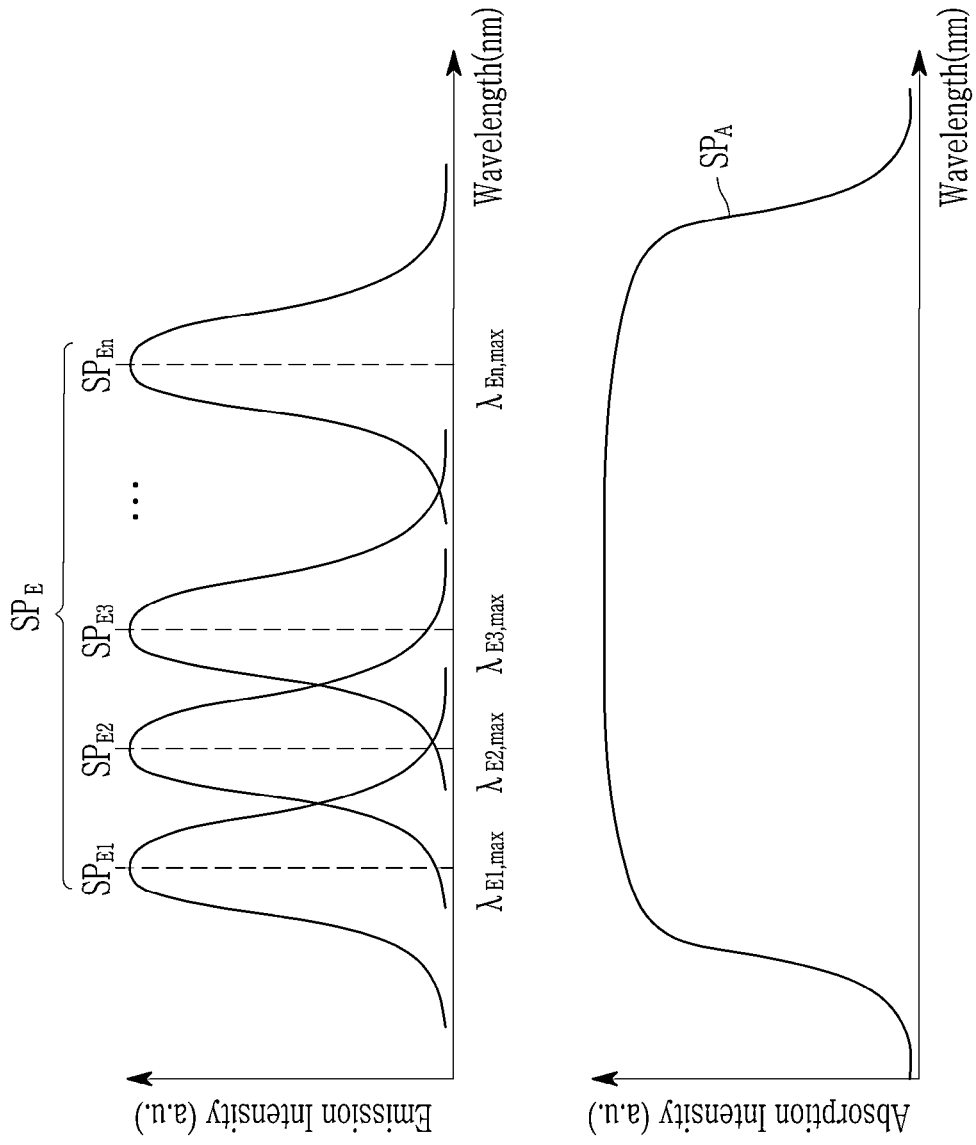

BIO IMAGING SYSTEM AND BIO IMAGING METHOD

CROSS-REFERENCE TO RELATED APPLICATION

This application claims priority to and the benefit, under 35 U.S.C. § 119, of Korean Patent Application No. 10-2021-0029508 filed in the Korean Intellectual Property Office on Mar. 5, 2021, the entire contents of which are incorporated herein by reference.

BACKGROUND

1. Field

A bio imaging system and a bio imaging method are disclosed.

2. Description of the Related Art

Various equipment for obtaining images of internal tissues of a living body such as a blood vessel has been used for various purposes such as medical care or security. For example, an image of the internal tissues of a living body such as blood vessels may be obtained by irradiating the skin with a light source and using a camera.

SUMMARY

Some example embodiments provide a bio imaging system capable of clearly obtaining a three-dimensional image of an internal tissue of a living body located at a specific depth. Such a system may address issues related to images obtained by irradiating the skin with a light source and using a camera, where said images may include all images of skin and blood vessels located at the points where light passes. In particular, such a system may address limitations in selectively obtaining an image of a target internal tissue of a living body. In addition, such a system may more easily obtain a clear image, in comparison to systems that obtain images by irradiating the skin with a light source and using a camera, due to mitigating or preventing issues relating to light scattering by the skin and thus improving clarity of the image.

Some example embodiments provide a bio imaging method using the bio imaging system.

Some example embodiments provide an electronic device including the bio imaging system.

According to some example embodiments, a bio imaging system may include a substrate, a light source on the substrate, and a sensor on the substrate. At least one of the light source or the sensor may be configured to emit or absorb light of different wavelength spectra. The bio imaging system may be configured to combine a plurality of images obtained based on the light of different wavelength spectra to obtain a three-dimensional image of an internal tissue of a living body.

The light source may include first, second, and third light sources configured to emit light of different emission spectra within visible to infrared wavelength spectra.

The first light source may include a first light emitting element configured to emit light of a first emission spectrum having a first maximum emission wavelength. The second light source may include a second light emitting element configured to emit light of a second emission spectrum having a second maximum emission wavelength that is longer than the first maximum emission wavelength. The third light source may include a third light emitting element configured to emit light of a third emission spectrum having a third maximum emission wavelength that is longer than the second maximum emission wavelength. A difference between the first and second maximum emission wavelengths and a difference between the second and third maximum emission wavelengths may each be greater than or equal to about 10 nm.

Each of the first, second and third light sources may include a separate light emitting element of a plurality of light emitting elements that is configured to emit light of a same emission spectrum. Each of the first, second and third light sources may further include a separate color filter of a plurality of color filters, wherein the plurality of color filters are overlapped with separate, respective light emitting elements of the plurality of light emitting elements in a direction that extends perpendicular to an in-plane direction of the substrate.

The plurality of color filters may include a first color filter included in the first light source, the first color filter configured to selectively transmit light of a first transmission spectrum having a first maximum transmission wavelength. The plurality of color filters may include a second color filter included in the second light source, the second color filter configured to selectively transmit light of a second transmission spectrum having a second maximum transmission wavelength that is longer than the first maximum transmission wavelength. The plurality of color filters may include a third color filter included in the third light source, the third color filter configured to selectively transmit light of a third transmission spectrum having a third maximum transmission wavelength that is longer than the second maximum transmission wavelength. Each of the first, second, and third maximum transmission wavelengths is within the same emission spectrum that the plurality of light emitting elements are configured to emit. A difference between the first and second maximum transmission wavelengths and a difference between the second and third maximum transmission wavelengths may each be greater than or equal to about 10 nm.

The first, second, and third light sources may extend in a linear sequence along an in-plane direction of the substrate.

The light source may include a plurality of light emitting elements configured to emit light of a same emission spectrum. The bio imaging system may further include a plurality of color filters overlapped with separate, respective light emitting elements of the plurality of light emitting elements in a direction extending perpendicular to an in-plane direction of the substrate, the plurality of color filters configured to provide wavelength selectivity to the same emission spectrum.

The sensor may include first, second, and third sensors configured to absorb light of different absorption spectra in relation to each other within visible to infrared wavelength spectra.

The first sensor may include a first light absorption element configured to absorb light of a first absorption spectrum having a first maximum absorption wavelength. The second sensor may include a second light absorption element configured to absorb light of a second absorption spectrum having a second maximum absorption wavelength, the second maximum absorption wavelength being longer than the first maximum absorption wavelength. The third sensor may include a third light absorption element configured to absorb light of a third absorption spectrum having a third maximum absorption wavelength, the third maximum absorption wavelength being longer than the second maximum absorption wavelength. A difference between the first and second maximum absorption wavelengths and a difference between the second and third maximum absorption wavelengths may each be greater than or equal to about 10 nm.

Each sensor of the first, second, and third sensors may include a separate light absorption element of a plurality of light absorption elements and a separate color filter of a plurality of color filters, the separate color filter of the sensor being overlapped with the separate light absorption element of the sensor in a direction extending perpendicular to an in-plane direction of the substrate, wherein the plurality of light absorption elements are configured to absorb light of a same absorption spectrum.

The plurality of color filters may include a first color filter included in the first sensor, the first color filter selectively transmitting light of a first transmission spectrum having a first maximum transmission wavelength. The plurality of color filters may include a second color filter included in the second sensor, the second color filter selectively transmitting light of a second transmission spectrum having a second maximum transmission wavelength that is longer than the first maximum transmission wavelength. The plurality of color filters may include a third color filter included in the third sensor, the third color filter selectively transmitting light of a third transmission spectrum having a third maximum transmission wavelength that is longer than the second maximum transmission wavelength. Each of the first, second, and third maximum transmission wavelengths is within the same absorption spectrum that the plurality of light absorption elements are configured to absorb. A difference between the first and second maximum transmission wavelengths and a difference between the second and third maximum transmission wavelengths may each be greater than or equal to about 10 nm.

The first, second, and third sensors may extend in a linear sequence along an in-plane direction of the substrate.

The light source may include first, second, and third light sources configured to emit light of different emission spectra within visible to infrared wavelength spectra. The sensor may include first, second, and third sensors configured to absorb light of different absorption spectra in relation to each other within the visible to infrared wavelength spectra.

The light source and the sensor may extend in a linear sequence along an in-plane direction of the substrate.

The bio imaging system may further include a color filter overlapped with the light source or the sensor in a direction that is perpendicular to an in-plane direction of the substrate. The color filter may be a wavelength-tunable color filter that is configured to selectively transmit light of a transmission spectrum that changes depending on a voltage applied to the wavelength-tunable color filter.

The light source may include a wavelength-tunable light emitting element configured to selectively emit light of an emission spectrum that changes based on a voltage applied to the wavelength-tunable light emitting element.

The sensor may include a wavelength-tunable light absorption element configured to selectively absorb light of an absorption spectrum that changes based on a voltage applied to the wavelength-tunable light absorption element.

The bio imaging system may include a light source array including a plurality of light sources, the plurality of light sources including the light source. The bio imaging system may include a sensor array including a plurality of sensors, the plurality of sensors including the sensor. The light source array and the sensor array may be at different heights from the substrate in a direction extending perpendicular to an in-plane direction of the substrate.

The bio imaging system may further include a light diffusion layer between the light source array and the sensor array.

According to some example embodiments, an electronic device may include bio imaging system.

According to some example embodiments, a bio imaging method may include fixing the bio imaging system on a skin of a living body, causing the light source of the bio imaging system to emit light to irradiate the skin, and causing the sensor of the bio imaging system to absorb light scattered and reflected by internal tissue of the living body through the skin to obtain a plurality of images based on light of different wavelength spectra.

The bio imaging method may further include extracting differences between the plurality of images to obtain a plurality of extracted images of the internal tissue of the living body according to a depth from a skin surface of the skin.

The light source may include first, second, and third light sources configured to emit light of different emission spectra within visible to infrared wavelength spectra. The causing the light source of the bio imaging system to emit light may include causing the first, second, and third light sources to sequentially emit light.

The extracting differences between the plurality of images may include extracting a first image of the internal tissue of the living body located at a first depth from the skin surface based on a difference between an image obtained based on causing the second light source to emit light and an image obtained based on causing the first light source to emit light. The extracting differences between the plurality of images may include extracting a second image of the internal tissue of the living body located at a second depth deeper than the first depth based on a difference between an image obtained based on causing the third light source to emit light and the image obtained based on causing the second light source to emit light.

The sensor may include first, second, and third sensors configured to absorb light of different absorption spectra in relation to each other. The extracting differences between the plurality of images may include extracting a first image of the internal tissue of the living body located at a first depth from the skin surface based on a difference between an image obtained based on the second sensor absorbing light and an image obtained based on the first sensor absorbing light. The extracting differences between the plurality of images may include extracting a second image of the internal tissue of the living body located at a second depth deeper than the first depth based on a difference between an image obtained based on the third sensor absorbing light and the image obtained based on the second sensor absorbing light.

The bio imaging method may further include obtaining a three-dimensional image of the internal tissue of the living body based on combining the plurality of extracted images.

The bio imaging method may further include, prior to obtaining the three-dimensional image, obtaining a correction image from a portion of the light source or a portion of the sensor, and correcting the plurality of extracted images using the correction image.

The internal tissue of the living body may include a blood vessel.

According to some example embodiments, a bio imaging system may include a memory storing a program of instructions, and a processor. The processor may be configured to execute the program of instructions to control a light source to cause the light source to emit light to irradiate a skin of a living body, process signals generated by a sensor based on the sensor absorbing light scattered and reflected by internal tissue of the living body through the skin of the living body based on the emitted light irradiating the skin of the living body to generate a plurality of images of the internal tissue based on light of different wavelength spectra, and extract differences between the plurality of images to generate a plurality of extracted images of the internal tissue of the living body according to a depth from a skin surface of the skin.

The light source may include first, second, and third light sources configured to emit light of different emission spectra within visible to infrared wavelength spectra. The controlling the light source may include causing the first, second, and third light sources to sequentially emit light. The extracting differences between the plurality of images may include extracting a first image of an internal tissue of the living body located at a first depth from the skin surface based on a difference between an image generated based on causing the second light source to emit light and an image generated based on causing the first light source to emit light. The extracting differences between the plurality of images may include extracting a second image of the internal tissue of the living body located at a second depth deeper than the first depth based on a difference between an image generated based on causing the third light source to emit light and the image generated based on causing the second light source to emit light.

The sensor may include first, second, and third sensors configured to absorb light of different absorption spectra in relation to each other. The extracting differences between the plurality of images may include extracting a first image of the internal tissue of the living body located at a first depth from the skin surface based on a difference between an image generated based on the second sensor absorbing light and an image generated based on the first sensor absorbing light. The extracting differences between the plurality of images may include extracting a second image of the internal tissue of the living body located at a second depth deeper than the first depth based on a difference between an image generated based on the third sensor absorbing light and the image generated based on the second sensor absorbing light.

The processor may be configured to execute the program of instructions to generate a three-dimensional image of the internal tissue of the living body based on combining the plurality of extracted images.

The processor may be configured to execute the program of instructions to, prior to generating the three-dimensional image, generate a correction image from a portion of the light source or a portion of the sensor, and correct the plurality of extracted images using the correction image.

Three-dimensional images of internal tissues (e.g. blood vessel) located at a specific depth from skin may be clearly obtained.

BRIEF DESCRIPTION OF THE DRAWINGS

FIGS. 6A and 6B are graphs showing an example of a wavelength spectrum of a light source and a sensor of the bio imaging system shown in FIGS. 3 and 4 according to some example embodiments.

DETAILED DESCRIPTION

Figure 1:
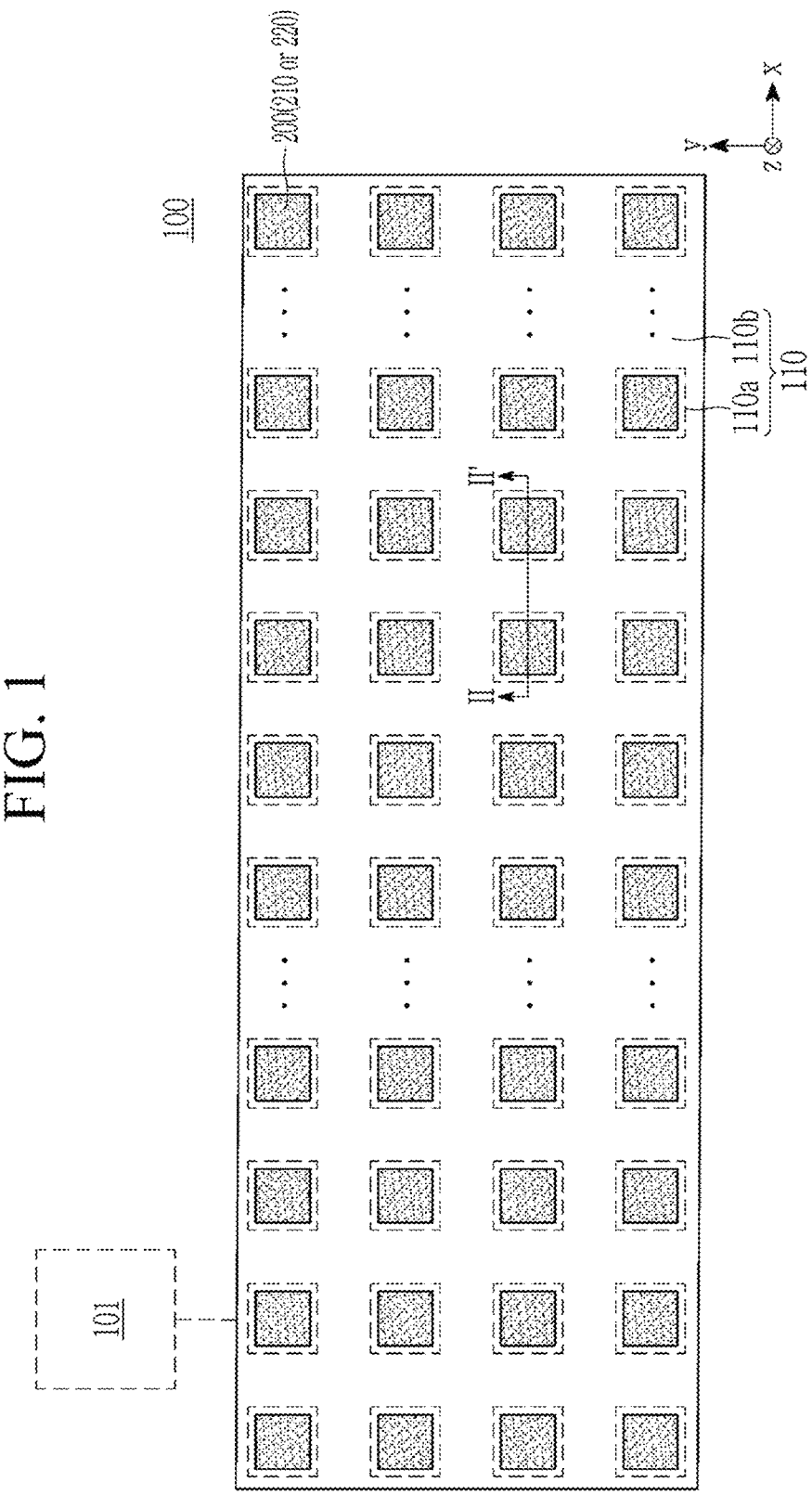
FIG. 1 is a plan view of a bio imaging system according to some example embodiments.

Hereinafter, some example embodiments are described in detail so that those skilled in the art can easily implement them. However, the actual applied structure may be implemented in various different forms and is not limited to the implementations described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, the "wavelength spectrum" may mean an emission spectrum, an absorption spectrum, or a transmission spectrum.

Hereinafter, a bio imaging system according to some example embodiments will be described.

A bio imaging system is an imaging device capable of providing spatial distribution information such as a location, shape, size, and/or thickness of an internal tissue of the living body such as a blood vessel.

Figure 2A:
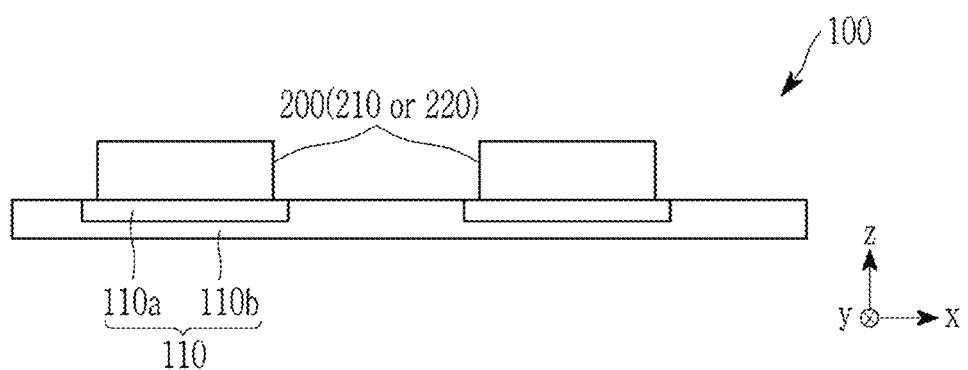
FIG. 2A is a cross-sectional view taken along line II-II' of the bio imaging system of FIG. 1 according to some example embodiments.
Figure 2B:
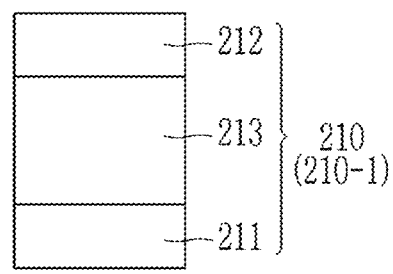
FIGS. 2B and 2C are cross-sectional views showing examples of the light source shown in FIGS. 1 and 2A according to some example embodiments.
Figure 2C:
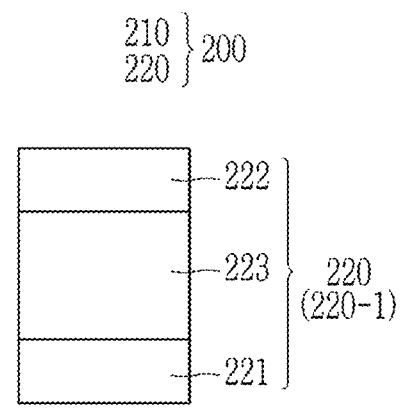

FIG. 1 is a plan view of a bio imaging system according to some example embodiments, FIG. 2A is a cross-sectional view taken along line II-II' of the bio imaging system of FIG. 1, and FIGS. 2B and 2C are cross-sectional views showing examples of the light source shown in FIGS. 1 and 2A.

The bio imaging system 100 according to some example embodiments includes a substrate 110 and a plurality of optoelectronic elements 200.

The substrate 110 may be under the plurality of optoelectronic elements 200 to support the plurality of optoelectronic elements 200. The substrate 110 may be in contact with a living body (e.g., skin) or close to a living body, and may have high light transmittance so that light emitted from the optoelectronic element 200 or flowing into the optoelectronic element 200 may pass. A light transmittance of the substrate 110 may be greater than or equal to about 70%, greater than or equal to about 75%, greater than or equal to about 80%, greater than or equal to about 85%, greater than or equal to about 90%, greater than or equal to about 95%, greater than or equal to about 97%, greater than or equal to about 98%, or greater than or equal to about 99%.

The substrate 110 may be a stretchable substrate. The stretchable substrate may respond flexibly to external forces or external movements such as twisting, pressing, and pulling, and may be easily restored to its original state.

The stretchable substrate may include a stretchable material such as an elastomer, and the stretchable material may include an organic elastomer, an organic/inorganic elastomer, an inorganic elastomer-like material, or a combination thereof. The organic elastomer or the organic/inorganic elastomer may be, for example, a substituted or unsubstituted polyorganosiloxane such as polydimethylsiloxane, an elastomer including substituted or unsubstituted butadiene moiety such as styrene-ethylene-butylene-styrene, an elastomer including a urethane moiety, an elastomer including an acrylic moiety, an elastomer including an olefin moiety, or a combination thereof, but is not limited thereto. The inorganic elastomer-like material may include a ceramic having elasticity, a solid metal, a liquid metal, or a combination thereof, but is not limited thereto.

The substrate 110 may include regions having different stiffness in relation to each other, for example, a rigid region 110a having relatively high stiffness and a soft region 110b having a relatively low stiffness. Herein, the stiffness indicates a degree of resistance to deformation when a force is applied from the outside. Relatively high stiffness means that the resistance to deformation is relatively large, so that deformation is small while relatively low stiffness means that the resistance to deformation is relatively small, so that the deformation is large.

The stiffness may be evaluated from an elastic modulus, and a high elastic modulus may mean high stiffness and a low elastic modulus may mean low stiffness. The elastic modulus may be, for example, a Young's modulus. A difference between elastic moduli of the rigid region 110a and the soft region 110b of the substrate 110 may be about 100 times or more, and the elastic modulus of the rigid region 110a may be about 100 times higher than the elastic modulus of the soft region 110b. The difference between the elastic modulus of the rigid region 110a and the soft region 110b may be about 100 to 100,000 times within the above range, and the elastic modulus of the rigid region 110a may be about 100 times to about 100,000 times higher than the elastic modulus of the soft region 110b, but is not limited thereto. For example, the elastic modulus of the rigid region 110a may be about $10^7$ Pa to about $10^{12}$ Pa, and the elastic modulus of the soft region 110b may be greater than or equal to about 10 Pa and less than about $10^7$ Pa, but is not limited thereto.

Elongation rates of the rigid region 110a and the soft region 110b of the substrate 110 may be different due to the aforementioned difference in stiffness, and the elongation rate of the soft region 110b may be higher than the elongation rate of the rigid region 110a. Herein, the elongation rate may be a percentage of the length change that is increased to a breaking point with respect to the initial length. For example, the elongation rate of the rigid region 110a of the substrate 110 may be less than or equal to about 5%, within the range, about 0% to about 5%, about 0% to about 4%, about 0% to about 3%, about 0% to about 2%, about 0% to about 1%, about 0.5% to about 5%, about 0.5% to about 4%, about 0.5% to about 3%, about 0.5% to about 2%, or about 1% to about 2%. For example, the elongation rate of the soft region 110b of the substrate 110 may be greater than or equal to about 10%, within the range, about 10% to about 300%, about 10% to about 200%, about 10% to about 100%, about 10% to about 90%, about 10% to about 80%, about 10% to about 70%, about 10% to about 60%, about 10% to about 50%, about 10% to about 40%, about 20% to about 70%, about 20% to about 60%, about 20% to about 50%, or about 20% to about 40%.

A plurality of rigid regions 110a of the substrate 110 may have an island-shape separated from each other (e.g., isolated from direct contact with each other), and the optoelectronic elements 200 which are described later may be on each rigid region 110a of the substrate 110. The soft region 110b of the substrate 110 may be a region other than the plurality of first regions 110a and may be continuously connected thereto. The soft region 110b of the substrate 110 may provide stretchability and due to its relatively low stiffness and high elongation rate, it may flexibly respond to external forces or external movements such as twisting and pulling, and may be easily restored to its original state.

A plurality of optoelectronic elements 200 are on the substrate 110. The plurality of optoelectronic elements 200 may be regularly or randomly arranged on the substrate 110, for example, may be arranged in parallel along an in-plane direction (e.g., x direction, y direction, or xy direction) of the substrate 110. For example, the optoelectronic elements 200 may be arranged along rows and/or columns to form an array. For example, each optoelectronic element 200 may be on the rigid region 110a of the substrate 110.

In the drawings, the shape, size, and number of the optoelectronic elements 200 are illustrated as an example, but the shape, size, and number of the optoelectronic elements 200 may be variously changed. For example, the optoelectronic elements 200 may have a size (dimension) of several to hundreds of micrometers. For example, the optoelectronic elements 200 may each independently have a width, length, and thickness of greater than or equal to about 1 μm and less than 1000 μm, and within the range, may have a width, length, and thickness of about 10 μm to about 800 μm, about 10 μm to about 700 μm, about 10 μm to about 600 μm, or about 10 μm to about 500 μm, but is not limited thereto. For example, the number of optoelectronic elements 200 may be 4 or more, for example, 4 to 1000, 4 to 800, or 4 to 600, but is not limited thereto.

Each optoelectronic element 200 may be a light source 210 configured to emit light or a sensor 220 configured to absorb light and to convert the absorbed light into an electrical signal. For example, some of the plurality of optoelectronic elements 200 may be the light source 210 and some of the plurality of optoelectronic elements 200 may be the sensor 220. The number (e.g., quantity) of light sources 210 and sensors 220 may be the same as or different from each other.

The light source 210 may supply light to internal tissues of a living body through the skin, and the light may belong to visible to infrared wavelength spectra, but is not limited thereto.

The light source 210 may include, for example, a light emitting element 210-1 such as an inorganic light emitting diode, an organic light emitting diode, or a micro light emitting diode. The light emitting element 210-1 may include, for example, a pair of electrodes 211 and 212 facing each other and a light emitting layer 213 between the pair of electrodes 211 and 212.

At least one of the pair of electrodes 211 or 212 may be a light-transmitting electrode. For example, one of the pair of electrodes 211 or 212 may be a light-transmitting electrode and the other may be a reflective electrode. For example, an electrode close to the substrate 110 may be a light-transmitting electrode. One of the pair of electrodes 211 or 212 may be an anode and the other may be a cathode. For example, the pair of electrodes 211 and 212 may be stretchable electrodes, and the stretchable electrodes may include, for example, a stretchable conductor, or may have a stretchable shape such as a wavy, wrinkled, pop-up, or non-planar mesh shape.

The light emitting layer 213 may include an organic light emitting material, an inorganic light emitting material, a light emitting material such as quantum dot and/or perovskite, but is not limited thereto. The emission spectrum of the light emitting layer 213 may belong to a visible to infrared wavelength spectra, and may include, for example, a blue wavelength spectrum, a green wavelength spectrum, a red wavelength spectrum, a (near) infrared wavelength spectrum, or a combination thereof. For example, the light emitting layer 213 may be a stretchable light emitting layer. As an example, the light emitting element 210-1 may be a stretchable element.

The sensor 220 may be configured to absorb (e.g., selectively absorb) light supplied from the light source 210 and reflected by internal tissue of a living body (e.g., blood vessels), and may convert the absorbed light into an electrical signal.

The sensor 220 may include, for example, a light absorption element 220-1 such as an organic or inorganic diode. The light absorption element 220-1 may include, for example, a pair of electrodes 221 and 222 facing each other and a light absorption layer 223 between the pair of electrodes 221 and 222. At least one of the pair of electrodes 221 or 222 may be a light-transmitting electrode. For example, one of the pair of electrodes 221 or 222 may be a light-transmitting electrode and the other may be a reflective electrode. For example, an electrode close to the substrate 110 may be a light-transmitting electrode. One of the pair of electrodes 221 or 222 may be an anode and the other may be a cathode. For example, the pair of electrodes 221 and 222 may be a stretchable electrode, and the stretchable electrode may include, for example, a stretchable conductor or have a stretchable shape such as a wavy shape, a corrugated shape, a pop-up shape, or a non-planar mesh shape.

The light absorption layer 223 may be a photoelectric conversion layer configured to absorb light of a particular (or, alternatively, predetermined) wavelength spectrum, and to convert the absorbed light into an electrical signal. Accordingly, a sensor 220 may be referred to as being configured to generate an electrical signal (which may be referred to herein as a signal) based on absorbing light, including absorbing light of a particular wavelength spectrum. The light absorption layer 223 may include, for example, an inorganic light absorbing semiconductor, an organic light absorbing semiconductor, and/or an organic-inorganic light absorbing semiconductor. For example, the inorganic light absorbing semiconductor, organic light absorbing semiconductor and/or organic-inorganic light absorbing semiconductor may be a p-type semiconductor and/or an n-type semiconductor forming a pn junction. The absorption spectrum of the light absorption layer 223 may belong to visible to infrared wavelength spectra, and may include, for example, a blue wavelength spectrum, a green wavelength spectrum, a red wavelength spectrum, a (near) infrared wavelength spectrum, or a combination thereof. For example, the light absorption layer 223 may be a stretchable light absorption layer. For example, the light absorption element 220-1 may be a stretchable element.

At least one of the light source 210 or the sensor 220 may be configured to emit or absorb light of different wavelength spectra. For example, the bio imaging system 100 may include a light source 210 that is configured to emit light of different wavelength spectra, a sensor 220 that is configured to absorb light of different wavelength spectra, or both a light source 210 that is configured to emit light of different wavelength spectra and a sensor 220 that is configured to absorb light of different wavelength spectra.

The bio imaging system 100 (and/or an electronic device in which the bio imaging system 100 is included) may be configured to combine a plurality of images obtained by light of different wavelength spectra to obtain a three-dimensional image of an internal tissue of a living body (e.g., blood vessels). For example, as shown, the bio imaging system 100 may include a controller 101 that is communicatively and/or electrically coupled to the light source 210 and the sensor 220 via a conductive path, including one or more conductive materials, conductive layers, wires, or the like. The controller 101 may be configured to control operation of the light source 210 and/or the sensor 220 (e.g., based on generating and transmitting signals to the light source 210 and/or sensor 220 via a conductive path, wire, or the like) to cause the light source 210 to emit light and/or to cause the sensor 220 to absorb light. The sensor 220 may be configured to generate signals based on absorbing light, and the bio imaging system 100 may be configured to transmit such signals from the sensor 220 to the controller 101 (e.g., via a conductive line, wire, bus, or the like). The sensor 220 may be configured to generate signals based on absorbing light, and the bio imaging system 100 may be configured to communicate such signals to the controller 101, independently of any control of the sensor 220 by the controller 101. The controller 101 may be configured to process the signals to generate (e.g., obtain) one or more images, such that the controller 101 of the bio imaging system 100 may be configured to obtain (e.g., generate) images based on light of various (e.g., different) wavelength spectra (e.g., based on the sensor 220 generating various signals based on light of various wavelength spectra being absorbed by one or more portions of the sensor 220, and said signals being received and processed by the controller 101 to generate the images).

Figure 34:
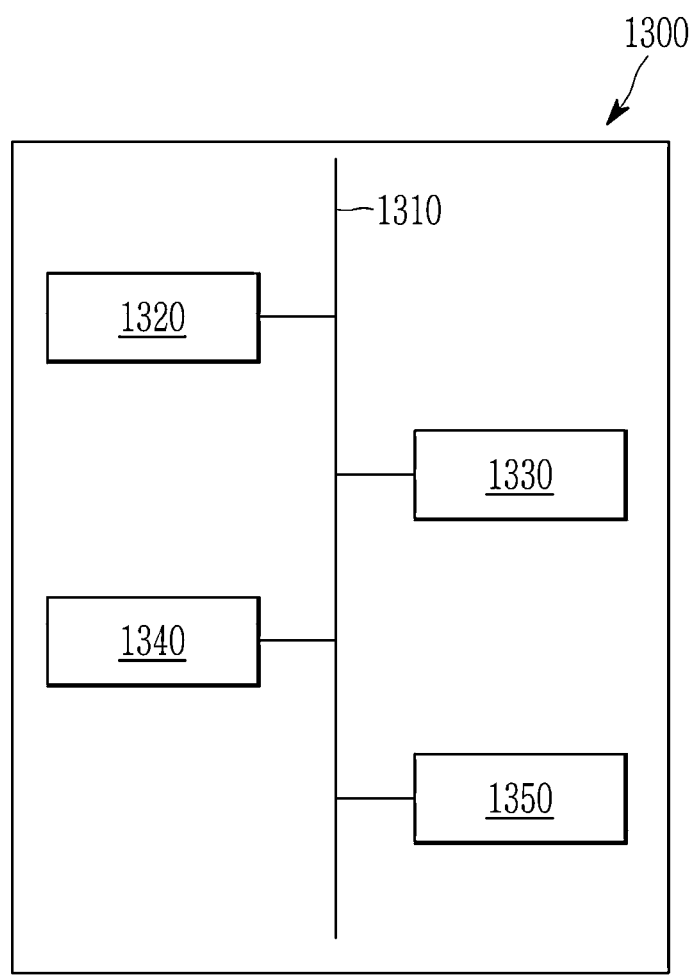
FIG. 34 is a schematic diagram of an electronic device according to some example embodiments.

It will be understood that the controller 101 may be implemented by one or more instances of processing circuitry as described herein (e.g., as described with reference to FIG. 34) and may include, may be included in, and/or may be implemented by one or more devices as described herein, (e.g., the controller 101 may include processor 1320 of FIG. 34 and memory 1330 of FIG. 34, and/or any functionality of the bio imaging system 100 and/or the controller 101 may be implemented based on processor 1320 of FIG. 34 executing a program of instructions stored in memory 1330 of FIG. 34).

Where the bio imaging system 100 is described herein as performing an operation and/or being configured to perform an operation (e.g., combining a plurality of images obtained based on the light of different wavelength spectra to obtain a three-dimensional image of an internal tissue of a living body), it will be understood that the bio imaging system 100 may include one or more instances of processing circuitry (e.g., a processor executing a program of instructions stored in a memory to implement the functionality of the controller 101) that are configured to operate to cause the bio imaging system 100 to perform the operation and/or to be configured to perform the operation. Such operations that the controller 101 may be configured to perform (e.g., based on a processor such as a CPU of the controller 101 executing a program of instructions stored in a memory such as a SSD of the controller 101) may include generating signals to control operation of the light source 210, for example to cause the light source 210 (e.g., one or more light emitting elements of the light source) to emit light. Such operations that the controller 101 may be configured to perform may include processing signals generated by the sensor 220, for example one or more sensors of the sensor 220, based on the sensor 220 absorbing light, and received at the controller 101 from the sensor 220 to generate (e.g., obtain) one or more images, including images that are obtained based on the light of different wavelength spectra. Such operations that the controller 101 may be configured to perform may include processing signals and/or images to extract differences between a plurality of images to obtain a plurality of extracted images of an internal tissue of a living body according to a depth from skin surface. Such operations that the controller 101 may be configured to perform may include processing a plurality of extracted images to combine the plurality of extracted images to obtain a three-dimensional image of the internal tissue of the living body. Such operations that the controller 101 may be configured to perform may include controlling the light source 210 and/or the sensor 220 to obtain a correction image from a portion of the light source 210 or a portion of the sensor 220, correcting the plurality of extracted images using the correction image; obtaining the three-dimensional image based on the corrected extracted images.

In some example embodiments, the controller 101 may be part of a separate bio imaging system that is external to the bio imaging system 100, where the controller 101 may control at least one of the light source 210 or the sensor 220 and may be configured to receive signals from the sensor 220 based on the sensor 220 absorbing light, where the controller 101 may process the signals to obtain images and to perform any methods as described herein with regard to obtaining and/or extracting images, including three-dimensional images.

The light source 210 may include a plurality of light sources configured to emit light of different wavelength spectra in relation to each other.

The sensor 220 may include a plurality of sensors configured to absorb light of different wavelength spectra in relation to each other.

The light source 210 may include a plurality of light sources configured to emit light of different wavelength spectra in relation to each other, and the sensor 220 may include a plurality of sensors configured to absorb light of different wavelength spectra in relation to each other.

Hereinafter, examples of the bio imaging system 100 shown in FIGS. 1, 2A, 2B, and 2C will be described with reference to FIGS. 3 to 6B.

Figure 3:
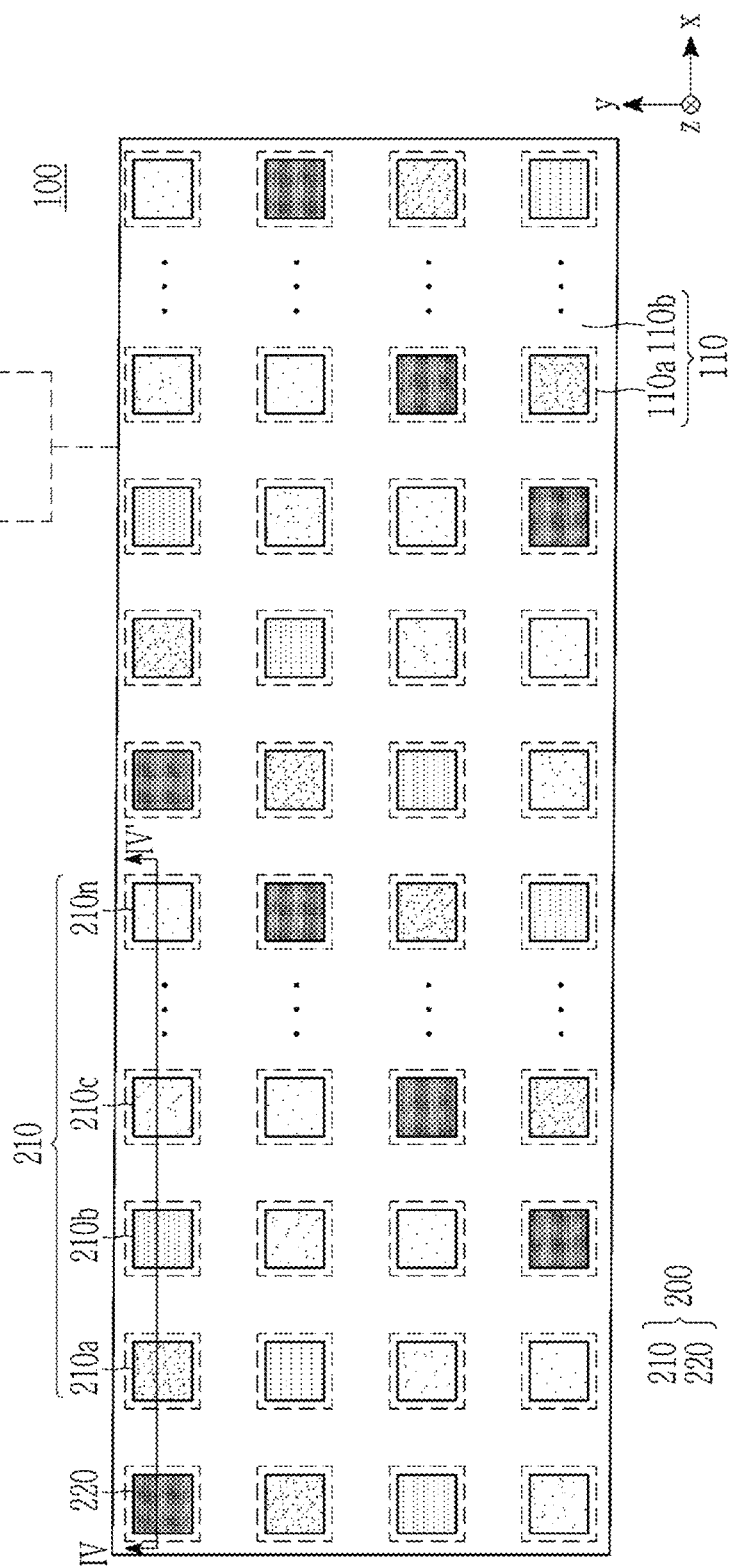
FIG. 3 is a plan view showing an example of the bio imaging system shown in FIGS. 1 and 2A to 2C according to some example embodiments.
Figure 4:
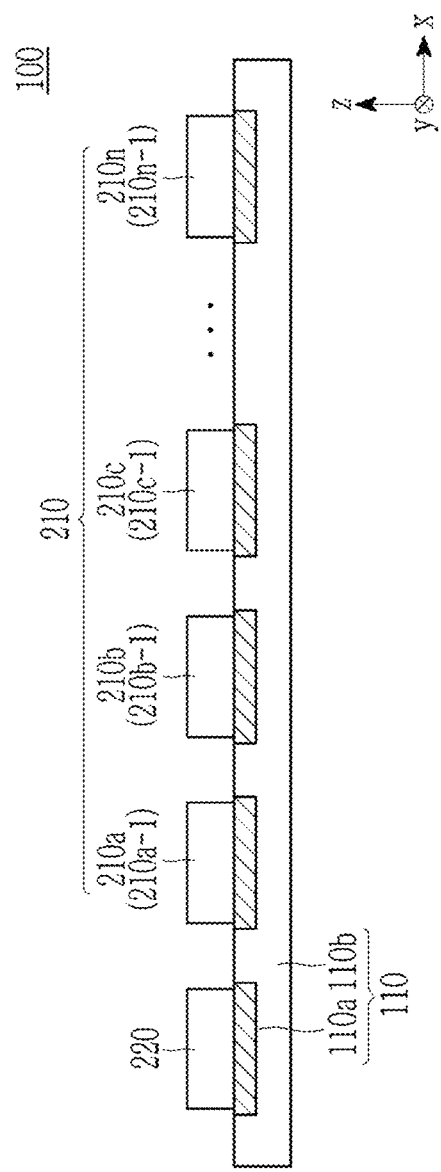
FIG. 4 is a cross-sectional view taken along line IV-IV' of an example of the bio imaging system of FIG. 3 according to some example embodiments.
Figure 5A:
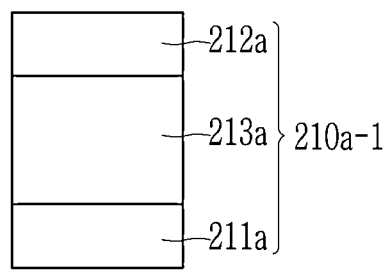
FIGS. 5A, 5B, 5C, and 5D are cross-sectional views showing examples of the light source shown in FIGS. 3 and 4 according to some example embodiments.
Figure 5B:
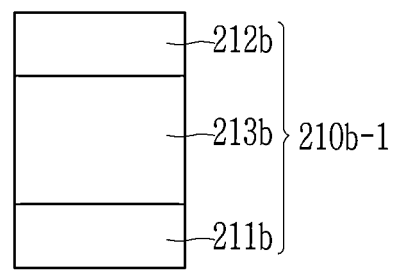
Figure 5C:
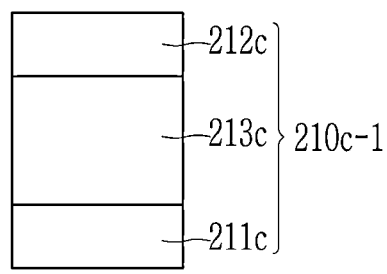
Figure 5D:
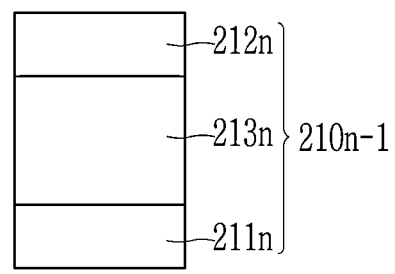

FIG. 3 is a plan view showing an example of the bio imaging system shown in FIGS. 1 and 2A to 2C, FIG. 4 is a cross-sectional view taken along line IV-IV' of an example of the bio imaging system of FIG. 3, FIGS. 5A and 5B are cross-sectional views showing examples of the light source shown in FIGS. 3 and 4, and FIGS. 6A and 6B are graphs showing an example of a wavelength spectrum of a light source and a sensor of the bio imaging system shown in FIGS. 3 and 4.

Referring to FIGS. 3 and 4, a bio imaging system 100 according to some example embodiments includes a substrate 110; a plurality of light sources 210 arranged on the substrate 110 and configured to emit light of different wavelength spectra in relation to each other; and a plurality of sensors 220 arranged on the substrate 110. As described above, the plurality of light sources 210 and the plurality of sensors 220 may be on the rigid region 110a of the substrate 110.

The light source 210 includes a first light source 210a, a second light source 210b, and a third light source 210c that are separated from each other (e.g., isolated from direct contact with each other). The light source 210 may additionally include an $n^{th}$ light source 210n in addition to the first light source 210a, the second light source 210b, and the third light source 210c, where n may be an integer of 4 to 10. The $n^{th}$ light source 210n does not mean one light source, but an $n^{th}$ light source. For example, when n is 7, the light source 210 may further include fourth, fifth, sixth, and seventh light sources in addition to the first light source 210a, second light source 210b, and third light source 210c. The $n^{th}$ light source 210n may be omitted.

As shown, the first light source 210a, the second light source 210b, the third light source 210c, and the $n^{th}$ light source 210n are arranged in parallel (e.g., may extend in a linear sequence) along an in-plane direction of the substrate 110 (e.g., x direction, y direction, or xy direction) and light of different emission spectra in relation to each other within the visible to infrared wavelength spectra may be emitted. Restated, the first light source 210a, the second light source 210b, the third light source 210c, and the $n^{th}$ light source 210n may be configured to emit light of different emission spectra. Said different emission spectra may be within the visible to infrared wavelength spectra. For example, the first light source 210a, the second light source 210b, the third light source 210c, and the $n^{th}$ light source 210n may be configured to each emit light of different wavelength spectra in relation to each other within a wavelength range (e.g., wavelength spectrum) of about 380 nm to about 3 μm and a plurality of images obtained by light of different emission spectra in relation to each other may be combined to obtain a three-dimensional image of an internal tissue of a living body.

It will be understood, as described herein, that an in-plane direction of the substrate 110 (e.g., x direction, y direction, or xy direction) may extend in parallel to an upper surface of the substrate 110 and thus may be referred to interchangeably as a direction extending in parallel to the upper surface of the substrate 110. Additionally, a direction extending perpendicular to the in-plane direction (e.g., the z direction, which extends perpendicular to the x direction, y direction, or xy direction) may be referred to interchangeably herein as a direction extending perpendicular to the upper surface of the substrate 110.

The first light source 210a, the second light source 210b, the third light source 210c, and the n$^{th}$ light source 210n may respectively include a first light emitting element 210a-1, a second light emitting element 210b-1, a third light emitting element 210c-1, and an n$^{th}$ light emitting element 210n-1 which are configured to emit light of different emission spectra in relation to each other. That is, the first light source 210a may include the first light emitting element 210a-1, the second light source 210b may include the second light emitting element 210b-1, the third light source 210c may include the third light emitting element 210c-1, and the n$^{th}$ light source 210n may include the n$^{th}$ light emitting element 210n-1. Each of the first, second, third, and n$^{th}$ light emitting elements 210a-1, 210b-1, 210c-1, and 210n-1 may be an inorganic light emitting diode, an organic light emitting diode, or a micro light emitting diode. The light emitting characteristics of the first, second, third and n$^{th}$ light sources 210a, 210b, 210c, and 210n may be the same or substantially the same as the light emission characteristics of the first, second, third, and n$^{th}$ light emitting elements 210a-1, 210b-1, 210c-1, and 210n-1.

Referring to FIGS. 5A to 5D, the first light emitting element 210a-1 may include a pair of electrodes 211a and 212a facing each other and a light emitting layer 213a between a pair of electrodes 211a and 212a, the second light emitting element 210b-1 may include a pair of electrodes 211b and 212b facing each other and a light emitting layer 213b between the pair of electrodes 211b and 212b, the third light emitting element 210c-1 may include a pair of electrodes 211c and 212c facing each other and a light emitting layer 213c between the pair of electrodes 211c and 212c, and the n$^{th}$ light emitting element 210n-1 may include a pair of electrodes 211n and 212n facing each other and a light emitting layer 213n between the pair of electrodes 211n and 212n. The descriptions of the pair of electrodes 211 and 212 and the light emitting layer 213 are as described above.

The emission spectra of the light emitted from the first light emitting element 210a-1, the second light emitting element 210b-1, the third light emitting element 210c-1, and the n$^{th}$ light emitting element 210n-1 may be determined by the light emitting layers 213a, 213b, 213c, and 213n, and the light emitting layers 213a, 213b, 213c, and 213n may be configured to emit light of different emission spectra in relation to each other. For example, each of the first light emitting element 210a-1, the second light emitting element 210b-1, the third light emitting element 210c-1, and the n$^{th}$ light emitting element 210n-1 may be configured to emit light of a first emission spectrum having a first maximum emission wavelength $\lambda_{E1,max}$, a second emission spectrum having a second maximum emission wavelength $\lambda_{E2,max}$, a third emission spectrum having a third maximum emission wavelength $\lambda_{E3,max}$, and an n$^{th}$ emission spectrum having an n$^{th}$ maximum emission wavelength $\lambda_{En,max}$, wherein the first maximum emission wavelength $\lambda_{E1,max}$, the second maximum emission wavelength $\lambda_{E2,max}$, the third maximum emission wavelength $\lambda_{E3,max}$, and the n$^{th}$ maximum emission wavelength $\lambda_{En,max}$ may be different from each other.

The sensor 220 may be adjacent to at least a portion of the first, second, third, and n$^{th}$ light sources 210a, 210b, 210c, and 210n, and as shown in FIG. 2C, the sensor 220 may include a light absorption element 220-1 including a pair of electrodes 221 and 222 facing each other and a light absorption layer 223 between the pair of electrodes 221 and 222. The light absorption characteristics of the sensor 220 may be the same or substantially the same as the absorption characteristics of the light absorption layer 223, and the absorption spectrum of the sensor 220 may include light of all emission spectra emitted from the light source 210.

Referring to FIGS. 6A and 6B with FIGS. 5A to 5D, the first light emitting element 210a-1 may be configured to emit light of a first emission spectrum $SP_{E1}$ having a first maximum emission wavelength $\lambda_{E1,max}$, the second light emitting element 210b-1 may be configured to emit light of a second emission spectrum $SP_{E2}$ having a second maximum emission wavelength $\lambda_{E2,max}$, the third light emitting element 210c-1 may be configured to emit light of a third emission spectrum $SP_{E3}$ having a third maximum emission wavelength $\lambda_{E3,max}$, and the n$^{th}$ light emitting element 210n-1 may be configured to emit light of an emission spectrum $SP_{En}$ having an n$^{th}$ maximum emission wavelength $\lambda_{En,max}$. That is, the light emitting layer 213a may be configured to emit light of the first emission spectrum $SP_{E1}$ having the first maximum emission wavelength $\lambda_{E1,max}$, the light emitting layer 213b may be configured to emit light of the second emission spectrum $SP_{E2}$ having the second maximum emission wavelength $\lambda_{E2,max}$, the light emitting layer 213c may be configured to emit light of the third emission spectrum $SP_{E3}$ having the third maximum emission wavelength $\lambda_{E3,max}$, and the light emitting layer 213n may be configured to emit light of the emission spectrum having the n$^{th}$ maximum emission wavelength $\lambda_{En,max}$.

The second maximum emission wavelength $\lambda_{E2,max}$ may be a longer wavelength than the first maximum emission wavelength $\lambda_{E1,max}$, the third maximum emission wavelength $\lambda_{E3,max}$ may be a longer wavelength than the second maximum emission wavelength $\lambda_{E2,max}$, and the n$^{th}$ maximum emission wavelength $\lambda_{En,max}$ may be a longer wavelength than the third maximum emission wavelength $\lambda_{E3,max}$. The first maximum emission wavelength $\lambda_{E1,max}$, the second maximum emission wavelength $\lambda_{E2,max}$, the third maximum emission wavelength $\lambda_{E3,max}$, and the n$^{th}$ maximum emission wavelength $\lambda_{En,max}$ may be separated by a particular (or, alternatively, predetermined) interval. For example, each difference between two adjacent wavelengths of the first maximum emission wavelength $\lambda_{E1,max}$, the second maximum emission wavelength $\lambda_{E2,max}$, the third maximum emission wavelength $\lambda_{E3,max}$, and the n$^{th}$ maximum emission wavelength $\lambda_{En,max}$ may be for example greater than or equal to about 10 nm, within the above range, greater than or equal to about 15 nm, greater than or equal to about 20 nm, greater than or equal to about 30 nm, greater than or equal to about 40 nm, or greater than or equal to about 50 nm, within the above range, about 10 nm to about 500 nm, about 15 nm to about 500 nm, about 20 nm to about 500 nm, about 30 nm to about 500 nm, about 40 nm to about 500 nm, about 50 nm to about 500 nm, about 10 nm to about 300 nm, about 15 nm to about 300 nm, about 20 nm to about 300 nm, about 30 nm to about 300 nm, about 40 nm to about 300 nm or about 50 nm to about 300 nm.

The first maximum emission wavelength $\lambda_{E1,max}$, the second maximum emission wavelength $\lambda_{E2,max}$, the third maximum emission wavelength $\lambda_{E3,max}$, and the n$^{th}$ maximum emission wavelength $\lambda_{En,max}$ may belong to a visible to infrared wavelength spectra, and may be for example independently within about 380 nm to about 3 µm, about 400 nm to about 2 µm, about 450 nm to about 1500 nm, about 470 nm to about 1150 nm, about 480 nm to about 1100 nm, about 500 nm to about 1000 nm, about 550 nm to about 1000 nm, or about 600 nm to about 1000 nm. For example, the first maximum emission wavelength $\lambda_{E1,max}$, the second maximum emission wavelength $\lambda_{E2,max}$, the third maximum emission wavelength $\lambda_{E3,max}$, and the $n^{th}$ maximum emission wavelength $\lambda_{En,max}$ may each independently belong to one of a blue wavelength spectrum, a green wavelength spectrum, a red wavelength spectrum, or a (near) infrared wavelength spectrum, wherein the blue wavelength spectrum may be greater than or equal to about 400 nm and less than about 500 nm, the green wavelength spectrum may be greater than or equal to about 500 nm and less than or equal to about 600 nm, the red wavelength spectrum may be greater than about 600 nm and less than or equal to about 700 nm, and the (near) infrared wavelength spectrum may be greater than about 700 nm and less than or equal to about 3000 nm.

The full width at half maximum (FWHM) of the first, second, third, and $n^{th}$ emission spectra $SP_{E1}$, $SP_{E2}$, $SP_{E3}$, and $SP_{En}$ may be, for example, less than or equal to about 300 nm, and within the above range, about 10 nm to about 300 nm, about 30 nm to about 250 nm, or about 50 nm to about 200 nm.

Since the sensor 220 may detect light emitted from the first, second, third, and $n^{th}$ light sources 210a, 210b, 210c, and 210n and reflected by internal tissue of a living body (e.g., blood vessels), the absorption spectrum SPA of the sensor 220 may include light of all wavelength spectra emitted from the first, second, third, and $n^{th}$ light sources 210a, 210b, 210c, and 210n.

For example, the absorption spectrum of light detected by the sensor 220 may include all emission spectra of the first to $n^{th}$ light sources 210a, 210b, 210c, and 210n, and may be for example, within about 380 nm to about 3 µm, about 400 nm to about 2 µm, about 450 nm to about 1500 nm, about 470 nm to about 1150 nm, about 480 nm to about 1100 nm, about 500 nm to about 1000 nm, about 550 nm to about 1000 nm, or about 600 nm to about 1000 nm. For example, when the first, second, and third light sources 210a, 210b, and 210c emit light of a blue wavelength spectrum, a green wavelength spectrum and a red wavelength spectrum, respectively, the sensor 220 may detect light in a white wavelength spectrum including the blue wavelength spectrum, green wavelength spectrum, and red wavelength spectrum.

In the bio imaging system 100 according to some example embodiments, the plurality of light sources 210a, 210b, 210c, and 210n configured to emit light of different emission spectra in relation to each other may provide a plurality of images of an internal tissue of a living body according to the depth direction form the skin surface by using the difference in the penetration depth of light according to the wavelength (e.g., based on the sensor 220 absorbing light due to the plurality of light sources 210a, 210b, 210c, and 210n emitting light of different emission spectra in relation to each other and generating signals based on such absorbance that are processed by controller 101 to generate the plurality of images, for example based on controller 101 processing signals generated due to the sensor 220 absorbing light within a particular wavelength spectrum to generate a particular image associated with the particular wavelength spectrum). Such the plurality of images are combined (e.g., by the controller 101) to obtain information (e.g., properties of the internal tissues of the living body) such as a location, shape, size, and/or thickness of the internal tissues of the living body (e.g., blood vessels), and this information may be used to obtain spatial information of the internal tissues of the living body. In addition, this spatial information may be separated and/or extracted to effectively obtain information of the internal tissues of the living body present at a specific depth from the skin surface.

Specifically, when the skin is irradiated with light, the penetration depth of the light from the skin surface is different depending on a wavelength spectrum, and in general, light of a long wavelength spectrum may penetrate deeper than light of a short wavelength spectrum. On the other hand, since the light of the long wavelength spectrum may also be scattered, while it passes several tissues along the depth direction from the skin surface, information obtained from light of a particular (or, alternatively, predetermined) wavelength may not images of the internal tissues present at the maximum penetration depth but images of all the internal tissues of the living body within a penetration depth of the light. Accordingly, clear images of the internal tissues of the living body such as blood vessels present at a particular depth may be difficult to selectively obtain.

In some example embodiments, a plurality of light sources 210a, 210b, 210c, and 210n configured to emit light of different emission spectra and the sensor 220 configured to absorb the light reflected by the internal tissues of the living body by being irradiated from the plurality of light sources 210a, 210b, 210c, and 210n are arranged in the form of an array, and thereby different image information according to the penetration depth of light are combined to separate and/or extract image information of an internal body tissue along a depth direction from the skin surface, and to obtain image information of an internal tissue of a living body located at a specific depth.

For example, in the bio imaging system 100 shown in FIGS. 3 to 6B, when the first light source 210a is configured to emit light of the first emission spectrum $SP_{E1}$ having a first maximum emission wavelength $\lambda_{E1,max}$, which is a relatively short wavelength, the second light source 210b is configured to emit light of the second emission spectrum $SP_{E2}$ having a second maximum emission wavelength $\lambda_{E2,max}$ that is longer than the first maximum emission wavelength $\lambda_{E1,max}$, and the third light source 210c is configured to emit light of the third emission spectrum $SP_{E3}$ having a third maximum emission wavelength $\lambda_{E3,max}$ that is longer than the second maximum emission wavelength $\lambda_{E2,max}$, the light of the first emission spectrum $SP_{E1}$, second emission spectrum $SP_{E2}$ and third emission spectrum $SP_{E3}$ have different penetration depth of light from the skin surface, respectively, the light of the first emission spectrum $SP_{E1}$, second emission spectrum $SP_{E2}$ and third emission spectrum $SP_{E3}$ may pass through the skin, transmit by each maximum penetration depth, and be reflected by an internal tissue of a living body (e.g., blood vessels), and the reflected light may be absorbed and detected for each wavelength by the sensor 220.

At this time, no matter what distribution of the penetration depth of the light of the first emission spectrum $SP_{E1}$, the second emission spectrum $SP_{E2}$ and the third emission spectrum $SP_{E3}$ from the skin surface, the image obtained from irradiation of the third light source 210c configured to emit light of a relatively long wavelength emission spectrum may be an image at a position deeper than the image obtained from irradiation of the second light source 210b configured to emit light of a relatively short wavelength emission spectrum, and the image obtained from irradiation of the second light source 210b configured to emit light of a relatively long wavelength emission spectrum may be an image at a position deeper than the image obtained from irradiation of the first light source 210a configured to emit light of a relatively short wavelength emission spectrum. Therefore, by extracting the difference between the image obtained from the irradiation of the third light source 210c and the image obtained from the irradiation of the second light source 210b, image information at a depth at which only light of the third emission spectrum $SP_{E3}$ penetrates may be obtained, and by extracting the difference between the image obtained from the irradiation of the second light source 210b and the image obtained from the irradiation of the first light source 210a, image information at a depth at which only light of the second emission spectrum $SP_{E2}$ penetrates may be obtained. Accordingly, it is possible to effectively obtain image information of an internal tissue of a living body located at a specific depth from the skin surface.

In this way, the differences between (n−1) images obtained by selective irradiation of any two light sources among n light sources 210a, 210b, 210c, and 210n configured to emit light of different emission spectra in relation to each other are extracted and combined, and thereby, spatial information may be secured in the depth direction. The more the number of light sources, the more accurate spatial information may be secured in the depth direction.

One example of a bio imaging method using the aforementioned bio imaging system 100 may include fixing the bio imaging system 100 on the skin S of a living body; radiating light into the skin S by turning on the light source 210 (e.g., causing the light source 210 to emit light to irradiate the skin); and absorbing light passing the skin S and scattered and reflected by the internal tissues of the living body such as blood vessel BV by the sensor 220 (e.g., causing the sensor 220 to absorb light scattered and reflected by the internal tissue of the living body through the skin S) to obtain a plurality of images by the light of a wavelength spectrum different from each other (e.g., based on light of different wavelength spectra). The method may further include extracting the plurality of images of the internal tissues of the living body such as the blood vessel BV depending on a depth from the surface of the skin S (e.g., extracting differences between the obtained plurality of images to obtain a plurality of extracted images of the internal tissue of the living body according to a depth from the skin S surface); and combining the plurality of extracted images of the internal tissues of the living body such as the blood vessel BV to obtain a three-dimensional image of the internal tissues of the living body. The light source 210 may include first, second, third, and $n^{th}$ light sources 210a, 210b, 210c, and 210n configured to emit light of different emission spectra within visible to infrared wavelength spectra. The turning on of the light source 210 may include sequentially turning on the first, second, third, and $n^{th}$ light sources 210a, 210b, 210c, and 210n (e.g., causing the first, second, third, and $n^{th}$ light sources 210a, 210b, 210c, and 210n to sequentially emit light).

Figure 25:
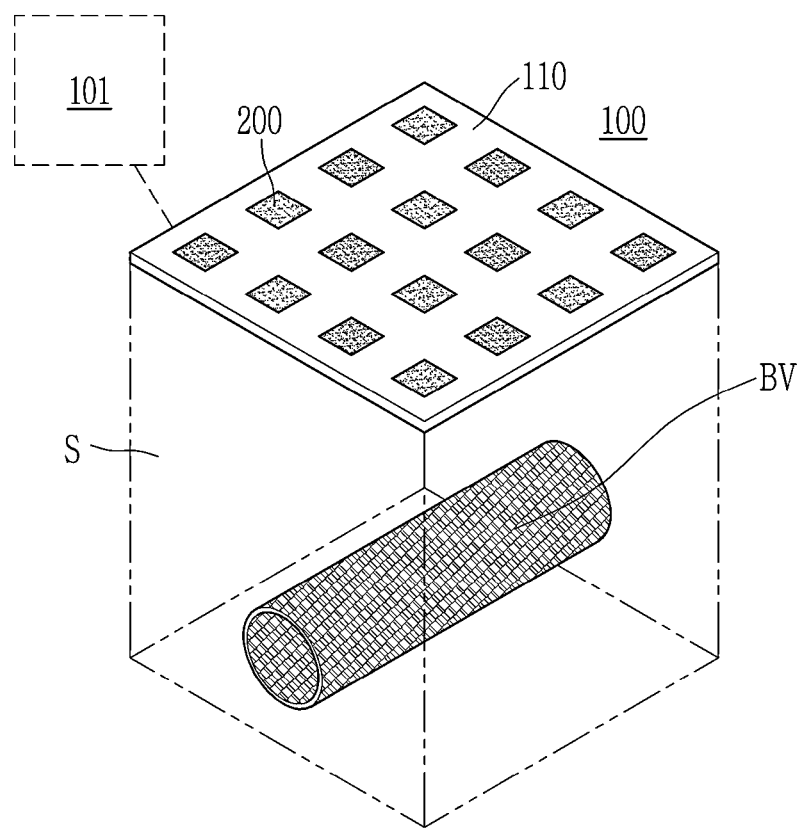
FIG. 25 is a schematic view showing an example of a method of obtaining image information of an internal tissue of a living body using a bio imaging system according to some example embodiments.
Figure 26:
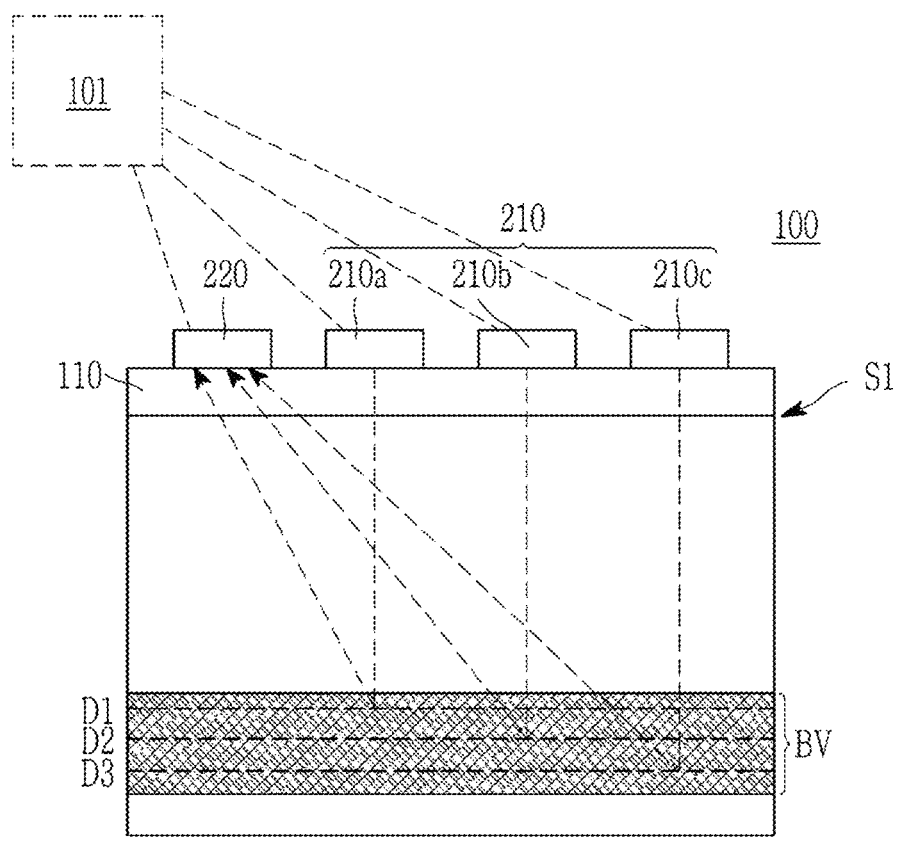
FIG. 26 is a schematic cross-sectional view showing an example of a method of obtaining image information of an internal tissue of a living body according to some example embodiments.

FIG. 25 is a schematic view showing an example of a method of obtaining image information of an internal tissue of a living body using a bio imaging system according to some example embodiments, FIG. 26 is a schematic cross-sectional view showing an example of a method of obtaining image information of an internal tissue of a living body using the bio imaging systems of FIGS. 3 to 6B, and FIGS. 27A and 27B are schematic views of obtaining a three-dimensional image by (e.g., based on) combining a plurality of images obtained by the methods of FIGS. 25 and 26.

As shown in FIG. 25, by fixing (attaching) the aforementioned bio imaging system 100 to the skin S, image information of internal tissue of a living body such as blood vessels BV may be obtained. Herein, as described above, when the first, second, third, and $n^{th}$ light sources 210a, 210b, 210c, and 210n of the bio imaging system 100 are sequentially turned on to irradiate light to the skin S, the penetration depth from the skin surface S1 may vary according to the emission spectrum of light, and light of a relatively long wavelength may penetrate deeper than light of a relatively short wavelength.

Figure 27A:
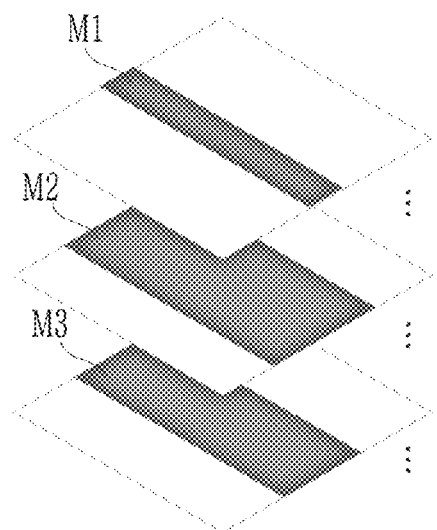
FIGS. 27A and 27B are schematic views of obtaining a three-dimensional image by combining a plurality of images obtained by the method of FIGS. 25 and 26 according to some example embodiments.
Figure 27B:
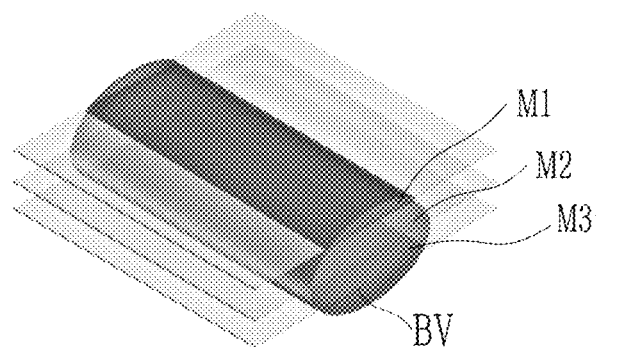

Accordingly, referring to FIGS. 26, 27A, and 27B, the depths $D_1$, $D_2$, and $D_3$ at which the light irradiated from the first, second and third light sources 210a, 210b, and 210c penetrate according to the wavelength have a particular (or, alternatively, predetermined) distribution, the light is reflected by different depths $D_1$, $D_2$, and $D_3$, and a plurality of planar (two-dimensional) images $M_1$, $M_2$, and $M_3$ according to the depths $D_1$, $D_2$, and $D_3$ of an internal tissue of a living body such as blood vessels BV depending on the wavelength may be obtained. For example, as described above, when among the first, second, and third light sources 210a, 210b, and 210c, the first light source 210a is configured to emit light of the first emission spectrum $SP_{E1}$ having the relatively shortest wavelength, and the third light source 210c is configured to emit light of the emission spectrum $SP_{E3}$ of the relatively longest wavelength, signals obtained by irradiation of light of the first to third emission spectrum $SP_{E1}$, $SP_{E2}$, and $SP_{E3}$ may provide images $M_1$, $M_2$, and $M_3$ from a relatively close depth $D_1$ to the deepest depth $D_3$ from the skin surface S1, sequentially. Based on these images $M_1$, $M_2$, and $M_3$, the image difference according to each depth $D_1$, $D_2$, and $D_3$ is extracted, and the lowest point, the middle point, and the highest point of the blood vessel BV are specified to obtain a three-dimensional image of the blood vessel BV. For example, differences between the images $M_1$, $M_2$, and $M_3$ may be extracted based on extracting a first image of an internal tissue of the living body located at a first depth $D_1$ from the skin S surface based on a difference between an image $M_2$ obtained based on turning on the second light source 210b and an image $M_1$ obtained based on turning on the first light source 210a, and extracting a second image of the internal tissue of the living body located at a second depth $D_2$ deeper than the first depth $D_1$ based on a difference between an image $M_3$ obtained based on turning on the third light source 210c and the image $M_2$ obtained based on turning on the second light source 210b.

Spatial information such as the location, shape, size and/or thickness of the blood vessel BV may be confirmed from the three-dimensional image of the blood vessel BV.

Figure 28:
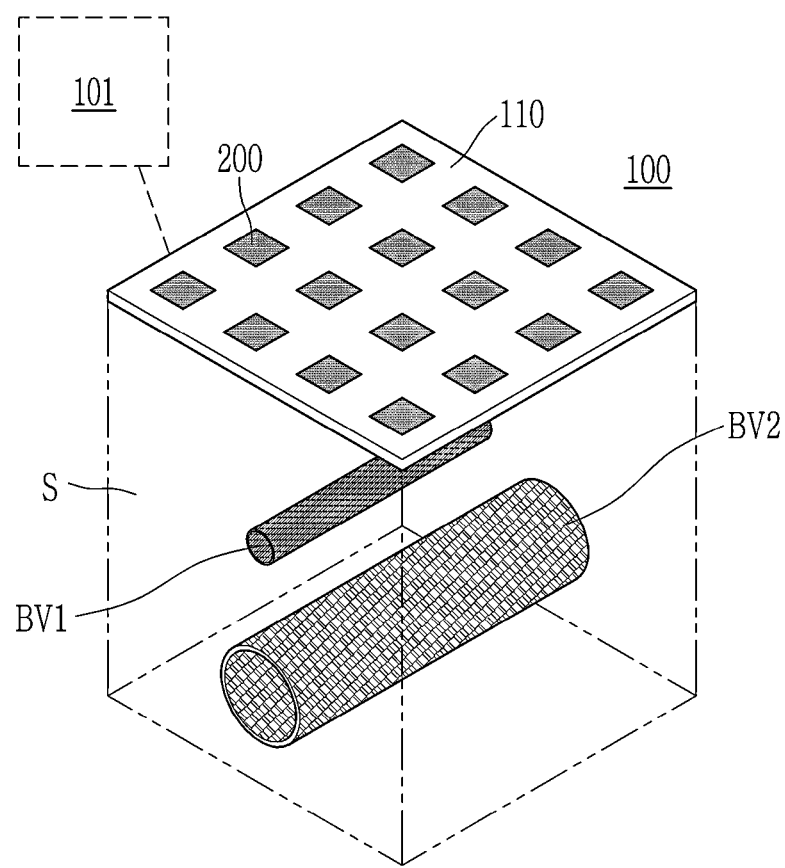
FIG. 28 is a schematic view showing an example of a method of obtaining image information of an internal tissue of a living body using a bio imaging system according to some example embodiments.
Figure 29:
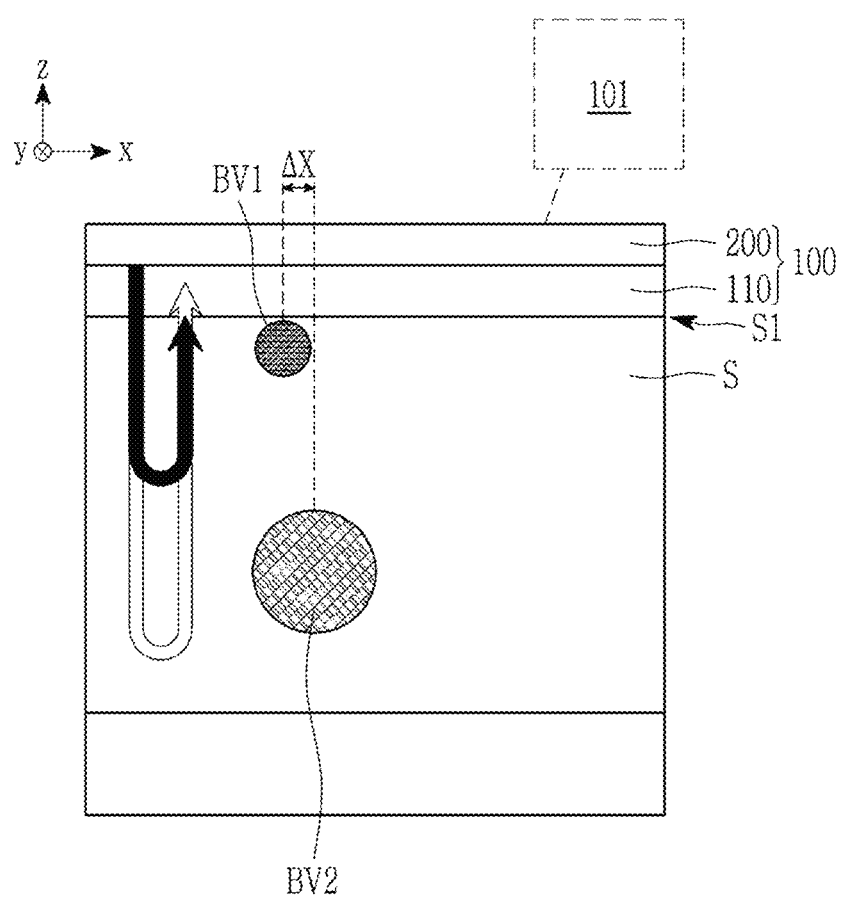
FIG. 29 is a schematic cross-sectional view showing an example of a method of obtaining image information of an internal tissue of a living body using the bio imaging system of FIG. 28 according to some example embodiments.

FIG. 28 is a schematic view showing an example of a method of obtaining image information of an internal tissue of a living body using a bio imaging system according to some example embodiments, and FIG. 29 is a schematic cross-sectional view showing an example of a method of obtaining image information of an internal tissue of a living body using the bio imaging system of FIGS. 3 to 6B.

In the present example, when a plurality of blood vessels BV1 and BV2 are located to be overlapped with each other in the depth direction, an image of a blood vessel BV located at a specific depth may be obtained by separating the images of the plurality of blood vessels BV and extracting the difference.

That is, the depths $D_1$, $D_2$, and $D_3$ at which the light irradiated from the first, second, and third light sources 210a, 210b, and 210c penetrate according to the wavelength have a particular (or, alternatively, predetermined) distribution, and a plurality of images of internal tissue of a living body such as blood vessels BV1 and BV2 reflected by different depths according to wavelength may be obtained. Image information obtained from light of the first to third emission spectrum $SP_{E1}$, $SP_{E2}$, and $SP_{E3}$ may include spatial information from a relatively close depth $D_1$ to the deepest depth $D_3$ from the skin surface S1, respectively, and it is possible not only to obtain a three-dimensional image of each blood vessel BV1 and BV2, by extracting the difference between the plurality of images and specifying the lowest point, the middle point, and the highest point of each blood vessel BV1 and BV2, but also to obtain a clear image of the blood vessel BV2 without reducing the resolution caused by the blood vessel BV1, by extracting the difference between the image obtained from the blood vessel BV2 and the image obtained from the blood vessel BV1. Therefore, when the plurality of blood vessels BV1 and BV2 are located in the depth direction from the skin surface S1, spatial information of the internal tissues of the living body may be effectively checked in this manner. Here, an example in which two blood vessels BV1 and BV2 are located in the depth direction has been described, but a case in which n blood vessels are located in the depth direction may also be described.

Meanwhile, the bio imaging method may further include obtaining a correction image before (e.g., prior to) obtaining the aforementioned three-dimensional image. The correction image may be for excluding an influence of the light characteristics (e.g., scattering and/or absorption) of the skin caused by differences in skin color and thickness of subcutaneous tissue for each individual, and may be obtained based on, for example, a point spread function. For example, the correction image may be obtained by turning on only some of the light sources 210 of the first position (specific position) of the bio imaging system 100 to obtain an image according to the wavelength spectrum of the first position corresponding to the turned on some of the light sources 210, turning on only some of the light sources 210 at the second position (specific position) of the bio imaging system 100 to obtain an image according to the wavelength spectrum of the second position corresponding to the turned on some light sources 210, and in this way, turning on only some of the light sources 210 at the $n^{th}$ position to obtain an image according to the wavelength spectrum of the $n^{th}$ position corresponding to the turned-on some of the light sources 210. The correction image may be applied to the plurality of extracted images to correct the plurality of extracted images. The corrected extracted images may then be combined to obtain the three-dimensional image. By correcting the aforementioned plurality of extracted images using the correction image, the effect of the optical characteristics of the skin may be excluded to obtain a clear three-dimensional image. Accordingly, a three-dimensional image of the internal tissue of the living body may be obtained based on combining the plurality of extracted images.

Hereinafter, another example of the bio imaging system 100 shown in FIGS. 1 to 2B will be described with reference to FIG. 7 along with FIGS. 3 to 6B.

Figure 7:
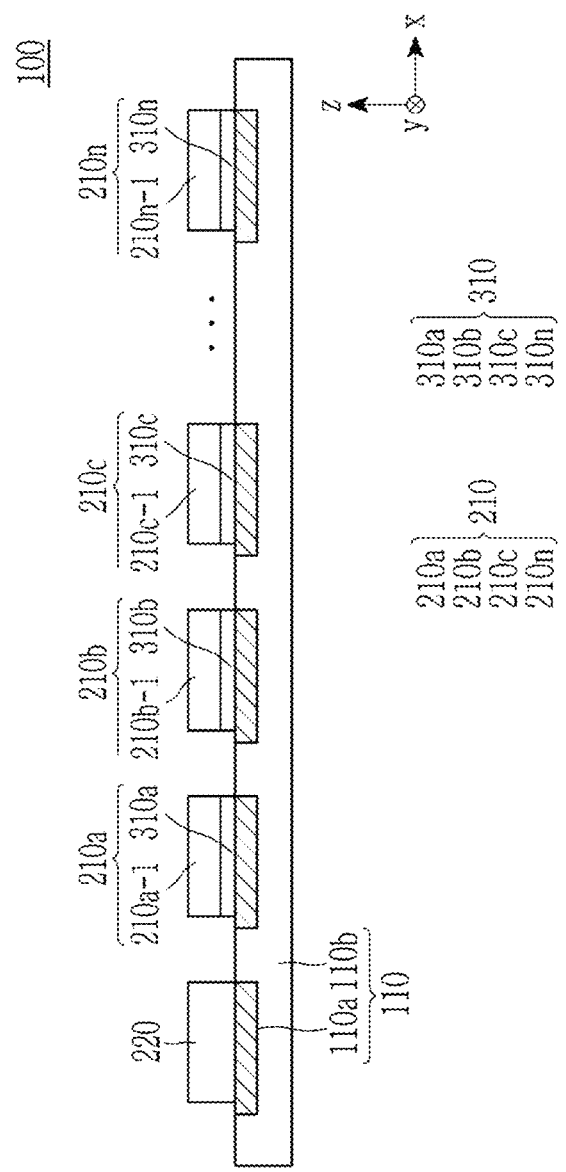
FIG. 7 is a cross-sectional view of another example of the bio imaging system of FIG. 3 taken along line IV-IV' according to some example embodiments.
Figure 8A:
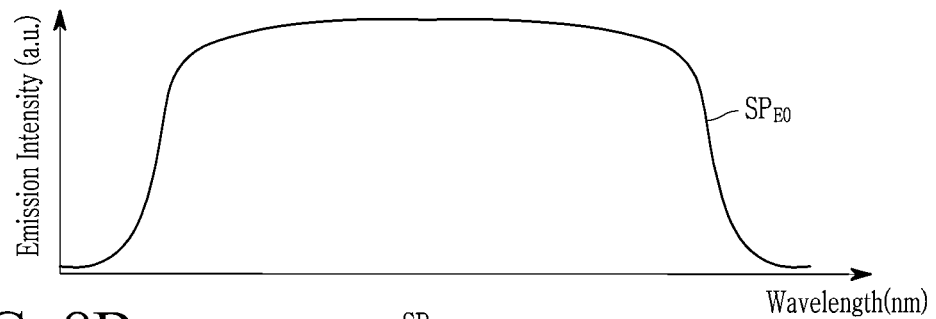
FIGS. 8A, 8B, 8C, and 8D are graphs showing examples of a wavelength spectrum of a light source and a sensor of the bio imaging system shown in FIGS. 3 and 7 according to some example embodiments.
Figure 8B:
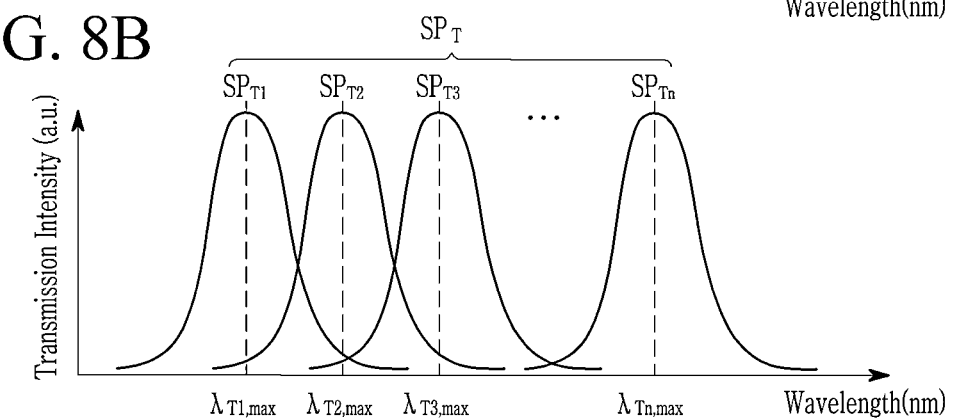
Figure 8C:
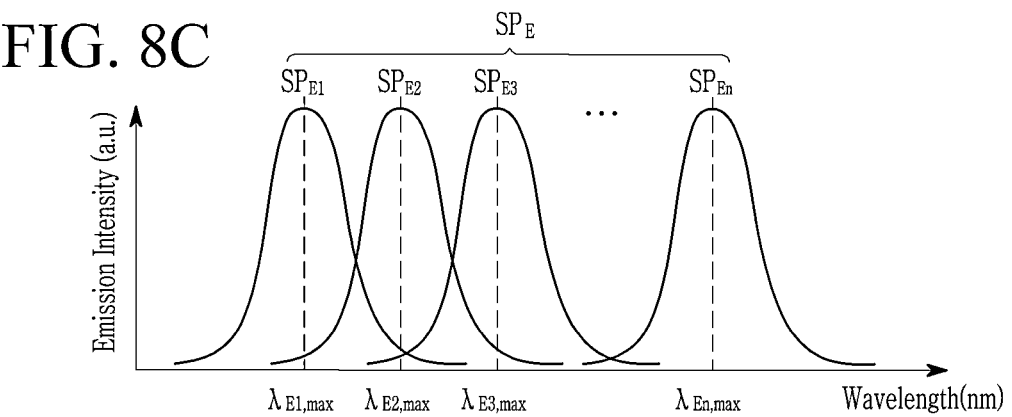
Figure 8D:
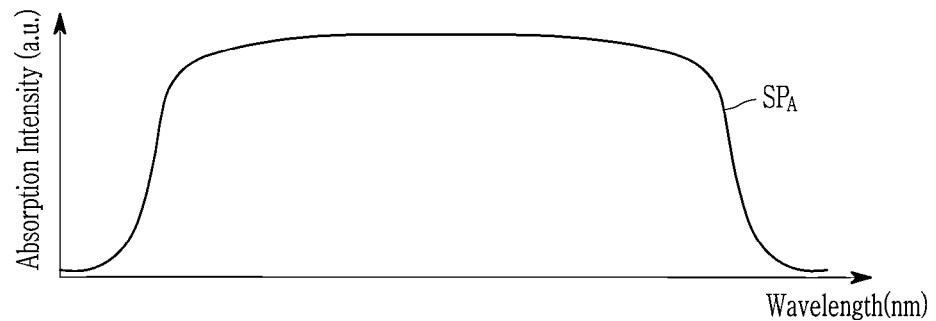

FIG. 7 is a cross-sectional view of another example of the bio imaging system of FIG. 3 taken along line IV-IV', and FIGS. 8A, 8B, 8C, and 8D are graphs showing an example of a wavelength spectrum of a light source and a sensor of the bio imaging system shown in FIGS. 3 and 7.

Referring to FIG. 7, a bio imaging system 100 according to some example embodiments includes a substrate 110; a plurality of light sources 210 arranged on the substrate 110; and a plurality of sensors 220 arranged on the substrate 110, and the light source 210 is separated from each other and includes a first light source 210a, a second light source 210b, and a third light source 210c and optionally an $n^{th}$ light source 210n which are configured to emit light of different wavelength spectrum, like the aforementioned example.

However, in the bio imaging system 100 according to the present example, the light source 210 may include first, second, third, and $n^{th}$ light sources 210a, 210b, 210c, and 210n that include a first light emitting element 210a-1, a second light emitting element 210b-1, a third light emitting element 210c-1, and an $n^{th}$ light emitting element 210n-1 which each is configured to emit light of a common emission spectrum (e.g., a same emission spectrum), and each of the first light source 210a, the second light source 210b, the third light source 210c, and the $n^{th}$ light source 210n may further include first, second, third, and $n^{th}$ color filters 310a, 310b, 310c, and 310n for color separation, unlike the bio imaging system 100 according to the aforementioned example. That is, the first light source 210a includes the first light emitting element 210a-1 and the first color filter 310a, the second light source 210b includes the second light emitting element 210b-1 and the second color filter 310b, the third light source 210c includes a third light emitting element 210c-1 and a third color filter 310c, and the $n^{th}$ light source 210n includes the $n^{th}$ light emitting element 210n-1 and an $n^{th}$ color filter 310n. For example, the first light emitting element 210a-1 may be configured to emit light of a first emission spectrum, the second light emitting element 210b-1 may be configured to emit light of a second emission spectrum, and the third light emitting element 210c-1 may be configured to emit light of a third emission spectrum, where the first, second, and third emission spectra are all a same (e.g., common) emission spectrum. As shown, the light source 210 may include a plurality of light emitting elements 210a-1 to 210n-1 that may be configured to emit light of a common emission spectrum (e.g., same emission spectrum), and the bio imaging system 100 may further include a plurality of color filters 310a to 310n that are overlapped with separate, respective (e.g., different) light emitting elements 210a-1 to 210n-1 in the z direction extending perpendicular to the in-plane direction of the substrate 110, where the plurality of color filters 310a to 310n are configured to provide wavelength selectivity to the common emission spectrum, for example based on different filters selectively transmitting different wavelength spectra in relation to each other, such that different color filters that are overlapped with different light emitting elements may cause different wavelength spectra of light, of the common emission spectrum of light emitted by the light emitting elements, to be selectively transmitted by the bio imaging system 100.

The first, second, third, and $n^{th}$ color filters 310a, 310b, 310c, and 310n may be respectively disposed at each position through which light emitted from the first light emitting element 210a-1, the second light emitting element 210b-1, the third light emitting element 210c-1, and the $n^{th}$ light emitting element 210n-1 pass and may be for example overlapped (e.g., in the z direction which extends perpendicular to the in-plane direction of the substrate 110 as shown) with the first light emitting element 210a-1, the second light emitting element 210b-1, the third light emitting element 210c-1, and the $n^{th}$ light emitting element 210n-1, respectively. The first light emitting element 210a-1 and the first color filter 310a, the second light emitting element 210b-1 and the second color filter 310b, the third light emitting element 210c-1 and the third color filter 310c, the n$^{th}$ light emitting element 210n-1, and the n$^{th}$ color filter 310n may be independently disposed in contact with each other or may be disposed, for example, through an insulating layer (not shown). For example, each of the first, second and third light sources 210a, 210b, and 210c may comprise a separate light emitting element of a plurality of light emitting elements (210a-1, 210b-1, and 210c-1, respectively) that is configured to emit light of a same emission spectrum, and each of the first, second and third light sources 210a, 210b, and 210c may further comprise a separate color filter of a plurality of color filters (310a, 310b, and 310c, respectively), wherein the plurality of color filters are overlapped with separate, respective light emitting elements (e.g., 210a-1, 210b-1, and 210c-1, respectively) of the plurality of light emitting elements (e.g., overlapped in the z direction which extends perpendicular to the in-plane direction of the substrate 110).

The first light emitting element 210a-1, the second light emitting element 210b-1, the third light emitting element 210c-1, and the n$^{th}$ light emitting element 210n-1 may be configured to emit light of a common emission spectrum (e.g., a same emission spectrum). The common emission spectrum may include transmission spectra of the first, second, third, and n$^{th}$ color filters 310a, 310b, 310c, and 310n.

The first, second, third, and n$^{th}$ color filters 310a, 310b, 310c, and 310n may be configured to selectively transmit light of different wavelength spectra belonging to a common emission spectrum emitted from a first light emitting element 210a-1, a second light emitting element 210b-1, and a third light emitting element 210c-1, and the n$^{th}$ light emitting element 210n-1. That is, the first, second, third, and n$^{th}$ color filters 310a, 310b, 310c, and 310n may provide wavelength selectivity to a common emission spectrum. In some example embodiments, the first, second, third, and n$^{th}$ color filters 310a, 310b, 310c, and 310n may collectively comprise a color filter 310 that is overlapped (e.g., in the Z direction extending perpendicular to the upper surface of the substrate 110) with a light source 210 that includes a plurality of light emitting elements (e.g., 210a-1, 210b-1, 210c-1, and 210n-1) that are configured to emit light of a common emission spectrum (e.g., a same emission spectrum).

For example, the first color filter 310a may be configured to selectively transmit light of a first transmission spectrum $SP_{T1}$ having a first maximum transmission wavelength $\lambda_{T1,max}$ among the common emission spectrum, and may be configured to absorb or reflect other light. For example, the second color filter 310b may be configured to selectively transmit light of a second transmission spectrum $SP_{T2}$ having a second maximum transmission wavelength $\lambda_{T2,max}$ among the common emission spectrum, and may be configured to absorb or reflect other light. For example, the third color filter 310c may be configured to selectively transmit light of a third transmission spectrum $SP_{T3}$ having a third maximum transmission wavelength $\lambda_{T3,max}$ among the common emission spectrum, and may be configured to absorb or reflect other light. For example, the n$^{th}$ color filter 310n may be configured to selectively transmit light of a n$^{th}$ transmission spectrum $SP_{Tn}$ having an n$^{th}$ maximum transmission wavelength $\lambda_{Tn,max}$ among the common emission spectrum, and may be configured to absorb or reflect other light.

Referring to FIGS. 8A to 8D, the first, second, third, and n$^{th}$ light emitting elements 210a-1, 210b-1, 210c-1, and 210n-1 may be configured to emit light of a common emission spectrum $SP_{E0}$. Light of the common emission spectrum $SP_{E0}$ passes through the first, second, third, and n$^{th}$ color filters 310a, 310b, 310c, and 310n, respectively, and each light of the first transmission spectrum $SP_{T1}$ having the first maximum transmission wavelength $\lambda_{T1,max}$, the second transmission spectrum $SP_{T2}$ having the second maximum transmission wavelength $\lambda_{T2,max}$, the third transmission spectrum $SP_{T3}$ having the third maximum transmission wavelength $\lambda_{T3,max}$, and the n$^{th}$ transmission spectrum $SP_{Tn}$ having the n$^{th}$ maximum transmission wavelength $\lambda_{Tn,max}$ may be selectively transmitted.

The second maximum transmission wavelength $\lambda_{T2,max}$ may be a longer wavelength than the first maximum transmission wavelength $\lambda_{T1,max}$, the third maximum transmission wavelength $\lambda_{T3,max}$ may be a longer wavelength than the second maximum transmission wavelength $\lambda_{T2,max}$, and the n$^{th}$ maximum transmission wavelength $\lambda_{Tn,max}$ may be a longer wavelength than the third maximum transmission wavelength $\lambda_{T3,max}$. The first maximum transmission wavelength $\lambda_{T1,max}$, the second maximum transmission wavelength $\lambda_{T2,max}$, the third maximum transmission wavelength $\lambda_{T3,max}$, and the n$^{th}$ maximum transmission wavelength $\lambda_{Tn,max}$ may each be within the common emission spectrum $SP_{E0}$. The first maximum transmission wavelength $\lambda_{T1,max}$, the second maximum transmission wavelength $\lambda_{T2,max}$, the third maximum transmission wavelength $\lambda_{T3,max}$, and the n$^{th}$ maximum transmission wavelength $\lambda_{Tn,max}$ may be separated by a particular (or, alternatively, predetermined) interval. For example, each difference between two adjacent wavelengths of the first maximum transmission wavelength $\lambda_{T1,max}$, the second maximum transmission wavelength $\lambda_{T2,max}$, the third maximum transmission wavelength $\lambda_{T3,max}$, and the n$^{th}$ maximum transmission wavelength $\lambda Tn,max$ (e.g., each of a difference between the first and second maximum transmission wavelengths $\lambda_{T1,max}$ and $\lambda_{T2,max}$ and a difference between the second and third maximum transmission wavelengths $\lambda_{T2,max}$ and $\lambda_{T3,max}$) may be for example greater than or equal to about 10 nm, within the above range, greater than or equal to about 15 nm, greater than or equal to about 20 nm, greater than or equal to about 30 nm, greater than or equal to about 40 nm, or greater than or equal to about 50 nm, within the above range, about 10 nm to about 500 nm, about 15 nm to about 500 nm, about 20 nm to about 500 nm, about 30 nm to about 500 nm, about 40 nm to about 500 nm, about 50 nm to about 500 nm, about 10 nm to about 300 nm, about 15 nm to about 300 nm, about 20 nm to about 300 nm, about 30 nm to about 300 nm, about 40 nm to about 300 nm, or about 50 nm to about 300 nm.

The full width at half maximum (FWHM) of the transmission spectra $SP_{T1}$, $SP_{T2}$, $SP_{T3}$, and $SP_{Tn}$ may be, for example, less than or equal to about 300 nm, and within the above range, about 10 nm to about 300 nm, about 30 nm to about 250 nm, or about 50 nm to about 200 nm.

Due to such wavelength selectivity of the first, second, third, and n$^{th}$ color filters 310a, 310b, 310c, and 310n, the first light source 210a may be configured to emit light of the first emission spectrum $SP_{E1}$ having a first maximum emission wavelength $\lambda_{E1,max}$ by the combination of the first light emitting element 210a-1 and the first color filter 310a, the second light source 210b may be configured to emit light of the second emission spectrum $SP_{E2}$ having a second maximum emission wavelength $\lambda E2,max$ by a combination of the second light emitting element 210b-1 and the second color filter 310b, the third light source 210c may be configured to emit light of the third emission spectrum $SP_{E3}$ having a third maximum emission wavelength $\lambda E3,max$ by a combination of the third light emitting element 210c-1 and the third color filter 310c, and the $n^{th}$ light source 210n may be configured to emit the light of the $n^{th}$ emission spectrum $SP_{En}$ having the $n^{th}$ maximum emission wavelength $\lambda_{En,max}$ by a combination of the $n^{th}$ light emitting element 210n-1 and the $n^{th}$ color filter 310n.

The second maximum emission wavelength $\lambda_{E2,max}$ may be a longer wavelength than the first maximum emission wavelength $\lambda_{E1,max}$, the third maximum emission wavelength $\lambda_{E3,max}$ may be a longer wavelength than the second maximum emission wavelength $\lambda_{E2,max}$, and the $n^{th}$ maximum emission wavelength $\lambda_{En,max}$) may be a longer wavelength than the third maximum emission wavelength $\lambda_{E3,max}$. The first maximum emission wavelength $\lambda_{E1,max}$, the second maximum emission wavelength $\lambda_{E3,max}$, $\lambda_{E2,max}$, the third maximum emission wavelength and the $n^{th}$ maximum emission wavelength $\lambda_{En,max}$ may be separated by a particular (or, alternatively, predetermined) interval. For example, each difference between two adjacent wavelengths of the first maximum emission wavelength $\lambda_{E1,max}$, the second maximum emission wavelength $\lambda_{E2,max}$, the third maximum emission wavelength $\lambda_{E3,max}$, and the $n^{th}$ maximum emission wavelength $\lambda_{En,max}$ may be for example greater than or equal to about 10 nm, greater than or equal to about 15 nm, greater than or equal to about 20 nm, greater than or equal to about 30 nm, greater than or equal to about 40 nm, or greater than or equal to about 50 nm, within the above range, about 10 nm to about 500 nm, about 15 nm to about 500 nm, about 20 nm to about 500 nm, about 30 nm to about 500 nm, about 40 nm to about 500 nm, about 50 nm to about 500 nm, about 10 nm to about 300 nm, about 15 nm to about 300 nm, about 20 nm to about 300 nm, about 30 nm to about 300 nm, about 40 nm to about 300 nm, or about 50 nm to about 300 nm.

The full width at half maximum (FWHM) of the emission spectra $SP_{E1}$, $SP_{E2}$, $SP_{E3}$, and $SP_{En}$ may be, for example, less than or equal to about 300 nm, and within the above range, about 10 nm to about 300 nm, about 30 nm to about 250 nm, or about 50 nm to about 200 nm.

Since the sensor 220 may be configured to detect light emitted from the first, second, third, and $n^{th}$ light sources 210a, 210b, 210c, and 210n and reflected by internal tissue of a living body, like the aforementioned example, the absorption spectrum SPA of the sensor 220 may include light of all wavelength spectra emitted from the first, second, third, and $n^{th}$ light sources 210a, 210b, 210c, and 210n.

Hereinafter, another example of the bio imaging system 100 shown in FIGS. 1 to 2B will be described with reference to FIG. 9 along with FIGS. 3 to 6 and 8.

Figure 9:
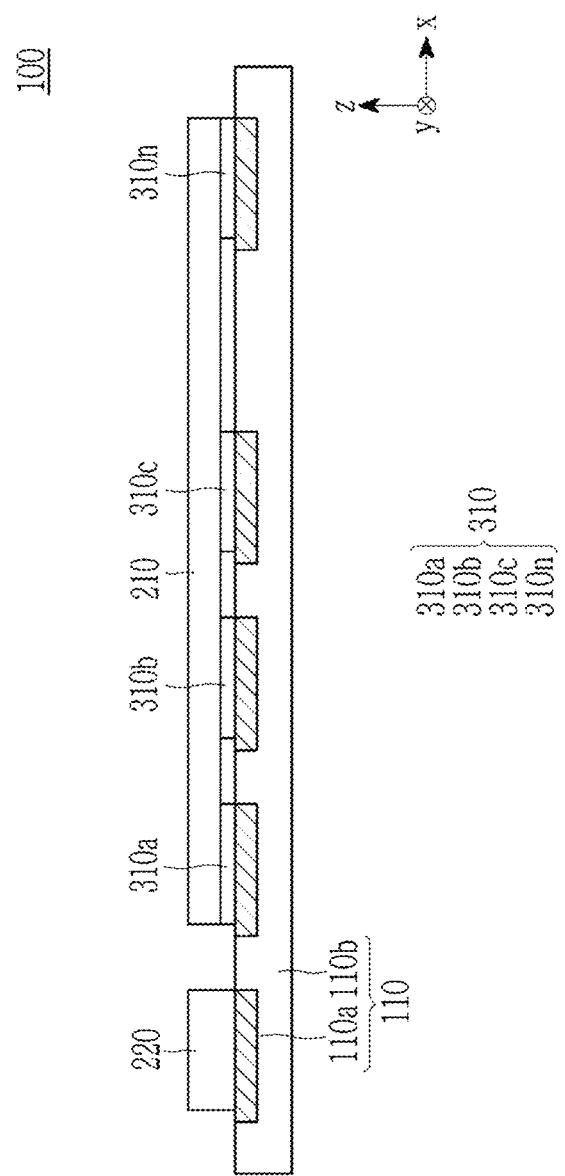
FIG. 9 is a cross-sectional view showing another example of the bio imaging system of FIG. 3 according to some example embodiments.

FIG. 9 is a cross-sectional view showing another example of the bio imaging system of FIG. 3 according to some example embodiments.

Referring to FIG. 9, a bio imaging system 100 according to some example embodiments includes a substrate 110; a plurality of light sources 210 arranged on the substrate 110; and a plurality of sensors 220 arranged on the substrate 110, like the aforementioned example.

However, unlike the aforementioned example, the bio imaging system 100 according to the present example may include the first, second, third, and $n^{th}$ color filters 310a, 310b, 310c, and 310n configured to transmit light of different wavelength spectra in relation to each other, under the light source 210 configured to emit light of a common wavelength spectrum. That is, instead of the first, second, third and $n^{th}$ light sources 210a, 210b, 210c, and 210n, which are separated from each other and overlapped with the first, second, third, and nth color filters 310a, 310b, 310c, and 310n, respectively, one light source 210 overlapped with the first, second, third, and nth color filters 310a, 310b, 310c, and 310n may be included. A plurality of light sources 210 may be arranged along rows and/or columns of the substrate 110.

The light source 210 may be configured to emit light of a common emission spectrum (e.g., white light), and the first, second, third, and $n^{th}$ color filters 310a, 310b, 310c, and 310n may provide wavelength selectivity to the common emission spectrum, like the aforementioned example. Therefore, as shown in FIG. 8, the light source 210, the first, second, third, and $n^{th}$ color filters 310a, 310b, 310c, and 310n, and the sensor 220 have the optical characteristics shown in FIGS. 8A to 8D.

Hereinafter, an example of the bio imaging system 100 shown in FIGS. 1 to 2B will be described with reference to FIGS. 10 to 13B.

Figure 10:
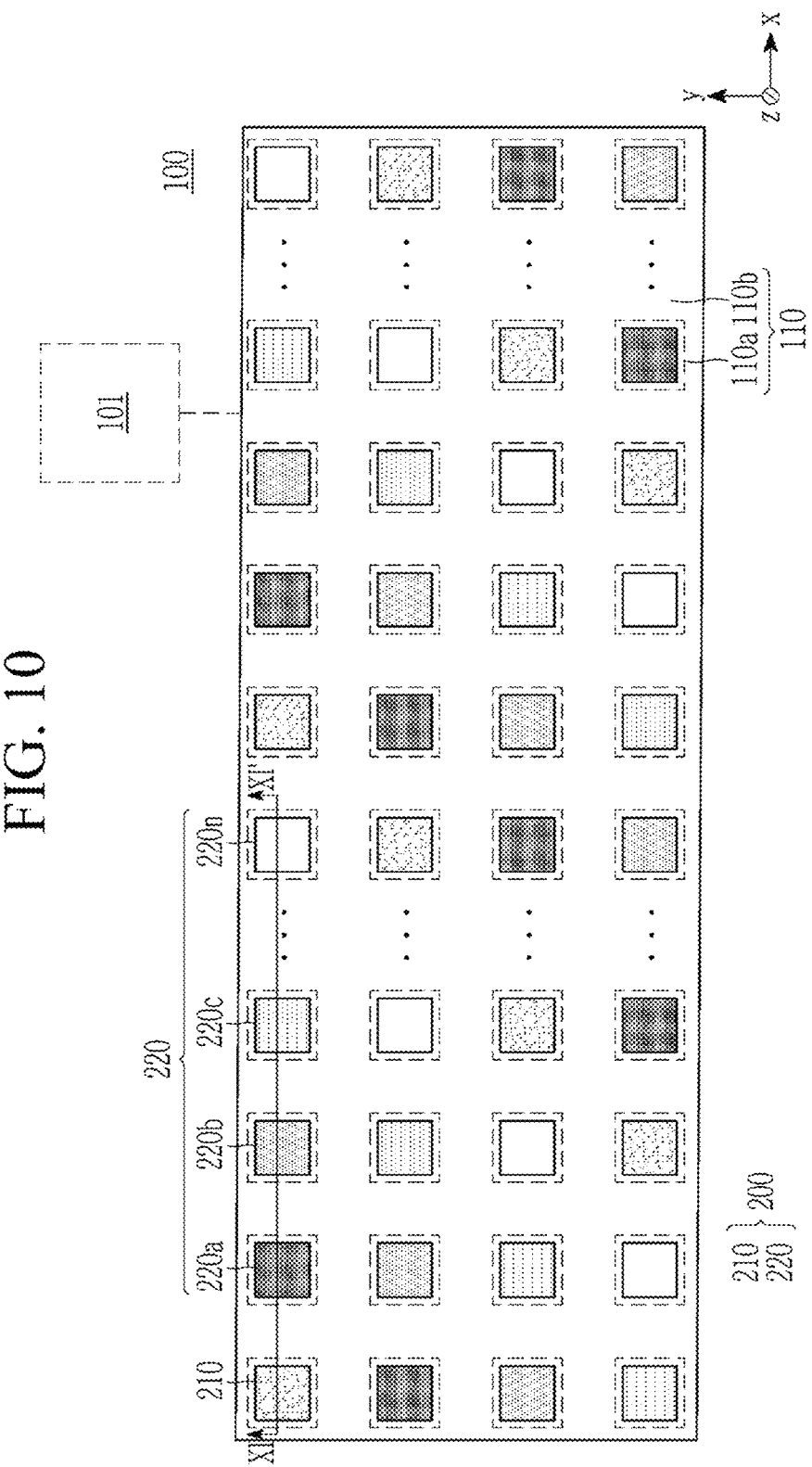
FIG. 10 is a plan view showing an example of the bio imaging system shown in FIGS. 1 to 2C according to some example embodiments.
Figure 11:
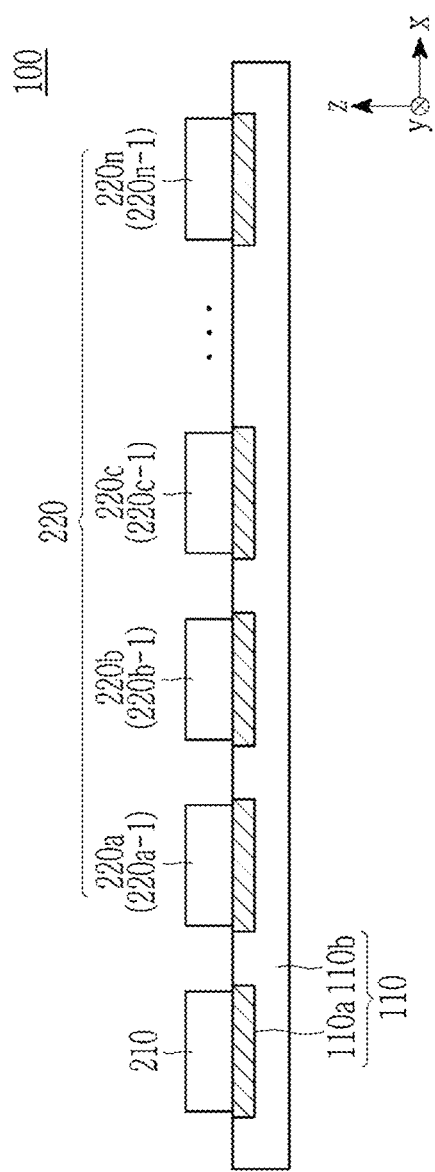
FIG. 11 is a cross-sectional view of an example of the bio imaging system of FIG. 10 taken along line XI-XI' according to some example embodiments.
Figure 12A:
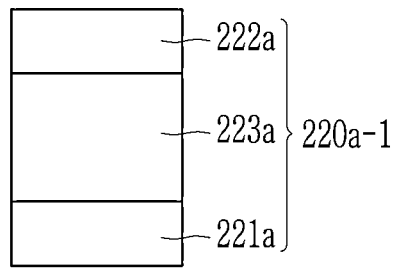
FIGS. 12A, 12B, 12C, and 12D are cross-sectional views showing examples of the sensor shown in FIGS. 10 and 11 according to some example embodiments.
Figure 12B:
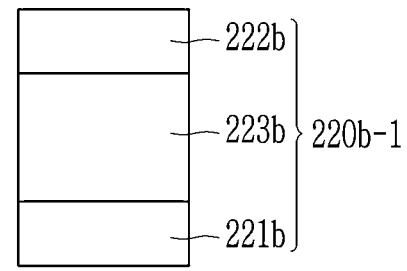
Figure 12C:
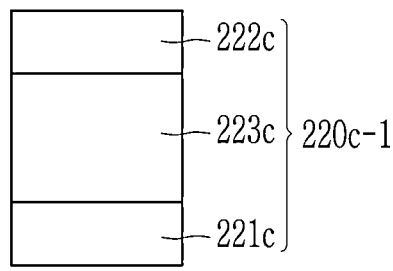
Figure 12D:
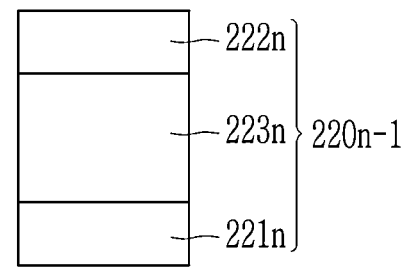
Figure 13A:
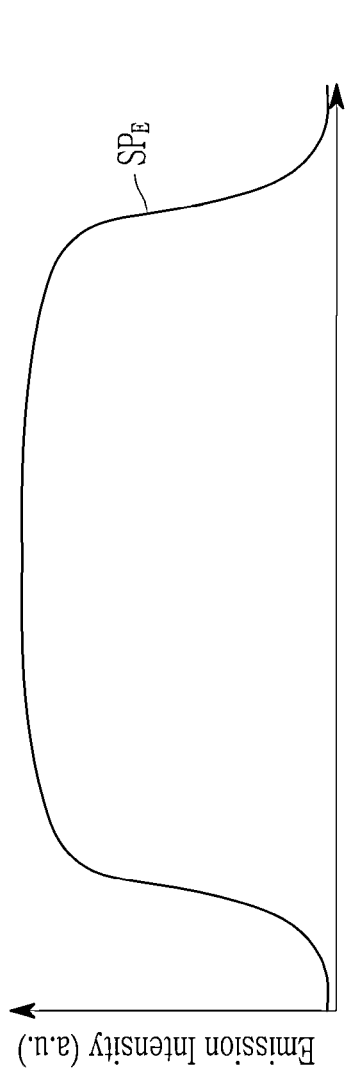
FIGS. 13A and 13B are graphs showing an example of wavelength spectra of a light source and a sensor of the bio imaging system shown in FIGS. 10 and 11 according to some example embodiments.
Figure 13B:
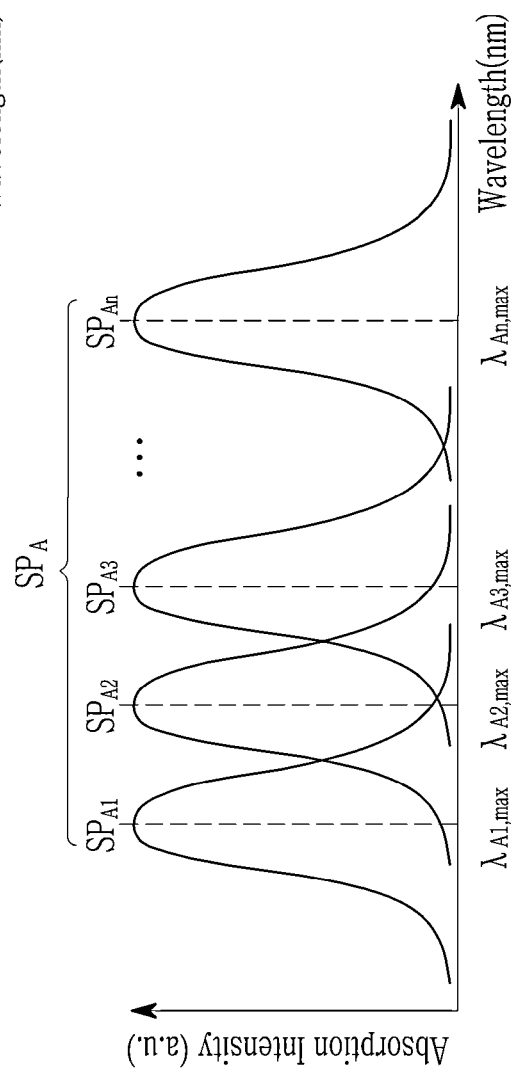

FIG. 10 is a plan view showing an example of the bio imaging system shown in FIGS. 1 to 2C, FIG. 11 is a cross-sectional view of an example of the bio imaging system of FIG. 10 taken along line XI-XI', FIGS. 12A, 12B, 12C, and 12D are cross-sectional view showing an example of the sensor shown in FIGS. 10 and 11, and FIGS. 13A and 13B are graphs showing an example of wavelength spectra of a light source and a sensor of the bio imaging system shown in FIGS. 10 and 11.

Referring to FIGS. 10 and 11, a bio imaging system 100 according to some example embodiments includes a substrate 110; a plurality of light sources 210 arranged on the substrate 110; and a plurality of sensors 220 arranged on the substrate 110 and configured to absorb light of different wavelength spectra. As described above, the plurality of light sources 210 and the plurality of sensors 220 may be on the rigid region 110a of the substrate 110.

The light source 210 may include a light emitting element 210-1 including a pair of electrodes 211 and 212 facing each other and a light emitting layer 213 between the pair of electrodes 211 and 212, as shown in FIG. 2A. The light emitting characteristics of the light source 210 may be the same or substantially the same as the light emitting characteristics of the light emitting layer 213, and the emission spectrum of the light source 210 may include light of all absorption spectra absorbed by the sensor 220.

The sensor 220 includes a first sensor 220a, a second sensor 220b, and a third sensor 220c that are separated from each other. The sensor 220 may additionally include an $n^{th}$ sensor 220n in addition to the first sensor 220a, the second sensor 220b, and the third sensor 220c, wherein n may be an integer of 4 to 10. The $n^{th}$ sensor 220n does not mean one sensor, but an $n^{th}$ sensor. For example, when n is 7, the sensor 220 may further include fourth, fifth, sixth, and seventh sensors in addition to the first sensor 220a, the second sensor 220b, and the third sensor 220c. The $n^{th}$ sensor 220n may be omitted.

The first sensor 220a, the second sensor 220b, the third sensor 220c, and the $n^{th}$ sensor 220n may be arranged in parallel (e.g., may extend in a linear sequence) along an in-plane direction (e.g., x direction, y direction, or xy direction) of the substrate 110 and light of different wavelength spectra belonging to the visible to infrared wavelength spectra may be absorbed. For example, the first sensor 220a, the second sensor 220b, the third sensor 220c, and the $n^{th}$ sensor 220n may be configured to selectively absorb light of different wavelength spectra (e.g., different absorption spectra) in relation to each other within a wavelength range of about 380 nm to about 3 μm, respectively, and a plurality of images obtained by light of different absorption spectra in relation to each other are combined to obtain a three-dimensional image of an internal tissue of a living body.

The first sensor 220a, second sensor 220b, third sensor 220c, and $n^{th}$ sensor 220n may include each a first light absorption element 220a-1, a second light absorption element 220b-1, a third light absorption element 220c-1, and an $n^{th}$ light absorption element 220n-1 which are configured to absorb light of different absorption spectra in relation to each other. That is, the first sensor 220a may include the first light absorption element 220a-1, the second sensor 220b may include the second light absorption element 220b-1, the third sensor 220c may include the third light absorption element 220c-1, and the $n^{th}$ sensor 220n may include the $n^{th}$ light absorption element 220n-1. Each of the first, second, third, and $n^{th}$ light absorption elements 220a-1, 220b-1, 220c-1, and 220n-1 may be an inorganic photoelectric conversion element or an organic photoelectric conversion element.

Referring to of FIGS. 12A to 12D, the first light absorption element 220a-1 may include a pair of electrodes 221a and 222a facing each other and a light absorption layer 223a between the pair of electrodes 221a and 222a, and the second light absorption element 220b-1 may include a pair of electrodes 221b and 222b facing each other and a light absorption layer 223b between the pair of electrodes 221b and 222b, the third light absorption element 220c-1 may include a pair of electrodes 221c and 222c facing each other and a light absorption layer 223c between the pair of electrodes 221c and 222c, and the $n^{th}$ light absorption element 220n-1 may include a pair of electrodes 221n and 222n facing each other and a light absorption layer 223n between the pair of electrodes 221n and 222n. The descriptions of the pair of electrodes 221 and 222 and the light absorption layer 223 is as described above.

The absorption spectrum of the light absorbed by the first light absorption element 220a-1, second light absorption element 220b-1, third light absorption element 220c-1, and $n^{th}$ light absorption element 220n-1 may be determined by the light absorption layers 223a, 223b, 223c, and 223n, and the light absorption layers 223a, 223b, 223c, and 223n may be configured to absorb light of different emission spectra in relation to each other. For example, each of the first light absorption element 220a-1, second light absorption element 220b-1, third light absorption element 220c-1, and $n^{th}$ light absorption element 220n-1 may be configured to absorb light of a first absorption spectrum $SP_{A1}$ having a first maximum absorption wavelength $\lambda_{A1,max}$, a second absorption spectrum $SP_{A2}$ having a second maximum absorption wavelength $\lambda_{A2,max}$, a third absorption spectrum $SP_{A3}$ having a third maximum absorption wavelength $\lambda_{A3,max}$, and an $n^{th}$ absorption spectrum $SP_{An}$ having an $n^{th}$ maximum absorption wavelength $\lambda_{An,max}$, wherein the first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$ may be different from each other.

Referring to FIG. 13, the first light absorption element 220a-1 may be configured to absorb light of the first absorption spectrum $SP_{A1}$ having the first maximum absorption wavelength $\lambda_{A1,max}$, the second light absorption element 220b-1 may be configured to absorb light of the absorption spectrum $SP_{A2}$ having the second maximum absorption wavelength $\lambda_{A2,max}$, the third light absorption element 220c-1 may be configured to absorb light of the absorption spectrum $SP_{A3}$ having the third maximum absorption wavelength $\lambda_{A3,max}$, and the $n^{th}$ light absorption element 220n-1 may be configured to absorb light of the absorption spectrum $SP_{An}$ having the $n^{th}$ maximum absorption wavelength $\lambda_{An,max}$. That is, the light absorption layer 223a may be configured to absorb light of the absorption spectrum having the first maximum absorption wavelength $\lambda_{A1,max}$, the light absorption layer 223b may be configured to absorb light of the absorption spectrum having the second maximum absorption wavelength $\lambda_{A2,max}$, the light absorption layer 223c may be configured to absorb light of the absorption spectrum having the third maximum absorption wavelength $\lambda_{A3,max}$, and the light absorption layer 223n may be configured to absorb light of the absorption spectrum having the $n^{th}$ maximum absorption wavelength $\lambda_{An,max}$.

The second maximum absorption wavelength $\lambda_{A2,max}$ may be a longer wavelength than the first maximum absorption wavelength $\lambda_{A1,max}$, the third maximum absorption wavelength $\lambda_{A3,max}$ may be a longer wavelength than the second maximum absorption wavelength $\lambda_{A2,max}$, and the $n^{th}$ maximum absorption wavelength $\lambda_{An,max}$ may be a longer wavelength than the third maximum absorption wavelength $\lambda_{A3,max}$. The first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$ may be separated by a particular (or, alternatively, predetermined) interval. For example, each difference between two adjacent wavelengths of the first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$, for example a difference between the first and second maximum absorption wavelengths $\lambda_{A1,max}$ and $\lambda_{A2,max}$ and a difference between the second and third maximum absorption wavelengths $\lambda_{A2,max}$ and $\lambda_{A3,max}$, may be for example greater than or equal to about 10 nm, within the range, greater than or equal to about 15 nm, greater than or equal to about 20 nm, greater than or equal to about 30 nm, greater than or equal to about 40 nm, or greater than or equal to about 50 nm, within the range, about 10 nm to about 500 nm, about 15 nm to about 500 nm, about 20 nm to about 500 nm, about 30 nm to about 500 nm, about 40 nm to about 500 nm, about 50 nm to about 500 nm, about 10 nm to about 300 nm, about 15 nm to about 300 nm, about 20 nm to about 300 nm, about 30 nm to about 300 nm, about 40 nm to about 300 nm or about 50 nm to about 300 nm.

The first maximum absorption wavelength $\lambda_{A1,max}$, the second maximum absorption wavelength $\lambda_{A2,max}$, the third maximum absorption wavelength $\lambda_{A3,max}$ and the $n^{th}$ maximum absorption wavelength $\lambda_{An,max}$ may belong to a visible to infrared wavelength spectra, and may be for example independently within about 380 nm to about 3 μm, about 400 nm to about 2 μm, about 450 nm to about 1500 nm, about 470 nm to about 1150 nm, about 480 nm to about 1100 nm, about 500 nm to about 1000 nm, about 550 nm to about 1000 nm, or about 600 nm to about 1000 nm. For example, the first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$ may each independently belong to one of a blue wavelength spectrum, a green wavelength spectrum, a red wavelength spectrum, or a (near) infrared wavelength spectrum, wherein the blue wavelength spectrum may be greater than or equal to about 400 nm and less than about 500 nm, the green wavelength spectrum may be greater than or equal to about 500 nm and less than or equal to about 600 nm, the red wavelength spectrum may be greater than about 600 nm and less than or equal to about 700 nm, and the (near) infrared wavelength spectrum may be greater than about 700 nm and less than or equal to about 3000 nm.

The full width at half maximum (FWHM) of the absorption spectra $SP_{A1}$, $SP_{A2}$, $SP_{A3}$, and $SP_{An}$ may be, for example, less than or equal to about 300 nm, and within the above range, about 10 nm to about 300 nm, about 30 nm to about 250 nm, or about 50 nm to about 200 nm.

Since the light source 210 supplies light absorbed by the first, second, third, and $n^{th}$ sensors 220a, 220b, 220c, and 220n, the emission spectrum $SP_E$ of the light source 210 may include light of all wavelength spectra absorbed by the first, second, third, and $n^{th}$ sensors 220a, 220b, 220c, and 220n.

For example, the emission spectrum of light supplied from the light source 210 may include all absorption spectra of the first to $n^{th}$ sensors 220a, 220b, 220c, and 220n and may be for example, within about 380 nm to about 3 μm, about 400 nm to about 2 μm, about 450 nm to about 1500 nm, about 470 nm to about 1150 nm, about 480 nm to about 1100 nm, about 500 nm to about 1000 nm, about 550 nm to about 1000 nm, or about 600 nm to about 1000 nm. For example, when the first, second, third sensor 220a, 220b, and 220c are configured to absorb light of a blue wavelength spectrum, a green wavelength spectrum, and a red wavelength spectrum, respectively, the light source 210 may be configured to emit light in in a white wavelength spectrum including the blue wavelength spectrum, green wavelength spectrum, and red wavelength spectrum.

In the bio imaging system 100 according to the present example, a plurality of sensors 220a, 220b, 220c, and 220n configured to absorb light of different absorption spectra in relation to each other may provide a plurality of images of internal tissue of a living body according to the depth direction from the skin surface by using the difference in the penetration depth of light according to the wavelength. These the plurality of images are combined to obtain information such as a location, shape, size, and/or thickness of the internal tissues of the living body (e.g., blood vessels), and this information may be used to obtain spatial information of the internal tissues of the living body. In addition, this spatial information may be separated and/or extracted to effectively obtain information of the internal tissues of the living body present at a specific depth from the skin surface.

Specifically, as described above, the light irradiated from the light source 210 has a different penetration depth of light from the skin surface according to the wavelength, and light of a relatively long wavelength spectrum may penetrate relatively deeper than light of a relatively short wavelength spectrum. Therefore, in the bio imaging system 100 shown in FIGS. 10 to 13B, the image obtained by the third sensor 220c configured to absorb light of the third absorption spectrum $SP_{A3}$ having the third maximum absorption wavelength $\lambda_{A3,max}$ may be an image at a position deeper than the image obtained from the second sensor 220b configured to absorb light of the second absorption spectrum $SP_{A2}$ having a second maximum absorption wavelength $\lambda_{A2,max}$, which is a relatively short wavelength, and the image obtained from the second sensor 220b configured to absorb light of the second absorption spectrum $SP_{A2}$ having the second maximum absorption wavelength $\lambda_{A2,max}$ may be an image of a position deeper than the image obtained by the first sensor 220a configured to absorb light of the first absorption spectrum $SP_{A1}$ of the first maximum absorption wavelength $\lambda A1,max$, which is a relatively short wavelength.

Therefore, by extracting the difference between the image obtained from the third sensor 220c and the image obtained from the second sensor 220b, image information at a depth at which only light of a wavelength corresponding to the third absorption spectrum $SP_{A3}$ penetrates may be obtained, and similarly, by extracting the difference between the image obtained from the second sensor 220b and the image obtained from the first sensor 220a, image information at a depth at which only light of a wavelength corresponding to the second absorption spectrum $SP_{A2}$ penetrates may be obtained. Accordingly, it is possible to effectively obtain image information of an internal tissue of a living body located at a specific depth from the skin surface.

In this way, differences between images obtained from any two sensors among n sensors 220a, 220b, 220c, and 220n configured to absorb light of different absorption spectra in relation to each other are extracted and combined, and thereby, spatial information may be secured in the depth direction.

Figure 30:
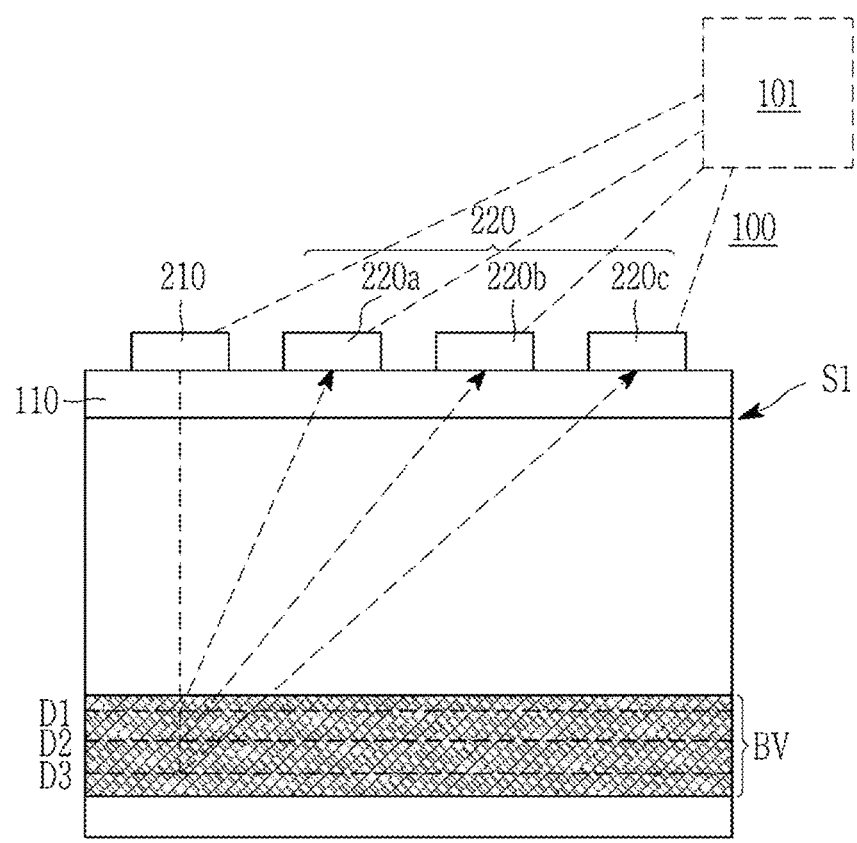
FIG. 30 is a schematic cross-sectional view showing an example of a method of obtaining image information of an internal tissue of a living body using the bio imaging system of FIG. 10 according to some example embodiments.

FIG. 30 is a schematic cross-sectional view showing an example of a method of obtaining image information of an internal tissue of a living body using the bio imaging system of FIG. 10.

Like the aforementioned example, a bio imaging method using the bio imaging system 100 may include fixing the bio imaging system 100 on the skin S; radiating light into the skin S by turning on the light source 210; absorbing light passing the skin S and scattered and reflected by the internal tissues of the living body such as blood vessel BV by the sensor 220 to obtain a plurality of images by the light of a wavelength spectrum different from each other; extracting the plurality of images of the internal tissues of the living body such as the blood vessel BV depending on a depth from the surface of the skin S; and combining the plurality of images (e.g., plurality of extracted images) of the internal tissues of the living body such as the blood vessel BV to obtain a three-dimensional image of the internal tissues of the living body.

Referring to FIG. 30 together with FIGS. 25 and 27A and 27B, the sensor 220 may include first, second, and third sensors (e.g., 220a, 220b, and 220c) configured to absorb light of different absorption spectra in relation to each other. The depths $D_1$, $D_2$, and $D_3$ at which the light irradiated from the light irradiated from the light source 210 penetrate according to the wavelength have a particular (or, alternatively, predetermined) distribution, and images of an internal tissue of a living body reflected at different depths according to wavelengths may be obtained from the first, second, and third sensors 220a, 220b, and 220c configured to absorb light of different absorption spectra in relation to each other. For example, since among the first, second, and third sensors 220a, 220b, 220c, the first sensor 220a is configured to absorb light of the first absorption spectrum $SP_{A1}$ of the relatively shortest wavelength, and the third sensor 220c is configured to absorb light of the absorption spectrum $SP_{A3}$ of the relatively longest wavelength, the signals obtained by irradiation of light of the first to third absorption spectra $SP_{A1}$, $SP_{A2}$, and $SP_{A3}$ may provide images $M_1$, $M_2$, and $M_3$ from a relatively close depth $D_1$ to the deepest depth $D_3$ from the skin surface S1. Based on these images $M_1$, $M_2$, and $M_3$, the image difference according to each depth $D_1$, $D_2$, and $D_3$ is extracted, and the lowest point, the middle point, and the highest point of the blood vessel BV are specified to obtain a three-dimensional image of the blood vessel BV. For example, extracting differences between the images $M_1$, $M_2$, and $M_3$ may include extracting an image of the internal tissue of the living body located at a first depth $D_1$ from the skin S surface based on a difference between an image obtained based on the second sensor 220b absorbing light and an image obtained based on the first sensor 220a absorbing light, and extracting an image of the internal tissue of the living body located at a second depth $D_2$ deeper than the first depth $D_1$ based on a difference between an image obtained based on the third sensor 220c absorbing light and the image obtained based on the second sensor 220b absorbing light. Spatial information such as the location, shape, size and/or thickness of the blood vessel BV may be confirmed from the three-dimensional image of the blood vessel BV.

When two or more of the plurality of blood vessels BV1 and BV2 are located in the depth direction, an image of the blood vessel BV located at a specific depth may be obtained by separating the images of the plurality of blood vessels BV and extracting the difference.

That is, the depths $D_1$, $D_2$, and $D_3$ at which the light irradiated from the light source 210 penetrate according to the wavelength have a particular (or, alternatively, predetermined) distribution, and information of blood vessels BV1 and BV2 reflected by the different depths $D_1$, $D_2$, and $D_3$ according to the wavelength may be selectively obtained from a plurality of sensors 220a, 220b, 220c configured to absorb light of different wavelength spectra. Image information obtained from light of the first to third absorption spectra may each include spatial information from a depth $D_1$ relatively close to a deepest depth $D_3$ from the skin surface S1 respectively, and it is possible not only to obtain a three-dimensional image of each blood vessel BV1 and BV2, by extracting the difference between the plurality of images and specifying the lowest point, the middle point, and the highest point of each blood vessel BV1 and BV2, but also to obtain a clear image of the blood vessel BV2 without reducing the resolution caused by the blood vessel BV1, by extracting the difference between the image obtained from the blood vessel BV1 and the image obtained from the blood vessel BV1. Therefore, when the plurality of blood vessels BV1 and BV2 are located in the depth direction from the skin surface S1, spatial information of the internal tissues of the living body may be effectively checked in this manner. Here, an example in which two blood vessels BV1 and BV2 are located in the depth direction has been described, but a case in which n blood vessels are located in the depth direction may also be described.

Meanwhile, the bio imaging method may further include obtaining a correction image before obtaining the aforementioned three-dimensional image. The correction image is for excluding an influence of the light characteristics (e.g., scattering and/or absorption) of the skin caused by differences in skin color and thickness of subcutaneous tissue for each individual, and may be obtained based on, for example, a point spread function. For example, the correction image may be obtained by operating only some of the sensor 220 of the first position (specific position) of the bio imaging system 100 to obtain an image according to the wavelength spectrum of the first position corresponding to the operated some of the sensor 220 and by operating only some of the sensor 220 of the second position (specific position) of the bio imaging system 100 to obtain an image according to the wavelength spectrum of the second position corresponding to the operated some of the sensor 220, and in this way, operating only some of the sensor 220 of the $n^{th}$ position to obtain an image according to the wavelength spectrum of the $n^{th}$ position corresponding to the operated some of the sensor. The correction image may be applied to the plurality of extracted images to correct the plurality of extracted images. The corrected extracted images may then be combined to obtain the three-dimensional image. By correcting the aforementioned plurality of extracted images using the correction image, the effect of the optical characteristics of the skin may be excluded to obtain a clear three-dimensional image.

Hereinafter, another example of the bio imaging system 100 shown in FIGS. 1 and 2A to 2C will be described with reference to FIG. 14 along with FIGS. 10 to 13.

Figure 14:
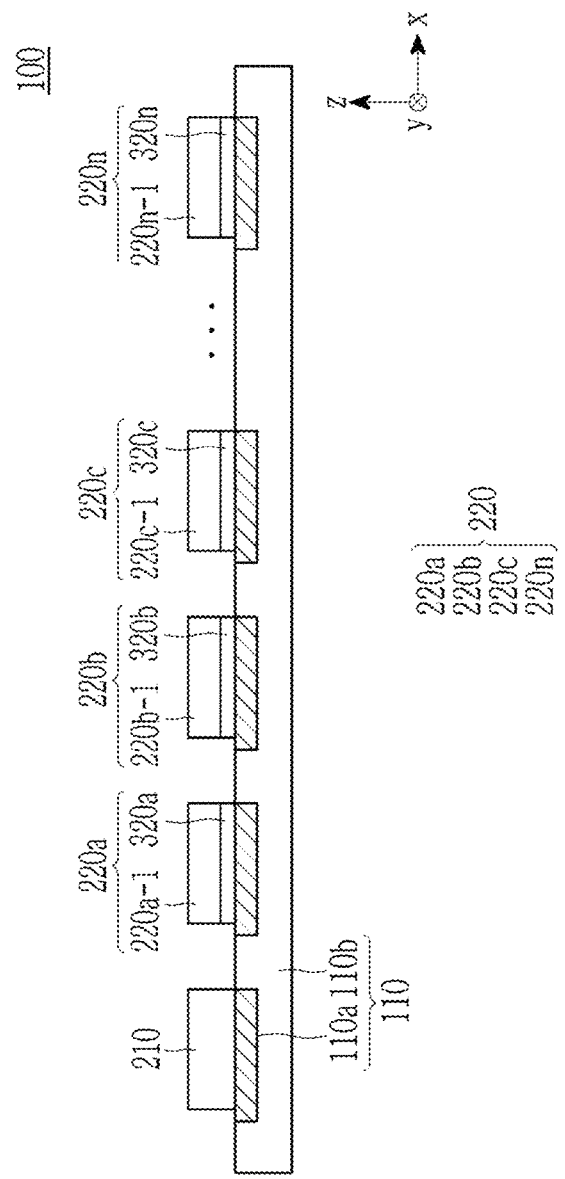
FIG. 14 is a cross-sectional view of another example of the bio imaging system of FIG. 10 taken along line XI-XI' according to some example embodiments.
Figure 15A:
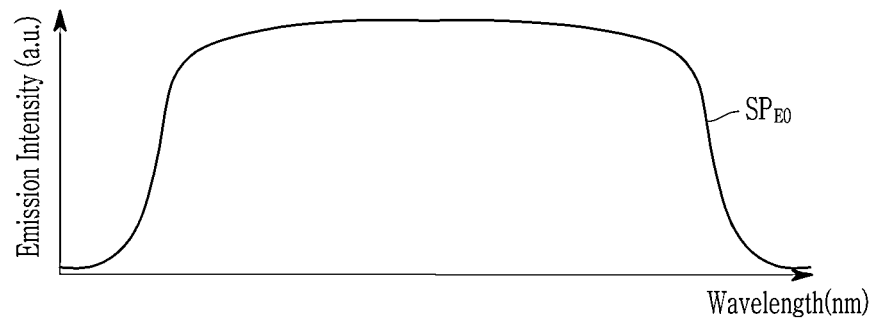
FIGS. 15A, 15B, and 15C are graphs showing an example of wavelength spectra of a light source and a sensor of the bio imaging system shown in FIGS. 10 and 14 according to some example embodiments.
Figure 15B:
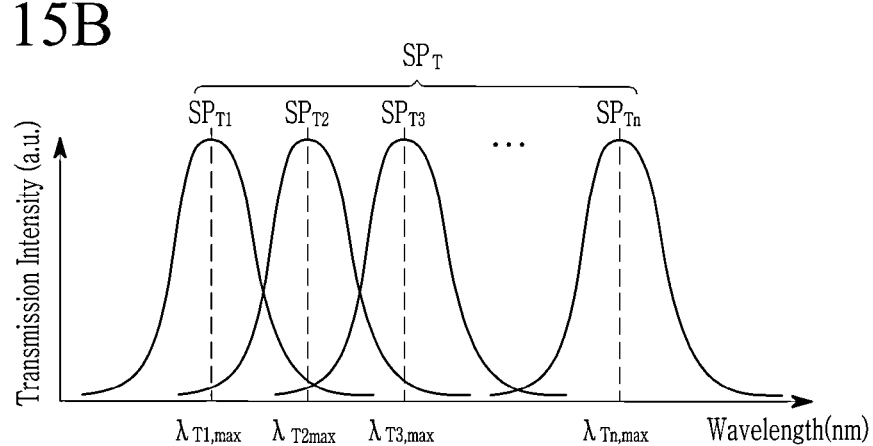
Figure 15C:
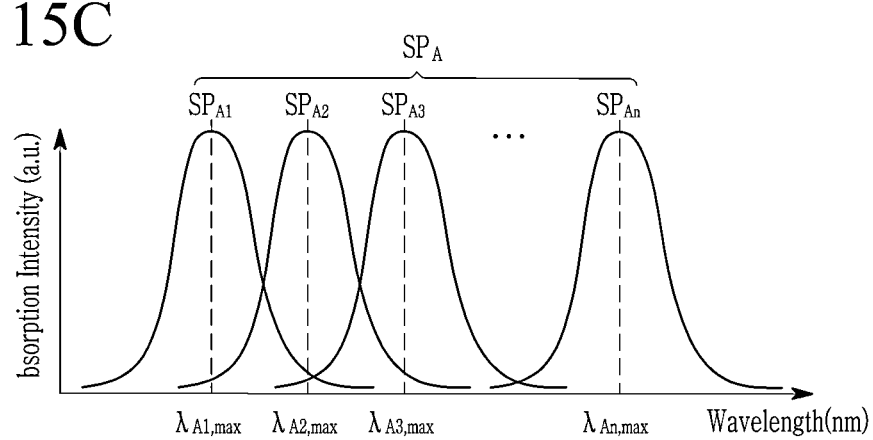

FIG. 14 is a cross-sectional view of another example of the bio imaging system of FIG. 10 taken along line XI-XI' and FIGS. 15A, 15B, and 15C are graphs showing an example of wavelength spectra of a light source and a sensor of the bio imaging system shown in FIGS. 10 and 14.

Referring to FIG. 14, a bio imaging system 100 according to an example includes a substrate 110; a plurality of light sources 210 arranged on the substrate 110; and a plurality of sensors 220 arranged on the substrate 110, wherein the sensors 220 include a first sensor 220a, a second sensor 220b, a third sensor 220c, and optionally $n^{th}$ sensor 220n which are separated from each other and configured to absorb light of different wavelength spectra, like the aforementioned example.

However, in the bio imaging system 100 according to the present example, unlike the bio imaging system 100 according to the aforementioned example, the first, second, third, and $n^{th}$ sensors 220a, 220b, 220c, and 220n may include a first light absorption element 220a-1, a second light absorption element 220b-1, a third light absorption element 220c-1, and an $n^{th}$ light absorption element 220n-1 which each is configured to absorb light of a common absorption spectrum (e.g., same absorption spectrum), wherein each of the first sensor 220a, the second sensor 220b, the third sensor 220c, and the $n^{th}$ sensor 220n may further include first, second, third, and $n^{th}$ color filters 320a, 320b, 320c, and 320n for color separation. That is, the first sensor 220a includes a first light absorption element 220a-1 and a first color filter 320a, the second sensor 220b includes a second light absorption element 220b-1 and a second color filter 320b, the third sensor 220c includes a third light absorption element 220c-1 and a third color filter 320c, and the $n^{th}$ sensor 220n includes the $n^{th}$ light absorption element 220n-1 and an $n^{th}$ color filter 320n. As shown, each sensor of the first, second, and third sensors 220a to 220c may comprise a separate light absorption element of a plurality of light absorption elements (e.g., a respective one of light absorption elements 220a-1 to 220c-1) and a separate color filter of a plurality of color filters (e.g., a respective one of color filters 320a to 320c), where the separate color filter of a given sensor is overlapped with the separate light absorption element of the given sensor in the Z direction extending perpendicular to the upper surface of the substrate 110, wherein the plurality of light absorption elements 220a-1 to 220c-1 of the first, second, and third sensors 220a to 220c are configured to selectively absorb light of a same absorption spectrum.

The first, second, third, and $n^{th}$ color filters 320a, 320b, 320c, and 320n (which may be referred to herein as the a plurality of color filters) may be respectively at each position through which light emitted from the first light absorption element 220a-1, the second light absorption element 220b-1, the third light absorption element 220c-1, and the $n^{th}$ light absorption element 220n-1 pass, may be for example overlapped with the first light absorption element 220a-1, the second light absorption element 220b-1, the third light absorption element 220c-1, and the $n^{th}$ light absorption element 220n-1, respectively. The first light absorption element 220a-1 and the first color filter 320a, the second light absorption element 220b-1 and the second color filter 320b, the third light absorption element 220c-1 and the third color filter 320c, and the $n^{th}$ light absorption element 220n-1 and the $n^{th}$ color filter 320n may be independently in contact with each other or may be, for example, through an insulating layer (not shown).

The first light absorption element 220a-1, the second light absorption element 220b-1, the third light absorption element 220c-1, and the $n^{th}$ light absorption element 220n-1 may be configured to absorb (e.g., selectively absorb) light of a common absorption spectrum. The common absorption spectrum may include transmission spectra of the first, second, third and $n^{th}$ color filters 320a, 320b, 320c, and 320n.

The first, second, third, and $n^{th}$ color filters 320a, 320b, 320c, and 320n may be configured to selectively transmit light of different wavelength spectra belonging to a common absorption spectrum absorbed in the first light absorption element 220a-1, the second light absorption element 220b-1, the third light absorption element 220c-1, and the $n^{th}$ light absorption element 220n-1. That is, the first, second, third, and $n^{th}$ color filters 320a, 320b, 320c, and 320n may provide wavelength selectivity to a common absorption spectrum.

For example, the first color filter 320a may be configured to selectively transmit light of a first transmission spectrum having a first maximum transmission wavelength $\lambda_{T1,max}$ among the common absorption spectrum, and may be configured to absorb or reflect other light. For example, the second color filter 320b may be configured to selectively transmit light of a second transmission spectrum having a second maximum transmission wavelength $\lambda_{T2,max}$ among the common absorption spectrum, and may be configured to absorb or reflect other light. For example, the third color filter 320c may be configured to selectively transmit light of a third transmission spectrum having a third maximum transmission wavelength $\lambda_{T3,max}$ among the common absorption spectrum, and may be configured to absorb or reflect other light. For example, the $n^{th}$ color filter 320n may be configured to selectively transmit light of a $n^{th}$ transmission spectrum having an $n^{th}$ maximum transmission wavelength $\lambda_{Tn,max}$ among the common absorption spectrum, and may be configured to absorb or reflect other light.

Referring to FIGS. 15A, 15B, and 15C, the light source 210 may be configured to emit light of a particular (or, alternatively, predetermined) emission spectrum $SP_{E0}$. Light of the particular (or, alternatively, predetermined) emission spectrum $SP_{E0}$ is reflected by an internal tissue of a living body (e.g., blood vessel) and passes the first, second, third and $n^{th}$ color filters 320a, 320b, 320c, and 320n, respectively, and light passing the first, second, third and $n^{th}$ color filters 320a, 320b, 320c, and 320n, respectively may be light of a transmission spectrum $SP_{T1}$ having a first maximum transmission wavelength $\lambda_{T1,max}$, a transmission spectrum $SP_{T2}$ having a second maximum transmission wavelength $\lambda_{T2,max}$, a transmission spectrum $SP_{T3}$ having a third maximum transmission wavelength $\lambda_{T3,max}$, and a transmission spectrum $SP_{Tn}$ having an $n^{th}$ maximum transmission wavelength $\lambda_{Tn,max}$. That is, light passing through the first, second, third, and $n^{th}$ color filters 320a, 320b, 320c, and 320n, respectively, may have wavelength selectivity. Each of the first to $n^{th}$ maximum transmission wavelengths $\lambda_{T1,max}$ to $\lambda_{Tn,max}$ may be within the same absorption spectrum SPA that the plurality of light absorption elements 220a-1 to 220n-1 are configured to absorb.

Due to such wavelength selectivity of the first, second, third, and $n^{th}$ color filters 320a, 320b, 320c, and 320n, the first sensor 220a may be configured to absorb light of the absorption spectrum $SP_{A1}$ having a first maximum absorption wavelength $\lambda A1,max$ by the combination of the first light absorption element 220a-1 and the first color filter 320a, the second sensor 220b may be configured to absorb light of the absorption spectrum $SP_{A2}$ having a second maximum absorption wavelength $\lambda_{A2,max}$ by the combination of the second light absorption element 220b-1 and the second color filter 320b, the third sensor 220c 220a may be configured to absorb light of the absorption spectrum $SP_{A3}$ having a third maximum absorption wavelength $\lambda_{A3,max}$ by the combination of the third light absorption element 220c-1 and the third color filter 320c, and the $n^{th}$ sensor 220n may be configured to absorb light of the absorption spectrum $SP_{An}$ having the $n^{th}$ maximum absorption wavelength $\lambda_{An,max}$ by the combination of the light absorption element 220n-1 and the $n^{th}$ color filter 320n.

The second maximum absorption wavelength $\lambda_{A2,max}$ may be a longer wavelength than the first maximum absorption wavelength $\lambda A1,max$, the third maximum absorption wavelength $\lambda_{A3,max}$ may be a longer wavelength than the second maximum absorption wavelength $\lambda_{A2,max}$, and the $n^{th}$ maximum absorption wavelength $\lambda_{An,max}$ may be a longer wavelength than the third maximum absorption wavelength $\lambda_{A3,max}$. The first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$ may be separated by a particular (or, alternatively, predetermined) interval. For example, each difference between two adjacent wavelengths of the first maximum absorption wavelength $\lambda_{A1,max}$, the second maximum absorption wavelength $\lambda_{A2,max}$, the third maximum absorption wavelength $\lambda_{A3,max}$, and the $n^{th}$ maximum absorption wavelength $\lambda_{An,max}$ (e.g., a difference between the first and second maximum transmission wavelengths $\lambda_{A1,max}$ and $\lambda_{A2,max}$ and a difference between the second and third maximum transmission wavelengths $\lambda_{A2,max}$ and $\lambda_{A3,max}$) may be for example greater than or equal to about 10 nm, greater than or equal to about 15 nm, greater than or equal to about 20 nm, greater than or equal to about 30 nm, greater than or equal to about 40 nm, or greater than or equal to about 50 nm, within the above range, about 10 nm to about 500 nm, about 15 nm to about 500 nm, about 20 nm to about 500 nm, about 30 nm to about 500 nm, about 40 nm to about 500 nm, about 50 nm to about 500 nm, about 10 nm to about 300 nm, about 15 nm to about 300 nm, about 20 nm to about 300 nm, about 30 nm to about 300 nm, about 40 nm to about 300 nm, or about 50 nm to about 300 nm.

Each of the full width at half maximum (FWHM) of the transmission spectra $SP_{T1}$, $SP_{T2}$, $SP_{T3}$, and $SP_{Tn}$ and the absorption spectra $SP_{A1}$, $SP_{A2}$, $SP_{A3}$, and $SP_{An}$ may be, for example, less than or equal to about 300 nm, and within the above range, about 10 nm to about 300 nm, about 30 nm to about 250 nm, or about 50 nm to about 200 nm.

Hereinafter, an example of the bio imaging system 100 shown in FIGS. 1 and 2 will be described with reference to FIGS. 16 and 17.

Figure 16:
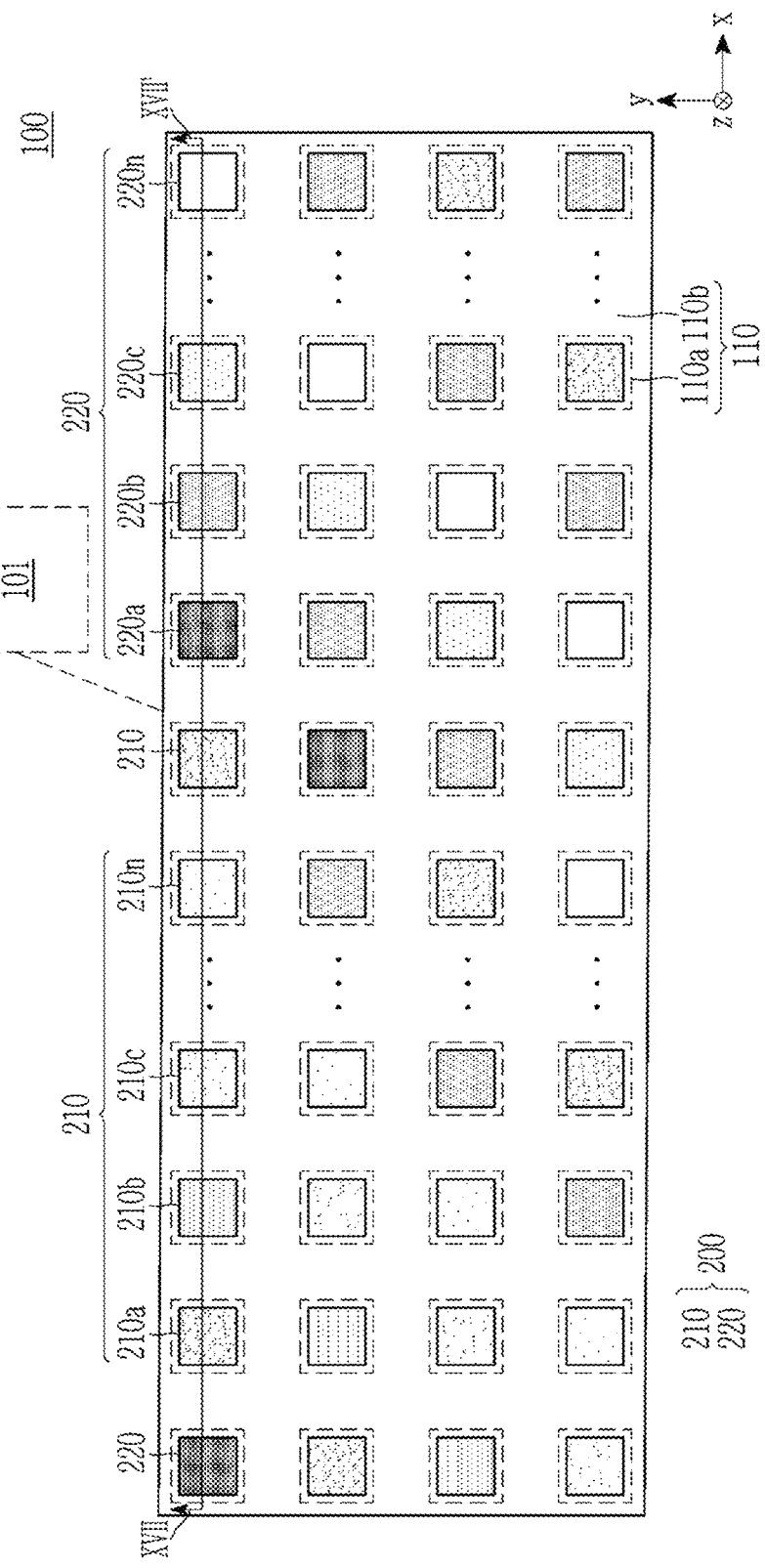
FIG. 16 is a plan view showing an example of the bio imaging system shown in FIGS. 1 to 2C according to some example embodiments.

FIG. 16 is a plan view showing an example of the bio imaging system shown in FIGS. 1 to 2B and FIG. 17 is a cross-sectional view of an example of the bio imaging system of FIG. 16 taken along line XVII-XVII'.

Figure 17:
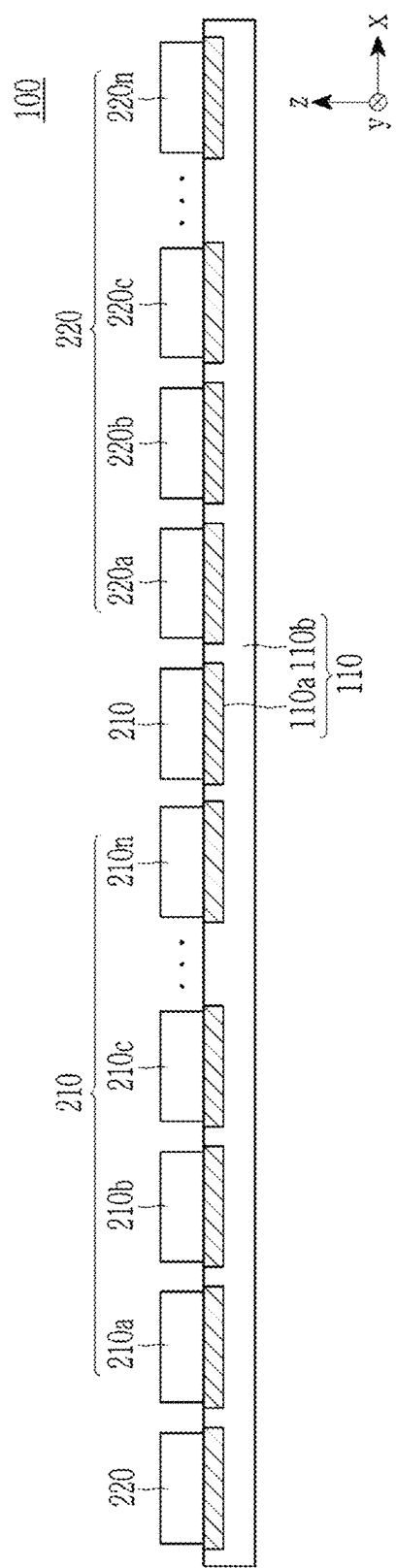
FIG. 17 is a cross-sectional view of an example of the bio imaging system of FIG. 16 taken along line XVII-XVII'.

Referring to FIGS. 16 and 17, a bio imaging system 100 according to some example embodiments includes a substrate 110; a plurality of light sources 210 including first, second, third, and $n^{th}$ light sources 210a, 210b, 210c, and 210n arranged on the substrate 110 and configured to emit light of different wavelength spectrum; and a plurality of sensors 220 including first, second, third, and $n^{th}$ sensors 220a, 220b, 220c, and 220n arranged on the substrate 110 and configured to absorb light of different wavelength spectrum. Descriptions for the first, second, third, and $n^{th}$ light sources 210a, 210b, 210c, and 210n and the first, second, third, and $n^{th}$ sensors 220a, 220b, 220c, and 220n are the same as described above. The bio imaging system 100 according to the present example may have a configuration in which the aforementioned examples are combined according to a location. For example, as shown in FIGS. 16 and 17, a bio imaging system 100 may include a light source 210 that comprises first, second, and third light sources 210a, 210b, and 210c that may be configured to emit (e.g., selectively emit) light of different emission spectra within visible to infrared wavelength spectra, and the bio imaging system 100 may include a sensor 220 that comprises first, second, and third sensors 220a, 220b, and 220c that may be configured to absorb (e.g., selectively absorb) light of different absorption spectra in relation to each other within the visible to infrared wavelength spectra. As shown, the light source 210 and the sensor 220 may extending parallel (e.g., extend in a linear sequence) along an in-plane direction of the substrate 110.

Hereinafter, an example of the bio imaging system 100 shown in FIGS. 1 to 2B will be described with reference to FIGS. 18 to 21.

Figure 18:
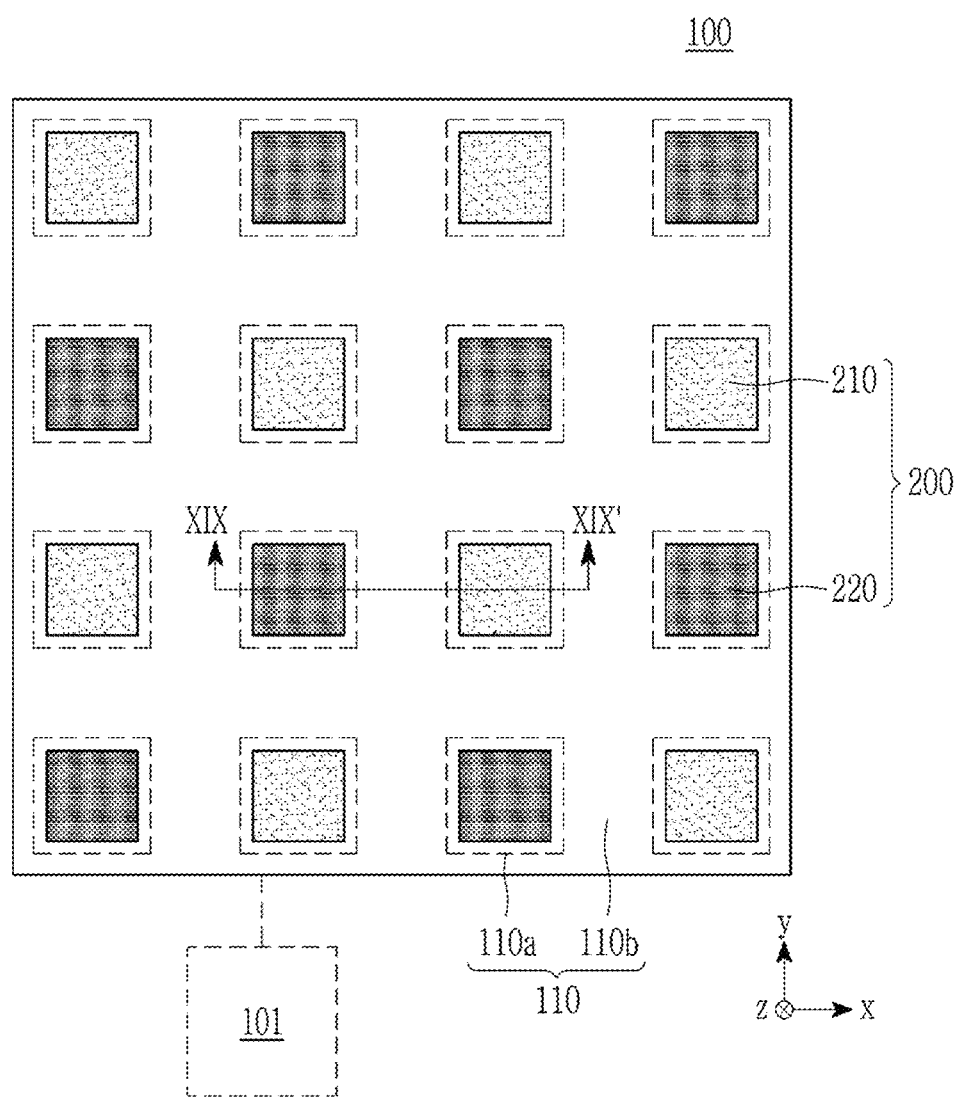
FIG. 18 is a plan view showing an example of the bio imaging system shown in FIGS. 1 to 2C according to some example embodiments.
Figure 19:
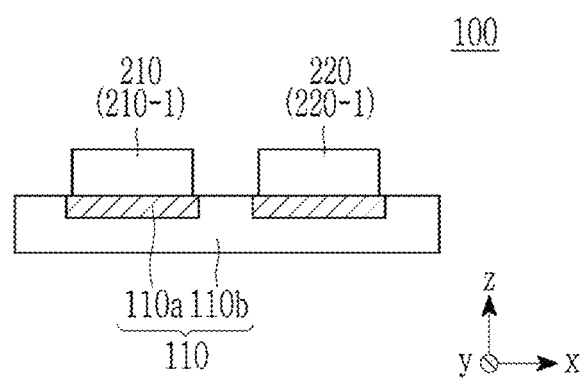
FIG. 19 is a cross-sectional view of an example of the bio imaging system of FIG. 18 taken along line XIX-XIX' according to some example embodiments.
Figure 20:
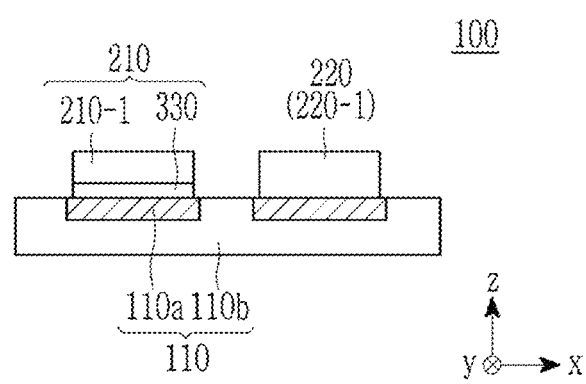
FIG. 20 is a cross-sectional view of another example of the bio imaging system of FIG. 18 taken along line XIX-XIX' according to some example embodiments.
Figure 21:
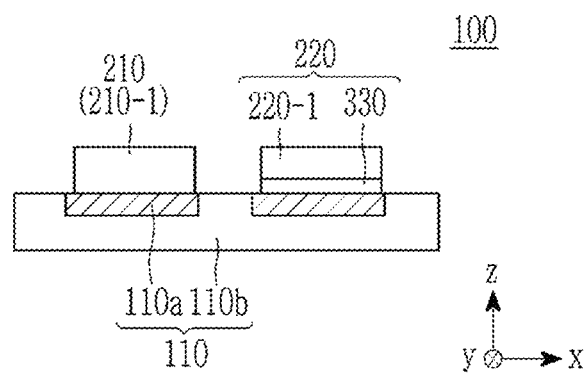
FIG. 21 is a cross-sectional view of another example of the bio imaging system of FIG. 18 taken along line XIX-XIX' according to some example embodiments.

FIG. 18 is a plan view showing an example of the bio imaging system shown in FIGS. 1 to 2C, FIG. 19 is a cross-sectional view of an example of the bio imaging system of FIG. 18 taken along line XIX-XIX', FIG. 20 is a cross-sectional view of another example of the bio imaging system of FIG. 18 taken along line XIX-XIX', and FIG. 21 is a cross-sectional view of another example of the bio imaging system of FIG. 18 taken along line XIX-XIX'.

Referring to FIGS. 18 to 21, the bio imaging system 100 according to each example may include a substrate 110; a plurality of light sources 210 arranged on the substrate 110; and a plurality of sensors 220 arranged on the substrate 110. The plurality of light sources 210 and the plurality of sensors 220 may be alternately arranged along rows and/or columns. Each light source 210 may include a light emitting element 210-1, and each sensor 220 may include a light absorption element 220-1.

However, referring to FIGS. 18 and 19, unlike the light absorption element 220-1 according to the aforementioned examples, the light absorption element 220-1 may be a wavelength-tunable light absorption element whose absorption spectrum is configured to change depending on an applied voltage bias and which may be configured to selectively absorb light of an absorption spectrum that changes based on a voltage applied to the wavelength-tunable light absorption element. For example, some of the light absorption elements 220-1 may be configured to absorb light of a first absorption spectrum having a first maximum absorption wavelength $\lambda_{A1,max}$ by applying a first voltage bias, some of the light absorption elements 220-1 may be configured to absorb light of a second absorption spectrum having a second maximum absorption wavelength $\lambda_{A2,max}$ by applying a second voltage bias different from the first voltage bias, some of the light absorption elements 220-1 may be configured to absorb light of a third absorption spectrum having a third maximum absorption wavelength $\lambda_{A3,max}$ by applying a third voltage bias different from the first and second voltage biases, and some of the light absorption elements 220-1 may be configured to absorb light of the $n^{th}$ absorption spectrum having the $n^{th}$ absorption wavelength $\lambda_{An,max}$ by applying an $n^{th}$ voltage bias different from the first, second, and third voltage biases. Accordingly, different voltage biases may be applied to each light absorption element 220-1 to absorb light of a desired absorption spectrum, and thereby the same or substantially the same effect as the aforementioned first, second, third, and $n^{th}$ light absorption elements 220a-1, 220b-1, 220c-1, and 220n-1 may be obtained.

As another example, the light emitting element 210-1 may be a wavelength-tunable light emitting element instead of the aforementioned wavelength-tunable light absorption element and which may be configured to selectively emit light of an emission spectrum that changes based on a voltage applied to the wavelength-tunable light emitting element. For example, some of the light emitting elements 210-1 may be configured to emit light of a first emission spectrum having a first maximum emission wavelength $\lambda_{E1,max}$ by applying a first voltage bias, some of the light emitting elements 210-1 may be configured to emit light of a second emission spectrum having a second maximum emission wavelength $\lambda_{E2,max}$ by applying a second voltage bias different from the first voltage bias, some of the light emitting elements 210-1 may be configured to emit light of a third emission spectrum having a third maximum emission wavelength $\lambda_{E3,max}$ by applying a third voltage bias different from the first and second voltage biases, and some of the light emitting elements 210-1 may be configured to emit light of an $n^{th}$ emission spectrum having the $n^{th}$ maximum emission wavelength $\lambda_{En,max}$ by applying an $n^{th}$ voltage bias different from the first, second, and third voltage biases. Accordingly, different voltage biases may be applied to each light emitting element 210-1 to emit light of a desired emission spectrum, and thereby the same or substantially the same effect as the aforementioned first, second, third, and $n^{th}$ light emitting elements 210a-1, 210b-1, 210c-1, and 210n-1 may be obtained.

Next, referring to FIGS. 18 and 20, the light source 210 may include a light emitting element 210-1 and a wavelength-tunable color filter 330. The light emitting element 210-1 may be configured to emit light of a very wide emission spectrum, such as white light. The wavelength-tunable color filter 330 may have a transmission wavelength spectrum and/or transmittance changeable depending on a voltage applied thereto (e.g., applied to the wavelength-tunable color filter 330) and include, for example, an electro-optical material such as a liquid crystal, a plasmon material, and the like but is not limited thereto. For example, some of the wavelength-tunable color filters 330 may be configured to selectively transmit light of a first transmission spectrum having a first maximum transmission wavelength $\lambda_{T1,max}$ among light emitted from the light emitting element 210-1 by applying a first voltage bias, some of the wavelength-tunable color filters 330 may be configured to selectively transmit light of a second transmission spectrum having a second maximum transmission wavelength $\lambda_{T2,max}$ among the light emitted from the light emitting element 210-1 by applying a second voltage bias differing from the first voltage bias, and some of the wavelength-tunable color filters 330 may be configured to selectively transmit light of a third transmission spectrum having a third maximum transmission wavelength $\lambda_{T3,max}$ among the light emitted from the light emitting element 210-1 by applying a third voltage bias differing from the first and second voltage biases. Accordingly, different voltage biases may be applied to each light source 210 to emit light of a desired emission spectrum, and thereby the same or substantially the same effect as the aforementioned first, second, third, and $n^{th}$ light emitting elements 210a-1, 210b-1, 210c-1, and 210n-1 may be obtained.

As described herein, voltage biases may be applied to a wavelength-tunable element, layer, or the like (e.g., wavelength tunable color filter 330) by the controller 101 of the bio imaging system 100, for example based on a processor of the controller executing a program of instruction to apply a particular voltage bias to the wavelength tunable element to achieve a particular result (e.g., to cause the wavelength-tunable color filter 330 to selectively transmit light in a particular transmission spectrum having a particular maximum transmission wavelength).

Referring to FIGS. 18 and 21, a sensor 220 may include the light absorption element 220-1 and the wavelength-tunable color filter 330. The light source 210 and the light absorption element 220-1 may be configured to absorb, for example, light of a very wide wavelength spectrum such as white light and thus provide wavelength selectivity by the wavelength-tunable color filter 330. For example, some of the wavelength-tunable color filters 330 may be configured to selectively transmit light of a first transmission spectrum having a first maximum transmission wavelength $\lambda_{T1,max}$ among light reflected by the internal tissues of a living body (e.g., blood vessels) by applying a first voltage bias, some of the wavelength-tunable color filters 330 may be configured to selectively transmit light of a second transmission spectrum having a second maximum transmission wavelength $\lambda_{T2,max}$ among the light reflected by the internal tissues of a living body (e.g., blood vessels) by applying a second voltage bias differing from the first voltage bias, and some of the wavelength-tunable color filters 330 may be configured to selectively transmit light of a third transmission spectrum having a third maximum transmission wavelength $\lambda_{T3,max}$ among the light reflected by the internal tissues of a living body (e.g., blood vessels) by applying a third voltage bias differing from the first and second voltage biases. Accordingly, different voltage biases may be applied to each sensor 220 to absorb light of a desired absorption spectrum and thereby the same or substantially the same effect as the aforementioned first, second, third and $n^{th}$ light absorption elements 220a-1, 220b-1, 220c-1, and 220n-1 may be obtained.

Accordingly, the bio imaging system 100 may include a color filter 330 overlapped, in a direction that is perpendicular to an in-plane direction of the substrate 110 (e.g., the z direction as shown) with the light source 210 or the sensor 220, where the color filter 330 is a wavelength-tunable color filter configured to selectively transmit light in a transmission spectrum (e.g., a variable transmission spectrum) that may change based on a voltage applied to the color filter 330.

Hereinafter, an example of the bio imaging system 100 will be described with reference to FIGS. 22 to 24.

Figure 22:
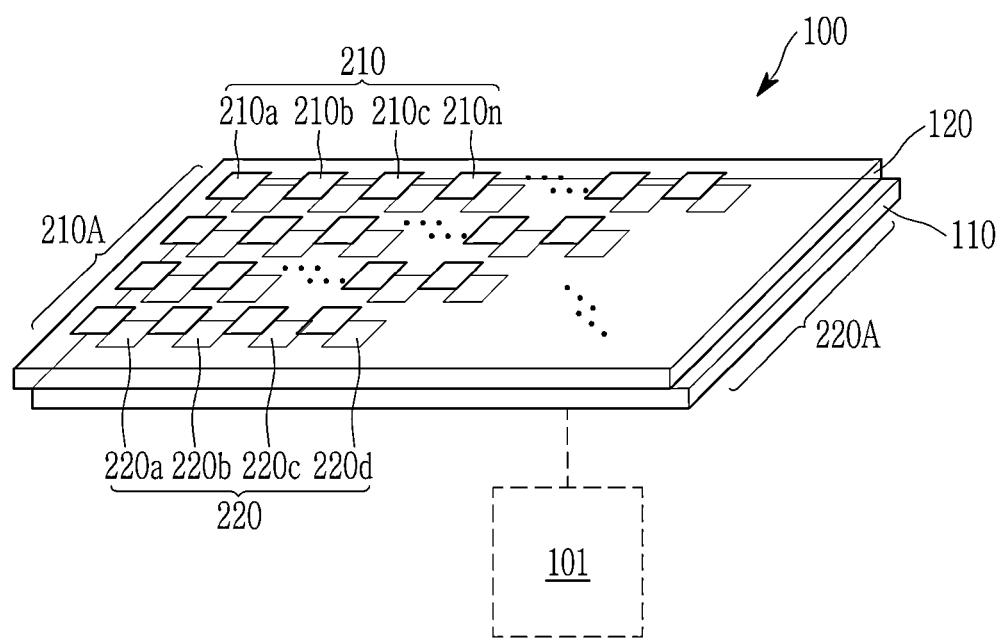
FIG. 22 is a plan view showing an example of a bio imaging system according to some example embodiments.
Figure 23:
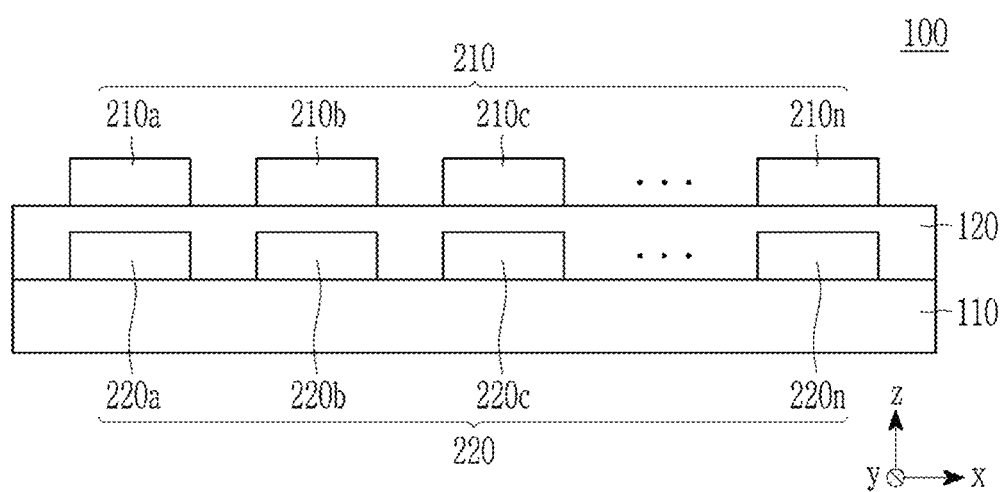
FIG. 23 is a cross-sectional view of a portion of an example of the bio imaging system of FIG. 22 according to some example embodiments.
Figure 24:
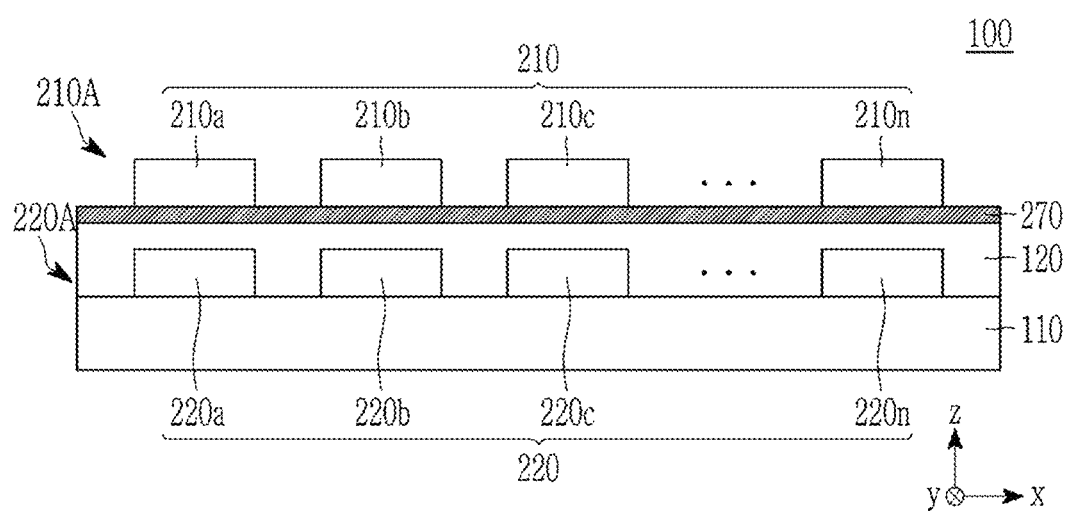
FIG. 24 is a cross-sectional view of a portion of another example of the bio imaging system of FIG. 22 according to some example embodiments.

FIG. 22 is a plan view showing an example of a bio imaging system according to some example embodiments, FIG. 23 is a cross-sectional view of a portion of an example of the bio imaging system of FIG. 22, and FIG. 24 is a cross-sectional view of a portion of another example of the bio imaging system of FIG. 22.

The bio imaging system 100 according to some example embodiments includes a substrate 110; a plurality of light sources 210 arranged on the substrate 110; and a plurality of sensors 220 arranged on the substrate 110, like the aforementioned example embodiments.

However, referring to FIGS. 22 and 23, in the bio imaging system 100 according to some example embodiments, unlike the aforementioned example embodiments, a plurality of light sources 210 and a plurality of sensors 220 are at a different height from the substrate 110, where "height" refers to a distance from the substrate 110 in a direction that extends perpendicular to an in-plane direction of the substrate 110 (e.g., a direction that extends perpendicular to the in-plane direction of the substrate 110). For example, as shown in FIGS. 22-23, the bio imaging system 100 may include a light source array 210A, including a plurality of light sources 210, and a sensor array 220A, including a plurality of sensors 220, wherein the light source array 210A and the sensor array 220A are at different heights from the substrate 110 in a direction extending perpendicular to an in-plane direction of the substrate 110 (e.g., the z direction, which extends perpendicular to an upper surface of the substrate 110).

In other words, the plurality of light sources 210 at a first height from the substrate 110 are arranged, for example, along a row and/or a column to form a light source array 210A, and the plurality of sensors 220 at a second height from the substrate 110 are arranged, for example, along a row and/or a column to form a sensor array 220A. For example, the first height may be higher than the second height. A transparent layer 120 may be between the light source array 210A and the sensor array 220A, and the transparent layer 120 may be a stretchable transparent layer.

Referring to FIG. 24, the bio imaging system 100 according to some example embodiments includes a substrate 110; a light source array 210A and a sensor array 220A at a different heights in relation to each other on the substrate 110; and a transparent layer 120 between the light source array 210A and the sensor array 220A, like the aforementioned example.

However, the bio imaging system 100 according to some example embodiments, unlike the aforementioned example embodiments, further includes a light diffusion layer 270 under the light source array 210A. The light diffusion layer 270 may be between the substrate 110 and the light source array 210A, for example, on the whole surface of the substrate 110. As shown, the light diffusion layer 270 may be between the light source array 210A and the sensor array 220A in the direction extending perpendicular to the in-plane direction of the substrate 110 (e.g., the Z direction). The light diffusion layer 270 may be configured to scatter and diffuse light irradiated from the light source array 210A to evenly supply the scattered and diffused light to a living body such as a skin.

The bio imaging system 100 may be applied to an electronic device such as a medical or security imaging device for identifying spatial information of the internal tissues of the living body, and this spatial information may be obtained temporarily or in real time. For example, the internal tissues of the living body may be blood vessels or internal organs, and the spatial information such as a location, shape, size and/or thickness of the blood vessels or internal organs may be used to predict or treat vascular diseases or diseases of internal organs in advance.

The bio imaging system 100 may be, for example, a wearable bio imaging system or a skin-attachable bio imaging system directly attached to the skin, and the skin-attachable bio imaging system may be, for example, a patch-type bio imaging system or a band-type bio imaging system.

The bio imaging system 100 may further include a driving unit such as an IC and a processor for obtaining an electrical signal as described above and separating and/or extracting spatial information of an internal tissue of the living body according to the electrical signal.

The bio imaging system 100 may further include a display unit for displaying images and spatial information of the internal tissue of the living body as various characters and/or images.

FIG. 34 is a schematic diagram of an electronic device 1300 according to some example embodiments. The electronic device 1300 shown in FIG. 34 may be an electronic device according to any of the example embodiments.

Referring to FIG. 34, an electronic device 1300 includes a processor 1320, a memory 1330, a sensor 1340, and a display device 1350 electrically connected through a bus 1310. The sensor 1340 may include the bio imaging system 100 according to any of the example embodiments. The display device 1350 may include a display panel, for example an OLED display panel. In the example embodiments shown in FIG. 34, the electronic device 1300 may include both a sensor 1340 and a display device 1350, but example embodiments are not limited thereto: in some example embodiments the electronic device 1300 may include one of the sensor 1340 or the display device 1350.

In some example embodiments, some or all of the electronic device 1300 may include or be included in a bio imaging system 100 according to any of the example embodiments. For example, in some example embodiments, the electronic device 1300 may include a bio imaging system 100 according to any of the example embodiments that includes and/or is included in at least one of the sensor 1340 or the display device 1350, and the memory 1330, processor 1320, and bus 1310 may be on the substrate 110 of the bio imaging system 100 and coupled to one or more electrodes of the bio imaging system 100. In some example embodiments, the bio imaging system 100 may be limited to the sensor 1340 and/or display device 1350 included in the electronic device 1300, wherein the bus 1310, memory 1330, and processor 1320 are external to the bio imaging system 100 and coupled thereto (e.g., via bus 1310) to establish the electronic device 1300.

The processor 1320 may perform a memory program and thus at least one function, including controlling the sensor 1340 and/or displaying an image on the display device 1350. The processor 1320 may generate an output.

As described herein, any devices, systems, electronic devices, blocks, modules, units, controllers, circuits, and/or portions thereof according to any of the example embodiments, and/or any portions thereof (including, without limitation, bio imaging system 100, controller 101, electronic device 1300, processor 1320, memory 1330, sensor 1340, display device 1350, or the like) may include, may be included in, and/or may be implemented by one or more instances of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), a neural network processing unit (NPU), an Electronic Control Unit (ECU), an Image Signal Processor (ISP), and the like. In some example embodiments, the processing circuitry may include a non-transitory computer readable storage device (e.g., a memory), for example a solid state drive (SSD), storing a program of instructions, and a processor (e.g., CPU) configured to execute the program of instructions to implement the functionality and/or methods performed by some or all of any devices, systems, electronic devices, blocks, modules, units, controllers, circuits, and/or portions thereof according to any of the example embodiments, and/or any portions thereof.

Any of the memories and/or storage devices described herein, including, without limitation, memory 1330, or the like, may be a non-transitory computer readable medium and may store a program of instructions. Any of the memories described herein may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM).

Referring to at least FIGS. 25, 26, 27A-27B, 28, 29, and 30, the bio imaging system 100 may include a controller 101 that may be configured to perform some or all of any of the methods described herein with regard to any of the example embodiments. The controller 101 may, for example, include one or more instances of processing circuitry as described herein, which may include a memory (e.g., memory 1330) that stores a program of instructions and a processor (e.g., processor 1320) that is configured to execute the program of instructions to cause the bio imaging system 100 to perform some or all of any of the methods as described herein according to any of the example embodiments.

For example, the controller 101 may be configured to control the light source 210 according to any example embodiments to cause the light source 210 to emit light as described herein according to any example embodiments to irradiate a skin of a living body. Where the light source 210 includes a plurality of light sources, for example light sources configured to emit light of different emission spectra within visible to infrared wavelength spectra, the controller 101 may control the light source 210 (e.g., via transmitting particular signals and/or voltages to the light source 210) to cause the various light sources thereof to sequentially emit light. As described herein, the emitted light may be scattered and/or reflected by internal tissue of the living body, and the sensor 220 may absorb such scattered and/or reflected light based on the emitted light irradiating the skin of the living body. The sensor 220 may generate one or more signals based on absorbing the light. The one or more signals may be received at the controller 101 from the sensor 220 and processed by the controller 101 to obtain (e.g., generate) a plurality of images (e.g., a plurality of images of the internal tissue based on light of different wavelength spectra) as described herein according to any example embodiments. The controller 101 may be configured to extract differences between the plurality of images to generate a plurality of extracted images of the internal tissue of the living body according to a depth from a skin surface of the skin, as described herein according to any example embodiments. Such extraction may include extracting a first image of an internal tissue of the living body located at a first depth from the skin surface based on processing the obtained images to determine a difference between an image generated based on causing a second light source of the light sources to emit light and an image generated based on causing a first light source of the light sources to emit light, and extracting a second image of the internal tissue of the living body located at a second depth deeper than the first depth based on a difference between an image generated based on causing a third light source of the light sources to emit light and the image generated based on causing the second light source to emit light. Where the sensor 220 includes multiple sensors (e.g., first, second, and third sensors) configured to absorb light of different absorption spectra in relation to each other, the extracting differences between the plurality of images may include extracting a first image of the internal tissue of the living body located at a first depth from the skin surface based on a difference between an image generated based on the second sensor absorbing light and an image generated based on the first sensor absorbing light, and extracting a second image of the internal tissue of the living body located at a second depth deeper than the first depth based on a difference between an image generated based on the third sensor absorbing light and the image generated based on the second sensor absorbing light. The controller 101 may configured to generate a three-dimensional image of the internal tissue of the living body based on combining the plurality of extracted images as described herein according to any of the example embodiments. The controller 101 may be configured to, prior to generating the three-dimensional image, generate a correction image from a portion of the light source or a portion of the sensor, and correct the plurality of extracted images using the correction image. The controller 101 may then generate the three-dimensional image based on combining the corrected extracted images. Obtained and/or generated images may be output, displayed, transmitted, or the like (e.g., on a display device as described herein). The controller 101 may obtain information image information of an internal tissue of a living body according to any of the methods of any of the example embodiments based on obtained (e.g., generated) images, including extracted and/or three-dimensional images as described herein, and may cause such information to be output, transmitted, displayed, etc.

Hereinafter, some example embodiments are illustrated in more detail with reference to examples. However, the scope of the inventive concepts is not limited to these examples.

Optical Simulation

Example 1

Each blood vessel image is evaluated when a plurality of blood vessels are distributed along the depth direction by using a bio imaging system.

Simulation conditions are as follows.
Bio imaging system having the structures shown in FIGS. 3 to 5D
Stretchable substrate thickness: 0.02 mm
Distribution of 3 blood vessels BV1, BV2 and BV3 according to depth
Light source: surface light source (Lambertian)
Maximum emission wavelength of first, second, and third light sources: 600 nm/700 nm/800 nm
Full width at half maximum (FWHM) of emission spectra of first, second, and third light sources: 100 nm/100 nm/100 nm
Upper electrode/lower electrode of light source (light emitting element): reflecting electrode/light-transmitting electrode
Internal quantum efficiency of the lower and upper light absorption elements is assumed to be 100%
Skin composition: skin thickness of 1.5 mm, fat thickness of 3 mm, muscle thickness of 30 mm,
Information of upper blood vessel (BV1): x=0 mm (ref.), z=1.5 mm (depth from skin surface), radius of 0.5 mm,
Information of middle blood vessel (BV2): x=4 mm, z=5 mm (depth from skin surface), radius of 1.5 mm,
Information of lower blood vessel (BV3): x=−3 mm, z=6 mm (depth from skin surface), radius of 1.0 mm,
The results are shown in FIGS. 31A, 31B, and 31C.

Figure 31A:
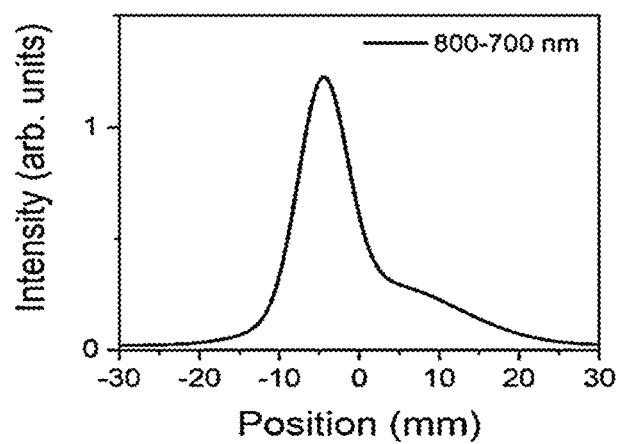
FIGS. 31A, 31B, and 31C are simulation graphs predicting the distribution of each blood vessel when a plurality of blood vessels are distributed along the depth direction using the bio imaging system according to Example 1 according to some example embodiments.
Figure 31B:
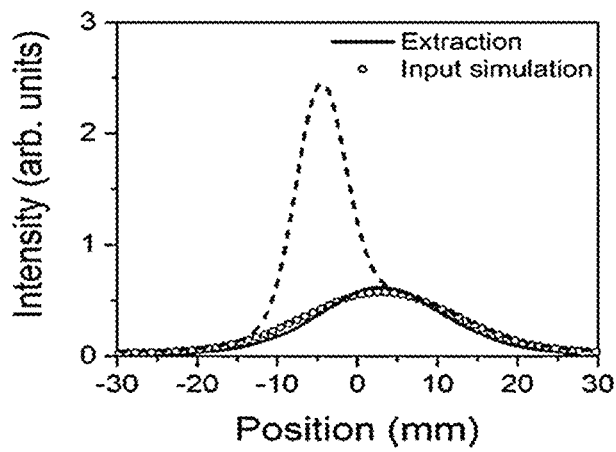
Figure 31C:
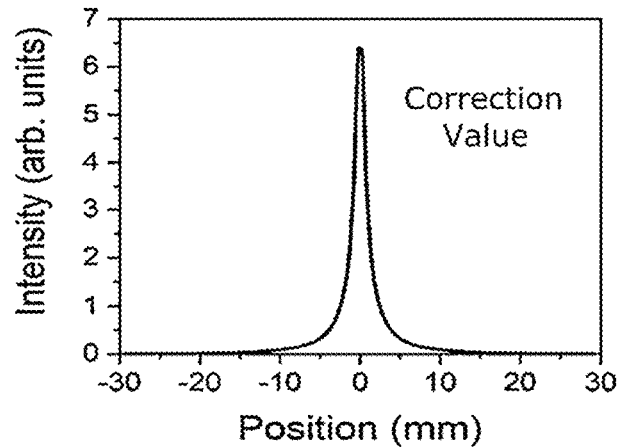

FIGS. 31A, 31B, and 31C are simulation graphs predicting the distribution of each blood vessel, when a plurality of blood vessels are distributed along the depth direction, using the bio imaging system according to Example 1.

When light is irradiated to the skin, light at a wavelength of 800 nm (first light source) and light at a wavelength of 700 nm (second light source) may reach each different depth of about 7 mm and 4 mm, and since a difference of images obtained from the first and second light sources, as shown in FIG. 31A, includes information of a depth section ranging from 4 mm to 7 mm, there is composed of two peak signals from the blood vessel BV2 and the lower vessel BV3. A skin light-scattering distribution (a correction value) is extracted, as shown in FIG. 31C, and then, applied to FIG. 31A to predict signals of the intermediate blood vessel BV2, which are the same as the extraction result of FIG. 31B. Compared with ideal data obtained from input data of the simulation (input simulation of the FIG. 31B), the signals are almost identical therewith. Accordingly, an image with a wavelength difference and a correction value by a skin light-scattering distribution may be used to relatively accurately extract specific blood vessels among a plurality of blood vessels overlapped in a depth direction.

Observation of Blood Vessel Image

Example 2

A bio imaging system including a wavelength-tunable light emitting element as a light source is attached to the back of a hand to examine a blood vessel image.

Figure 32:
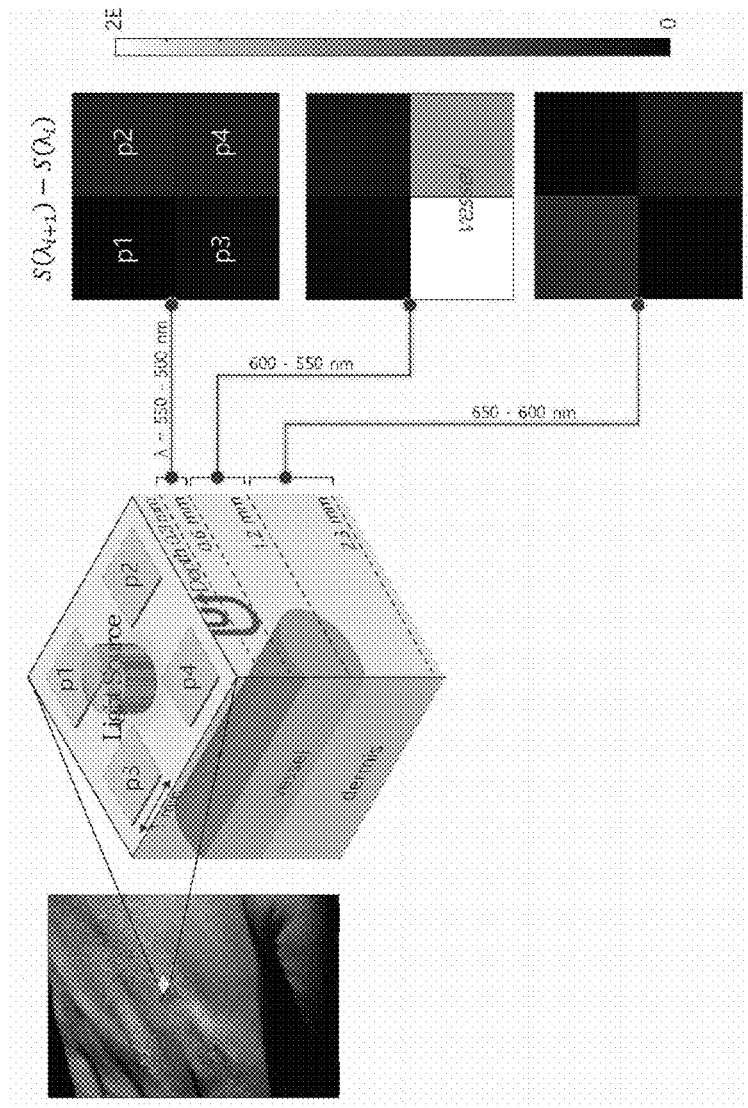
FIG. 32 is a graph showing a signal according to the depth of a living body obtained using the bio imaging system according to Example 2 according to some example embodiments.
Figure 33:
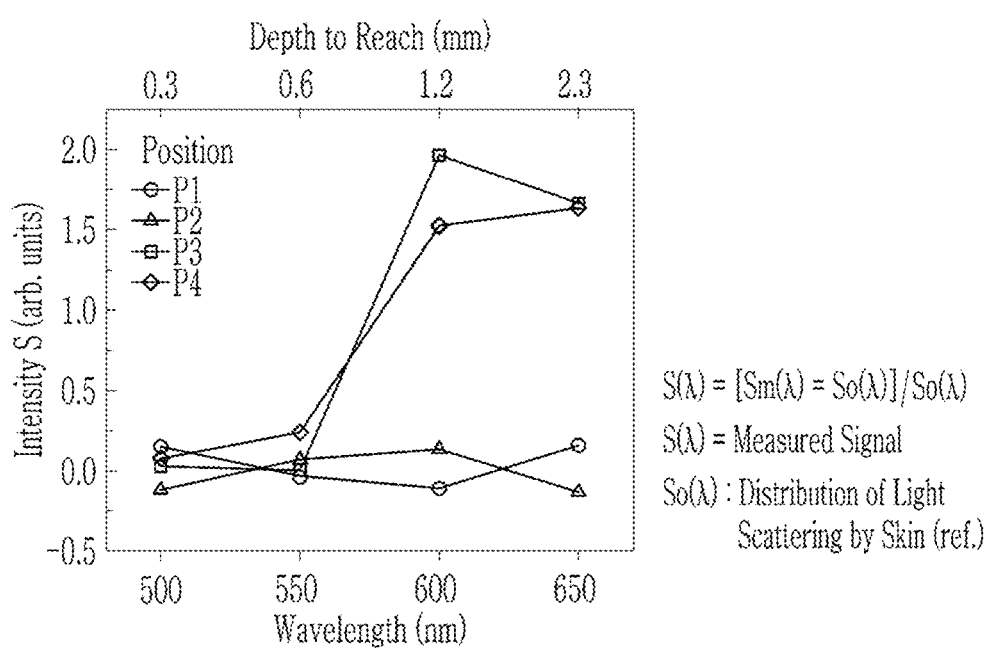
FIG. 33 is a graph showing signals for each wavelength measured in four pixels of FIG. 32 according to some example embodiments.

FIG. 32 is a graph showing a signal according to the depth of a living body obtained using the bio imaging system according to Example 2, and FIG. 33 is a graph showing signals for each wavelength measured in four pixels of FIG. 32.

Referring to FIG. 32, the bio imaging system including a wavelength-tunable light emitting element (550 nm to 650 nm) as a light source in which blood vessels are distributed is attached to the back of the hand to irradiate light and transmit the light scattered and reflected by the blood vessels and then, measure it in four different pixels at different positions p1, p2, p3, and p4. The blood vessels are disposed to be overlapped with the $3^{rd}$ pixel p3 and the $4^{th}$ pixel p4. Since the light irradiated from the light source reaches a different depth depending on a wavelength, an image "A" measured at the pixels p1, p2, p3, and p4 may be obtained from a difference between data obtained by using a light source of a wavelength of 550 nm and data obtained by using a light source of a wavelength of 500 nm. Likewise, an image "B" measured in the pixels p1, p2, p3, and p4 may be obtained from a difference between data obtained by using a light source of a wavelength of 600 nm and data obtained by using a light source of a wavelength of 550 nm. Similarly, an image "C" measured in the pixels p1, p2, p3, and p4 may be obtained from a difference between data obtained by using a light source of a wavelength of 650 nm and data obtained by using a light source of a wavelength of 600 nm. The images "A", "B", and "C" are displayed in colors based on the same scale bar, wherein the image "A" represents depth information between 0.6 mm to 0.3 mm from the skin surface, the image "B" represents depth information between 1.2 mm to 0.6 mm from the skin surface, and the image "B" represents depth information between 2.3 mm to 1.2 mm from the skin surface. Considering that high signals are detected at the two pixels p3 and p4 of the image "B", blood vessels located at a specific position and depth are surely detected.

FIG. 33 shows a signal depending on a wavelength measured in the four pixels p1, p2, p3, and p4, which are shown in FIG. 32, and as described above, a high signal at a depth (550 nm/600 nm) of 1.2 mm and 0.6 mm is detected in the two pixels p3 and p4. The signals (S) obtained at this time may be obtained by correcting an actually-measured value ($S_m(\lambda)$) with a skin light-scattering distribution ($S_0(\lambda)$, correction value) measured at a position where there are no blood vessels (e.g., p1 and p2).

While the inventive concepts have been described in connection with what is presently considered to be practical example embodiments, it is to be understood that the inventive concepts are not limited to the these example embodiments. On the contrary, the scope of the inventive concepts is intended to cover various modifications and equivalent arrangements included within the spirit and scope of the appended claims.

What is claimed is:

1. A bio imaging system, comprising:
a substrate;
a light source on the substrate;
a sensor on the substrate rate; and
a controller,
wherein at least one of the light source or the sensor is configured to emit or absorb light of different wavelength spectra, and
wherein the controller is configured to obtain and combine a plurality of images obtained based on the light of different wavelength spectra to
obtain a three-dimensional image of an internal tissue of a living body, and
obtain information associated with the internal tissue, the information including at least one of a location of the internal tissue, a shape of the internal tissue, a size of the internal tissue, or a thick mess of the internal tissue.

2. The bio imaging system of claim 1, wherein the light source comprises first, second, and third light sources configured to emit light of different emission spectra within visible to infrared wavelength spectra.

3. The bio imaging system of claim 2, wherein
the first light source comprises a first light emitting element configured to emit light of a first emission spectrum having a first maximum emission wavelength,
the second light source comprises a second light emitting element configured to emit light of a second emission spectrum having a second maximum emission wavelength that is longer than the first maximum emission wavelength,
the third light source comprises a third light emitting element configured to emit light of a third emission spectrum having a third maximum emission wavelength that is longer than the second maximum emission wavelength, and
a difference between the first and second maximum emission wavelengths and a difference between the second and third maximum emission wavelengths are each greater than or equal to about 10 nm.

4. The bio imaging system of claim 2, wherein
each of the first, second and third light sources comprises a separate light emitting element of a plurality of light emitting elements that is configured to emit light of a same emission spectrum, and
each of the first, second and third light sources further comprises a separate color filter of a plurality of color filters, wherein the plurality of color filters are overlapped with separate, respective light emitting elements of the plurality of light emitting elements in a direction that extends perpendicular to an in-plane direction of the substrate.

5. The bio imaging system of claim 4, wherein
the plurality of color filters comprises
a first color filter included in the first light source, the first color filter configured to selectively transmit light of a first transmission spectrum having a first maximum transmission wavelength,
a second color filter included in the second light source, the second color filter configured to selectively transmit light of a second transmission spectrum having a second maximum transmission wavelength that is longer than the first maximum transmission wavelength, and
a third color filter included in the third light source, the third color filter configured to selectively transmit light of a third transmission spectrum having a third maximum transmission wavelength that is longer than the second maximum transmission wavelength,
wherein each of the first, second, and third maximum transmission wavelengths is within the same emission spectrum that the plurality of light emitting elements are configured to emit, and
a difference between the first and second maximum transmission wavelengths and a difference between the second and third maximum transmission wavelengths are each greater than or equal to about 10 nm.

6. The bio imaging system of claim 2, wherein the first, second, and third light sources extend in a linear sequence along an in-plane direction of the substrate.

7. The bio imaging system of claim 1, wherein
the light source comprises a plurality of light emitting elements configured to emit light of a same emission spectrum, and
the bio imaging system further comprises a plurality of color filters overlapped with separate, respective light emitting elements of the plurality of light emitting elements in a direction extending perpendicular to an in-plane direction of the substrate, the plurality of color filters configured to provide wavelength selectivity to the same emission spectrum.

8. The bio imaging system of claim 1, wherein the sensor comprises first, second, and third sensors configured to absorb light of different absorption spectra in relation to each other within visible to infrared wavelength spectra.

9. The bio imaging system of claim 8, wherein
the first sensor comprises a first light absorption element configured to absorb light of a first absorption spectrum having a first maximum absorption wavelength,
the second sensor comprises a second light absorption element configured to absorb light of a second absorption spectrum having a second maximum absorption wavelength, the second maximum absorption wavelength being longer than the first maximum absorption wavelength,
the third sensor comprises a third light absorption element configured to absorb light of a third absorption spectrum having a third maximum absorption wavelength, the third maximum absorption wavelength being longer than the second maximum absorption wavelength, and
a difference between the first and second maximum absorption wavelengths and a difference between the second and third maximum absorption wavelengths are each greater than or equal to about 10 nm.

10. The bio imaging system of claim 8, wherein
each sensor of the first, second, and third sensors comprises a separate light absorption element of a plurality of light absorption elements and a separate color filter of a plurality of color filters, the separate color filter of the sensor being overlapped with the separate light absorption element of the sensor in a direction extending perpendicular to an in-plane direction of the substrate, wherein the plurality of light absorption elements are configured to absorb light of a same absorption spectrum.

11. The bio imaging system of claim 10, wherein
the plurality of color filters comprises
    a first color filter included in the first sensor, the first color filter configured to selectively transmit light of a first transmission spectrum having a first maximum transmission wavelength,
    a second color filter included in the second sensor, the second color filter configured to selectively transmit light of a second transmission spectrum having a second maximum transmission wavelength that is longer than the first maximum transmission wavelength, and
    a third color filter included in the third sensor, the third color filter configured to selectively transmit light of a third transmission spectrum having a third maximum transmission wavelength that is longer than the second maximum transmission wavelength,
    each of the first, second, and third maximum transmission wavelengths is within the same absorption spectrum that the plurality of light absorption elements are configured to absorb, and
    a difference between the first and second maximum transmission wavelengths and a difference between the second and third maximum transmission wavelengths are each greater than or equal to about 10 nm.

12. The bio imaging system of claim 8, wherein the first, second, and third sensors extend in a linear sequence along an in-plane direction of the substrate.

13. The bio imaging system of claim 1, wherein
the light source comprises first, second, and third light sources configured to emit light of different emission spectra within visible to infrared wavelength spectra, and
the sensor comprises first, second, and third sensors configured to absorb light of different absorption spectra in relation to each other within the visible to infrared wavelength spectra.

14. The bio imaging system of claim 13, wherein the light source and the sensor extend in a linear sequence along an in-plane direction of the substrate.

15. The bio imaging system of claim 1, further comprising a color filter overlapped with the light source or the sensor in a direction that is perpendicular to an in-plane direction of the substrate,
wherein the color filter is a wavelength-tunable color filter that is configured to selectively transmit light of a transmission spectrum that changes depending on a voltage applied to the wavelength-tunable color filter.

16. The bio imaging system of claim 1, wherein the light source comprises a wavelength-tunable light emitting element configured to selectively emit light of an emission spectrum that changes based on a voltage applied to the wavelength-tunable light emitting element.

17. The bio imaging system of claim 1, wherein the sensor comprises a wavelength-tunable light absorption element configured to selectively absorb light of an absorption spectrum that changes based on a voltage applied to the wavelength-tunable light absorption element.

18. The bio imaging system of claim 1, further comprising:
    a light source array including a plurality of light sources, the plurality of light sources including the light source, and
    a sensor array including a plurality of sensors, the plurality of sensors including the sensor,
    wherein the light source array and the sensor array are at different heights from the substrate in a direction extending perpendicular to an in-plane direction of the substrate.

19. The bio imaging system of claim 18, further comprising a light diffusion layer between the light source array and the sensor array.

20. An electronic device comprising the bio imaging system of claim 1.

21. A bio imaging method, comprising:
    fixing the bio imaging system of claim 1 on a skin of a living body;
    causing the light source of the bio imaging system to emit light to irradiate the skin; and
    causing the sensor of the bio imaging system to absorb light scattered and reflected by internal tissue of the living body through the skin to obtain a plurality of images based on light of different wavelength spectra and to combine the plurality of images to obtain information associated with the internal tissue, the information including at least one of a location of the internal tissue, a shape of the internal tissue a size of the internal tissue, or a thickness of the internal tissue.

22. The bio imaging method of claim 21, further comprising:
    extracting differences between the plurality of images to obtain a plurality of extracted images of the internal tissue of the living body according to a depth from a skin surface of the skin.

23. The bio imaging method of claim 22, wherein
the light source comprises first, second, and third light sources configured to emit light of different emission spectra within visible to infrared wavelength spectra, and
the causing the light source of the bio imaging system to emit light comprises causing the first, second, and third light sources to sequentially emit light.

24. The bio imaging method of claim 23, wherein
the extracting differences between the plurality of images comprises
    extracting a first image of the internal tissue of the living body located at a first depth from the skin surface based on a difference between an image obtained based on causing the second light source to emit light and an image obtained based on causing the first light source to emit light, and
    extracting a second image of the internal tissue of the living body located at a second depth deeper than the first depth based on a difference between an image obtained based on causing the third light source to emit light and the image obtained based on causing the second light source to emit light.

25. The bio imaging method of claim 23, wherein
the sensor comprises first, second, and third sensors configured to absorb light of different absorption spectra in relation to each other, and
the extracting differences between the plurality of images comprises extracting a first image of the internal tissue of the living body located at a first depth from the skin surface based on a difference between an image obtained based on the second sensor absorbing light and an image obtained based on the first sensor absorbing light, and extracting a second image of the internal tissue of the living body located at a second depth deeper than the first depth based on a difference between an image obtained based on the third sensor absorbing light and the image obtained based on the second sensor absorbing light.

26. The bio imaging method of claim 22, further comprising obtaining a three-dimensional image of the internal tissue of the living body based on combining the plurality of extracted images.

27. The bio imaging method of claim 26, further comprising:

prior to obtaining the three-dimensional image,
obtaining a correction image from a portion of the light source or a portion of the sensor, and
correcting the plurality of extracted images using the correction image.

28. The bio imaging method of claim 21, wherein the internal tissue of the living body comprises a blood vessel.

29. A bio imaging system, comprising:

a memory storing a program of instructions; and
a processor configured to execute the program of instructions to
control a light source to cause the light source to emit light to irradiate a skin of a living body;
process signals generated by a sensor based on the sensor absorbing light scattered and reflected by internal tissue of the living body through the skin of the living body based on the emitted light irradiating the skin of the living body to generate a plurality of images of the internal tissue based on light of different wavelength spectra;
combine the plurality of images to information associated with the internal tissue, the information including at least one of a location of the internal tissue, a shape of the internal tissue, a size of the internal tissue, or a thickness of the in tissue; and
extract differences between the plurality of images to generate a plurality of extracted images of the internal tissue of the living body according to a depth from a skin surface of the skin.

30. The bio imaging system of claim 29, wherein
the light source includes first, second, and third light sources configured to emit light of different emission spectra within visible to infrared wavelength spectra,
the controlling the light source includes causing the first, second, and third light sources to sequentially emit light, and
the extracting differences between the plurality of images includes
extracting a first image of an internal tissue of the living body located at a first depth from the skin surface based on a difference between an image generated based on causing the second light source to emit light and an image generated based on causing the first light source to emit light, and
extracting a second image of the internal tissue of the living body located at a second depth deeper than the first depth based on a difference between an image generated based on causing the third light source to emit light and the image generated based on causing the second light source to emit light.

31. The bio imaging system of claim 29, wherein
the sensor includes first, second, and third sensors configured to absorb light of different absorption spectra in relation to each other, and
the extracting differences between the plurality of images includes
extracting a first image of the internal tissue of the living body located at a first depth from the skin surface based on a difference between an image generated based on the second sensor absorbing light and an image generated based on the first sensor absorbing light, and
extracting a second image of the internal tissue of the living body located at a second depth deeper than the first depth based on a difference between an image generated based on the third sensor absorbing light and the image generated based on the second sensor absorbing light.

32. The bio imaging system of claim 29, wherein the processor is configured to execute the program of instructions to generate a three-dimensional image of the internal tissue of the living body based on combining the plurality of extracted images.

33. The bio imaging system of claim 32, wherein the processor is configured to execute the program of instructions to, prior to generating the three-dimensional image,
generate a correction image from a portion of the light source or a portion of the sensor, and
correct the plurality of extracted images using the correction image.

* * * * *